US009221986B2

(12) United States Patent
Sujeeth et al.

(10) Patent No.: US 9,221,986 B2
(45) Date of Patent: *Dec. 29, 2015

(54) SELF-DISPERSING PARTICLES AND METHODS FOR MAKING AND USING THE SAME

(75) Inventors: Puthalath K. Sujeeth, Ballwin, MO (US); John P. Kane, Ellisville, MO (US); Daniel A. Ouellette, St. Peters, MO (US); Mark Ulrich, Florissant, MO (US)

(73) Assignee: Sensient Colors LLC, St. Louis, MO (US)

( * ) Notice: Subject to any disclaimer, the term of this patent is extended or adjusted under 35 U.S.C. 154(b) by 368 days.

This patent is subject to a terminal disclaimer.

(21) Appl. No.: 12/756,175

(22) Filed: Apr. 7, 2010

(65) Prior Publication Data
US 2010/0251932 A1    Oct. 7, 2010

Related U.S. Application Data

(60) Provisional application No. 61/167,419, filed on Apr. 7, 2009.

(51) Int. Cl.
| C09D 11/00 | (2014.01) |
| C09D 11/037 | (2014.01) |
| A61K 8/44 | (2006.01) |
| A61Q 1/02 | (2006.01) |
| C07D 251/54 | (2006.01) |
| C09B 67/04 | (2006.01) |
| C09B 67/08 | (2006.01) |
| C09B 67/46 | (2006.01) |
| C09C 1/24 | (2006.01) |
| C09C 1/36 | (2006.01) |
| C09C 3/12 | (2006.01) |
| C09D 7/00 | (2006.01) |
| C09D 11/326 | (2014.01) |
| C09D 11/328 | (2014.01) |
| C09D 15/00 | (2006.01) |
| G02B 5/22 | (2006.01) |

(52) U.S. Cl.
CPC .............. *C09D 11/037* (2013.01); *A61K 8/445* (2013.01); *A61Q 1/02* (2013.01); *C07D 251/54* (2013.01); *C09B 67/0002* (2013.01); *C09B 67/0009* (2013.01); *C09B 67/0086* (2013.01); *C09C 1/24* (2013.01); *C09C 1/3684* (2013.01); *C09C 3/12* (2013.01); *C09D 7/007* (2013.01); *C09D 11/326* (2013.01); *C09D 11/328* (2013.01); *C09D 15/00* (2013.01); *G02B 5/223* (2013.01); *A61K 2800/412* (2013.01); *A61K 2800/622* (2013.01); *C01P 2002/85* (2013.01); *C01P 2004/62* (2013.01); *C01P 2006/22* (2013.01); *C01P 2006/62* (2013.01); *C01P 2006/63* (2013.01); *C01P 2006/64* (2013.01)

(58) Field of Classification Search
CPC . C09B 67/0032; C09B 67/0016; C09D 11/30
USPC ........ 106/31.6, 400, 401, 412, 413, 425, 436, 106/456
See application file for complete search history.

(56) References Cited

U.S. PATENT DOCUMENTS

| 630,868 A | 8/1899 | Dorman |
| 1,901,861 A | 3/1933 | Baker |
| 2,034,508 A | 3/1936 | Boer et al. |
| 2,178,383 A | 10/1939 | Wiegand |
| 2,281,261 A | 4/1942 | Bjorksten et al. |
| 2,439,442 A | 4/1948 | Amon et al. |
| 2,439,443 A | 4/1948 | Aske |
| 2,641,533 A | 6/1953 | Cines |
| 2,811,501 A | 10/1957 | Stedry |

(Continued)

FOREIGN PATENT DOCUMENTS

| AU | 768805 | 1/2004 |
| CA | 2198750 | 3/1996 |

(Continued)

OTHER PUBLICATIONS

International Search Report and Written Opinion for Application No. PCT/US2010/030311 dated Aug. 3, 2011 (14 pages).
United States Patent Office Action for U.S. Appl. No. 13/042,803 dated Aug. 10, 2011 (10 pages).
United States Patent Office Notice of Allowance for U.S. Appl. No. 13/109,865 dated Oct. 19, 2011 (5 pages).
Invitation to Pay Additional Fees and Partial International Search for Application No. PCT/US2010/030311 dated Dec. 7, 2010 (5 pages).
United States Patent Office Notice of Allowance for U.S. Appl. No. 11/933,116 dated Dec. 10, 2010 (4 pages).
United States Patent Office Notice of Allowance for U.S. Appl. No. 12/197,087 dated Feb. 9, 2011 (3 pages).
United States Patent Office Notice of Allowance for U.S. Appl. No. 11/933,192 dated Mar. 2, 2011 (12 pages).
United States Patent Office Notice of Allowance for U.S. Appl. No. 13/355,131 dated Mar. 27, 2012 (9 pages).

(Continued)

*Primary Examiner* — Veronica F Faison
(74) *Attorney, Agent, or Firm* — Michael Best & Friedrich LLP

(57) ABSTRACT

A method of modifying a particle that includes reacting a reactive compound having an X—$[Y]_n$ reactive group with a secondary compound N—S-ZM to form a substituted reactive intermediate $[Y]_a$—X—$(N$—S-ZM$)_b$, and reacting the particle with the substituted reactive intermediate $[Y]_a$—X—$(N$—S-ZM$)_b$ to attach the substituted reactive intermediate to the surface of the particle to form a surface modified particle. The particle may comprise at least one of a dye particle, an inorganic pigment particle, an additive, or a combination thereof. X may be a sulfonyl, phosphoryl, or 1,3,5-triazinyl group. Y may be a halogen leaving group. N may be a nucleophilic group. S may be an organic group. ZM may be an ionizable end group. Also, n is an integer between 1 and 3, b is an integer between 1 and 3, and a=n−b. When n is equal to or greater than b, and wherein if b is 2 or 3, each N—S-ZM can be the same or different.

26 Claims, 22 Drawing Sheets

(56) References Cited

U.S. PATENT DOCUMENTS

| | | |
|---|---|---|
| 2,816,046 A | 12/1957 | Damusis |
| 2,867,540 A | 1/1959 | Melvin |
| 2,993,903 A | 7/1961 | Kraus |
| 3,023,118 A | 2/1962 | Donnet |
| 3,025,259 A | 3/1962 | Watson et al. |
| 3,043,708 A | 7/1962 | Edwin et al. |
| 3,243,752 A | 3/1966 | Lawrence |
| 3,271,383 A | 9/1966 | Yamaya et al. |
| 3,291,788 A | 12/1966 | Yamaya et al. |
| 3,306,761 A | 2/1967 | Johnson |
| 3,323,932 A | 6/1967 | Aboytes et al. |
| 3,347,632 A | 10/1967 | Parker |
| 3,368,990 A | 2/1968 | Goulston |
| 3,412,054 A | 11/1968 | Milligan et al. |
| 3,442,679 A | 5/1969 | Rivin et al. |
| 3,519,452 A | 7/1970 | Rivin et al. |
| 3,528,840 A | 9/1970 | Aboytes |
| 3,565,657 A | 2/1971 | Dannenberg et al. |
| 3,623,899 A | 11/1971 | Lagally |
| 3,697,425 A | 10/1972 | Lagally |
| 3,755,287 A | 8/1973 | Hegar et al. |
| 3,895,004 A | 7/1975 | de Montmollin et al. |
| 3,901,818 A | 8/1975 | Durand et al. |
| 3,971,849 A | 7/1976 | Prasad et al. |
| 3,992,218 A | 11/1976 | Suetsugu et al. |
| 4,003,981 A | 1/1977 | Turk |
| 4,069,218 A | 1/1978 | Hegar |
| 4,156,616 A | 5/1979 | Dietz et al. |
| 4,197,221 A | 4/1980 | Eisenmenger et al. |
| 4,201,647 A | 5/1980 | Spaziante et al. |
| 4,243,772 A | 1/1981 | Paul et al. |
| 4,298,526 A | 11/1981 | Sappok et al. |
| 4,343,767 A | 8/1982 | Long et al. |
| 4,386,851 A | 6/1983 | Eidorff |
| 4,388,115 A | 6/1983 | Sugiyama et al. |
| 4,406,662 A | 9/1983 | Beran et al. |
| 4,425,162 A | 1/1984 | Sugiyama et al. |
| 4,435,717 A | 3/1984 | Eida et al. |
| 4,477,621 A | 10/1984 | Sato et al. |
| 4,485,041 A | 11/1984 | Hoyer et al. |
| 4,500,672 A | 2/1985 | Suzuki et al. |
| 4,507,236 A | 3/1985 | Seiler et al. |
| 4,508,570 A | 4/1985 | Fujii et al. |
| 4,530,961 A | 7/1985 | Nguyen et al. |
| 4,532,296 A | 7/1985 | Gardner |
| 4,533,776 A | 8/1985 | Baasner et al. |
| 4,581,445 A | 4/1986 | Ramanathan |
| 4,597,794 A | 7/1986 | Ohta et al. |
| 4,609,404 A | 9/1986 | Marraccini et al. |
| 4,624,709 A | 11/1986 | Otsuka |
| 4,624,773 A | 11/1986 | Hettinger |
| 4,627,875 A | 12/1986 | Kobayashi et al. |
| 4,631,085 A | 12/1986 | Kawanishi et al. |
| 4,647,310 A | 3/1987 | Shimada et al. |
| 4,666,519 A | 5/1987 | Akiyama et al. |
| 4,666,993 A | 5/1987 | Urano et al. |
| 4,670,059 A | 6/1987 | Hackleman et al. |
| 4,680,332 A | 7/1987 | Hair et al. |
| 4,683,002 A | 7/1987 | Mirua et al. |
| 4,685,968 A | 8/1987 | Palmer |
| 4,689,078 A | 8/1987 | Koike |
| 4,694,302 A | 9/1987 | Hackleman |
| 4,695,824 A | 9/1987 | Tazaki |
| 4,711,668 A | 12/1987 | Shimada et al. |
| 4,713,081 A | 12/1987 | Becker |
| 4,713,113 A | 12/1987 | Shimada et al. |
| 4,732,613 A | 3/1988 | Shioya et al. |
| 4,737,190 A | 4/1988 | Shimada et al. |
| 4,761,180 A | 8/1988 | Askeland et al. |
| 4,765,838 A | 8/1988 | Ohata et al. |
| 4,786,327 A | 11/1988 | Wenzel et al. |
| 4,790,880 A | 12/1988 | Miller |
| 4,793,860 A | 12/1988 | Murakami et al. |
| 4,798,856 A | 1/1989 | Ayala et al. |
| 4,810,292 A | 3/1989 | Palmer |
| 4,836,851 A | 6/1989 | Pawlowski et al. |
| 4,836,852 A | 6/1989 | Knirsch et al. |
| 4,838,938 A | 6/1989 | Tomida |
| 4,844,569 A | 7/1989 | Wada et al. |
| 4,846,851 A | 7/1989 | Guro et al. |
| 4,853,036 A | 8/1989 | Koike et al. |
| 4,853,037 A | 8/1989 | Johnson et al. |
| 4,855,762 A | 8/1989 | Suzuki |
| 4,914,562 A | 4/1990 | Abe et al. |
| 4,931,950 A | 6/1990 | Isle et al. |
| 4,952,551 A | 8/1990 | Buehler |
| 4,952,617 A | 8/1990 | Ayala et al. |
| 4,957,553 A | 9/1990 | Koike |
| 4,959,661 A | 9/1990 | Buxton |
| 4,973,499 A | 11/1990 | Iwata et al. |
| 4,978,969 A | 12/1990 | Chieng |
| 4,994,110 A | 2/1991 | Stoffel et al. |
| 5,013,361 A | 5/1991 | Case et al. |
| 5,017,224 A | 5/1991 | Tomita |
| 5,017,227 A | 5/1991 | Koike et al. |
| 5,017,644 A | 5/1991 | Fuller et al. |
| 5,026,425 A | 6/1991 | Hindagolla et al. |
| 5,026,426 A | 6/1991 | Russell |
| 5,026,427 A | 6/1991 | Mitchell et al. |
| 5,053,078 A | 10/1991 | Koike |
| 5,059,248 A | 10/1991 | Signorino et al. |
| 5,061,316 A | 10/1991 | Moffatt |
| 5,062,892 A | 11/1991 | Halko |
| 5,067,980 A | 11/1991 | Koike |
| 5,075,699 A | 12/1991 | Koike |
| 5,082,496 A | 1/1992 | Yamamoto et al. |
| 5,085,698 A | 2/1992 | Ma et al. |
| 5,102,459 A | 4/1992 | Ritter et al. |
| 5,103,361 A | 4/1992 | Nagatsuka |
| 5,106,417 A | 4/1992 | Hauser |
| 5,108,501 A | 4/1992 | Moffatt |
| 5,108,503 A | 4/1992 | Hindagolla et al. |
| 5,108,504 A | 4/1992 | Johnson |
| 5,110,355 A | 5/1992 | Pendleton |
| 5,114,479 A | 5/1992 | Keaveney |
| 5,116,409 A | 5/1992 | Moffatt |
| 5,118,351 A | 6/1992 | Shirota et al. |
| 5,124,201 A | 6/1992 | Kurabayashi et al. |
| 5,125,969 A | 6/1992 | Nishiwaki et al. |
| 5,133,803 A | 7/1992 | Moffatt |
| 5,142,393 A | 8/1992 | Okumura et al. |
| 5,145,518 A | 9/1992 | Winnik et al. |
| 5,156,470 A | 10/1992 | Suzuki et al. |
| 5,156,472 A | 10/1992 | Suzuki et al. |
| 5,156,473 A | 10/1992 | Suzuki et al. |
| 5,156,675 A | 10/1992 | Breton et al. |
| 5,158,377 A | 10/1992 | Suzuki et al. |
| 5,159,009 A | 10/1992 | Wolff |
| 5,160,372 A | 11/1992 | Matrick |
| 5,165,968 A | 11/1992 | Johnson et al. |
| 5,172,133 A | 12/1992 | Suga et al. |
| 5,176,745 A | 1/1993 | Moore et al. |
| 5,181,045 A | 1/1993 | Shields |
| 5,183,502 A | 2/1993 | Meichsner |
| 5,184,148 A | 2/1993 | Suga |
| 5,190,582 A | 3/1993 | Shinozuka et al. |
| 5,196,057 A | 3/1993 | Escano et al. |
| 5,207,824 A | 5/1993 | Moffatt |
| 5,211,747 A | 5/1993 | Breton et al. |
| 5,212,819 A | 5/1993 | Wada |
| 5,215,577 A | 6/1993 | Eida et al. |
| 5,220,346 A | 6/1993 | Carreira et al. |
| 5,221,148 A | 6/1993 | Suzuki et al. |
| 5,221,332 A | 6/1993 | Kohlmeier |
| 5,221,334 A | 6/1993 | Ma et al. |
| 5,246,518 A | 9/1993 | Hale |
| 5,248,363 A | 9/1993 | Hale |
| 5,258,066 A | 11/1993 | Kobayashi et al. |
| 5,258,505 A | 11/1993 | Eida et al. |
| 5,262,268 A | 11/1993 | Bertrand |
| 5,272,201 A | 12/1993 | Ma et al. |
| 5,281,261 A | 1/1994 | Lin |
| 5,281,569 A | 1/1994 | Amon et al. |
| 5,296,022 A | 3/1994 | Kobayashi et al. |

(56) References Cited

U.S. PATENT DOCUMENTS

| | | |
|---|---|---|
| 5,300,148 A | 4/1994 | Domingo et al. |
| 5,302,223 A | 4/1994 | Hale |
| 5,310,778 A | 5/1994 | Shor et al. |
| 5,318,617 A | 6/1994 | Nagasawa et al. |
| 5,320,668 A | 6/1994 | Shields |
| 5,334,435 A | 8/1994 | Rossi |
| 5,342,439 A | 8/1994 | Lauw |
| 5,344,483 A | 9/1994 | Hinton |
| 5,352,484 A | 10/1994 | Bernard et al. |
| 5,364,461 A | 11/1994 | Beach et al. |
| 5,364,462 A | 11/1994 | Crystal |
| 5,364,702 A | 11/1994 | Idei |
| 5,372,697 A | 12/1994 | Akutsu et al. |
| 5,377,024 A | 12/1994 | Dillinger |
| 5,378,269 A | 1/1995 | Rossi |
| 5,389,134 A | 2/1995 | Breton et al. |
| 5,393,461 A | 2/1995 | Fillipova |
| 5,393,821 A | 2/1995 | Shieh et al. |
| 5,395,435 A | 3/1995 | Mizobuchi |
| 5,407,725 A | 4/1995 | Ryoke et al. |
| 5,421,658 A | 6/1995 | Suzuki et al. |
| 5,421,871 A | 6/1995 | Onishi et al. |
| 5,424,780 A | 6/1995 | Cooper |
| 5,428,383 A | 6/1995 | Shields |
| 5,431,501 A | 7/1995 | Hale |
| 5,437,716 A | 8/1995 | Sano et al. |
| 5,441,564 A | 8/1995 | Vogt |
| 5,484,475 A | 1/1996 | Breton |
| 5,484,899 A | 1/1996 | Deitz et al. |
| 5,485,188 A | 1/1996 | Tochihara et al. |
| 5,487,614 A | 1/1996 | Hale |
| 5,488,401 A | 1/1996 | Mochizuki et al. |
| 5,488,402 A | 1/1996 | Shields |
| 5,488,907 A | 2/1996 | Xu |
| 5,503,664 A | 4/1996 | Sano et al. |
| 5,509,140 A | 4/1996 | Koitabashi et al. |
| 5,522,317 A | 6/1996 | Hale |
| 5,522,922 A | 6/1996 | Furusawa |
| 5,529,616 A | 6/1996 | Prasad |
| 5,529,767 A | 6/1996 | Brox et al. |
| 5,531,816 A | 7/1996 | Wickramanayake |
| 5,531,818 A | 7/1996 | Lin |
| 5,534,051 A | 7/1996 | Lauw |
| 5,536,306 A | 7/1996 | Johnson et al. |
| 5,538,548 A | 7/1996 | Yamazaki et al. |
| 5,550,082 A | 8/1996 | Wolfe et al. |
| 5,552,182 A | 9/1996 | Scarpetti |
| 5,554,739 A | 9/1996 | Belmont |
| 5,555,813 A | 9/1996 | Hale |
| 5,559,169 A | 9/1996 | Belmont |
| 5,560,720 A | 10/1996 | Suzuki et al. |
| 5,562,762 A | 10/1996 | Mrvos et al. |
| 5,570,118 A | 10/1996 | Rezanka et al. |
| 5,571,311 A | 11/1996 | Belmont et al. |
| 5,575,845 A | 11/1996 | Belmont et al. |
| 5,575,877 A | 11/1996 | Hale |
| 5,580,372 A | 12/1996 | Gino et al. |
| 5,585,189 A | 12/1996 | Inoue et al. |
| 5,589,522 A | 12/1996 | Beach et al. |
| 5,590,600 A | 1/1997 | Hale |
| 5,591,455 A | 1/1997 | Signorino et al. |
| 5,593,459 A | 1/1997 | Gamblin |
| 5,595,592 A | 1/1997 | Signorino et al. |
| 5,601,023 A | 2/1997 | Hale |
| 5,604,276 A | 2/1997 | Suga |
| 5,609,671 A | 3/1997 | Nagasawa |
| 5,611,847 A | 3/1997 | Guistina et al. |
| 5,615,957 A | 4/1997 | Suzuki et al. |
| 5,621,027 A | 4/1997 | Roschger et al. |
| 5,622,439 A | 4/1997 | Suzuki et al. |
| 5,622,557 A | 4/1997 | Mahmud et al. |
| 5,624,485 A | 4/1997 | Calhoun |
| 5,626,655 A | 5/1997 | Pawlowski et al. |
| 5,630,868 A | 5/1997 | Belmont et al. |
| 5,631,309 A | 5/1997 | Yanagi et al. |
| 5,640,180 A | 6/1997 | Hale |
| 5,642,141 A | 6/1997 | Hale |
| 5,644,988 A | 7/1997 | Xu |
| 5,647,896 A | 7/1997 | Nishimura et al. |
| 5,647,897 A | 7/1997 | Ouki et al. |
| 5,648,405 A | 7/1997 | Ma |
| 5,656,071 A | 8/1997 | Kappele |
| 5,658,376 A | 8/1997 | Noguchi et al. |
| 5,665,150 A | 9/1997 | Schwarz |
| 5,667,569 A | 9/1997 | Fujioka |
| 5,667,571 A | 9/1997 | Ono et al. |
| 5,667,572 A | 9/1997 | Taniguchi |
| 5,672,198 A | 9/1997 | Belmont |
| 5,679,143 A | 10/1997 | Looman |
| 5,686,508 A | 11/1997 | Shimomura |
| 5,686,633 A | 11/1997 | Vieira |
| 5,688,311 A | 11/1997 | Adamic |
| 5,690,721 A | 11/1997 | Itoh |
| 5,690,722 A | 11/1997 | Pawlowski |
| 5,690,723 A | 11/1997 | Sano et al. |
| 5,693,126 A | 12/1997 | Ito |
| 5,698,016 A | 12/1997 | Adams et al. |
| 5,700,317 A | 12/1997 | Adamic |
| 5,704,969 A | 1/1998 | Kanaya |
| 5,707,432 A | 1/1998 | Adams et al. |
| 5,709,976 A | 1/1998 | Malhotra |
| 5,713,988 A | 2/1998 | Belmont |
| 5,713,989 A | 2/1998 | Wickramanayake |
| 5,713,992 A | 2/1998 | Satoh et al. |
| 5,714,538 A | 2/1998 | Beach et al. |
| 5,718,746 A | 2/1998 | Nagasawa et al. |
| 5,719,204 A | 2/1998 | Beach et al. |
| 5,721,344 A | 2/1998 | Baettig |
| 5,725,641 A | 3/1998 | MacLeod |
| 5,725,643 A | 3/1998 | Higashiyama |
| 5,725,644 A | 3/1998 | Sano et al. |
| 5,730,790 A | 3/1998 | Rehman |
| 5,734,396 A | 3/1998 | Hale |
| 5,734,403 A | 3/1998 | Suga et al. |
| 5,735,941 A | 4/1998 | Feeman et al. |
| 5,745,140 A | 4/1998 | Stoffel et al. |
| 5,746,816 A | 5/1998 | Xu |
| 5,746,817 A | 5/1998 | Katsen et al. |
| 5,746,818 A | 5/1998 | Yatake |
| 5,747,562 A | 5/1998 | Mahmud et al. |
| 5,749,950 A | 5/1998 | Mahmud et al. |
| 5,749,951 A | 5/1998 | Yoshiike et al. |
| 5,749,952 A | 5/1998 | Tsang |
| 5,750,592 A | 5/1998 | Shinozuka et al. |
| 5,751,320 A | 5/1998 | Scheffelin et al. |
| 5,766,327 A | 6/1998 | Maze |
| 5,769,930 A | 6/1998 | Sano |
| 5,772,742 A | 6/1998 | Wang |
| 5,777,648 A | 7/1998 | Scheffelin et al. |
| 5,785,743 A | 7/1998 | Adamic et al. |
| 5,786,436 A | 7/1998 | Fischer et al. |
| 5,788,754 A | 8/1998 | Deardurff et al. |
| 5,795,375 A | 8/1998 | Yamazaki et al. |
| 5,803,958 A | 9/1998 | Katsen et al. |
| 5,803,959 A | 9/1998 | Johnson |
| 5,814,138 A | 9/1998 | Fague |
| 5,814,683 A | 9/1998 | Branham |
| 5,814,685 A | 9/1998 | Satake et al. |
| 5,821,283 A | 10/1998 | Hesler |
| 5,825,387 A | 10/1998 | Cowger et al. |
| 5,830,263 A | 11/1998 | Hale |
| 5,830,264 A | 11/1998 | Fujioka et al. |
| 5,830,265 A | 11/1998 | Tsang et al. |
| 5,830,930 A | 11/1998 | Mahmud et al. |
| 5,837,043 A | 11/1998 | Wong et al. |
| 5,837,045 A | 11/1998 | Johnson |
| 5,837,374 A | 11/1998 | Hirayama et al. |
| 5,846,306 A | 12/1998 | Kubota |
| 5,846,307 A | 12/1998 | Nagasawa et al. |
| 5,849,067 A | 12/1998 | Tsuchiya et al. |
| 5,851,274 A | 12/1998 | Lin |
| 5,851,280 A | 12/1998 | Belmont et al. |
| 5,853,465 A | 12/1998 | Tsang |
| 5,854,307 A | 12/1998 | Kimura |

(56) References Cited

U.S. PATENT DOCUMENTS

| | | |
|---|---|---|
| 5,854,331 A | 12/1998 | Ma |
| 5,858,075 A | 1/1999 | Deardurff et al. |
| 5,858,078 A | 1/1999 | Andes et al. |
| 5,861,447 A | 1/1999 | Nagasawa et al. |
| 5,863,323 A | 1/1999 | Mahmud et al. |
| 5,868,823 A | 2/1999 | Yamazaki et al. |
| 5,869,550 A | 2/1999 | Mahmud |
| 5,871,572 A | 2/1999 | Marritt |
| 5,874,974 A | 2/1999 | Courian et al. |
| 5,876,491 A | 3/1999 | Gunn et al. |
| 5,877,100 A | 3/1999 | Smith et al. |
| 5,877,238 A | 3/1999 | Mahmud et al. |
| 5,877,253 A | 3/1999 | Matta et al. |
| 5,885,335 A | 3/1999 | Adams |
| 5,885,336 A | 3/1999 | Kitahara et al. |
| 5,886,065 A | 3/1999 | Tsang et al. |
| 5,891,232 A | 4/1999 | Moffatt |
| 5,891,934 A | 4/1999 | Moffatt et al. |
| 5,895,522 A | 4/1999 | Belmont et al. |
| 5,897,694 A | 4/1999 | Woolf |
| 5,897,961 A | 4/1999 | Malhotra |
| 5,898,445 A | 4/1999 | Becker et al. |
| 5,900,029 A | 5/1999 | Belmont et al. |
| 5,904,762 A | 5/1999 | Mahmud |
| 5,911,816 A | 6/1999 | Gore |
| 5,916,934 A | 6/1999 | Mahmud et al. |
| 5,916,956 A | 6/1999 | Wang et al. |
| 5,919,293 A | 7/1999 | Moffatt et al. |
| 5,919,841 A | 7/1999 | Mahmud et al. |
| 5,919,855 A | 7/1999 | Reed |
| 5,922,118 A | 7/1999 | Johnson |
| 5,925,176 A | 7/1999 | Rehman |
| 5,928,419 A | 7/1999 | Uemura et al. |
| 5,932,631 A | 8/1999 | Marritt |
| 5,935,309 A | 8/1999 | Moffatt et al. |
| 5,938,829 A | 8/1999 | Higashiyama et al. |
| 5,946,012 A | 8/1999 | Courian et al. |
| 5,948,150 A | 9/1999 | Lin |
| 5,948,835 A | 9/1999 | Mahmud et al. |
| 5,951,749 A | 9/1999 | Krepski et al. |
| 5,952,481 A | 9/1999 | Markham |
| 5,955,232 A | 9/1999 | Little |
| 5,955,515 A | 9/1999 | Kimura et al. |
| 5,958,999 A | 9/1999 | Bates et al. |
| 5,961,703 A | 10/1999 | Fraas |
| 5,963,238 A | 10/1999 | Scheffelin et al. |
| 5,965,196 A | 10/1999 | Sawada |
| 5,966,156 A | 10/1999 | Scheffelin et al. |
| 5,968,243 A | 10/1999 | Belmont |
| 5,968,244 A | 10/1999 | Ueda et al. |
| 5,969,003 A | 10/1999 | Foucher et al. |
| 5,972,083 A | 10/1999 | Iijima |
| 5,976,232 A | 11/1999 | Gore |
| 5,976,233 A | 11/1999 | Osumi et al. |
| 5,977,213 A | 11/1999 | Mahmud |
| 5,981,623 A | 11/1999 | McCain et al. |
| 5,985,015 A | 11/1999 | Kanaya |
| 5,985,016 A | 11/1999 | Tsang |
| 5,990,202 A | 11/1999 | Nguyen |
| 6,004,389 A | 12/1999 | Yatake |
| 6,007,611 A | 12/1999 | Mheidle et al. |
| 6,008,272 A | 12/1999 | Mahmud et al. |
| 6,013,123 A | 1/2000 | Scarpetti |
| 6,015,454 A | 1/2000 | Lacroix et al. |
| 6,017,980 A | 1/2000 | Wang |
| 6,019,828 A | 2/2000 | Rehman |
| 6,020,397 A | 2/2000 | Matzinger |
| 6,022,908 A | 2/2000 | Ma |
| 6,024,786 A | 2/2000 | Gore |
| 6,028,137 A | 2/2000 | Mahmud et al. |
| 6,034,153 A | 3/2000 | Tsang et al. |
| 6,036,759 A | 3/2000 | Wickramanayake |
| 6,039,796 A | 3/2000 | Kubota |
| 6,042,643 A | 3/2000 | Belmont et al. |
| 6,050,671 A | 4/2000 | Rotering |
| 6,054,238 A | 4/2000 | Little |
| 6,056,812 A | 5/2000 | Lin |
| 6,057,387 A | 5/2000 | Mahmud |
| 6,068,688 A | 5/2000 | Whitehouse et al. |
| 6,069,190 A | 5/2000 | Bates |
| 6,074,042 A | 6/2000 | Gasvoda et al. |
| 6,083,315 A | 7/2000 | Nakamura et al. |
| 6,086,197 A | 7/2000 | Kubota et al. |
| 6,086,198 A | 7/2000 | Shields |
| 6,089,687 A | 7/2000 | Helterline |
| 6,099,632 A | 8/2000 | Nagasawa et al. |
| 6,100,315 A | 8/2000 | Kitamura et al. |
| 6,102,996 A | 8/2000 | Parazak |
| 6,103,041 A | 8/2000 | Wagner et al. |
| 6,103,380 A | 8/2000 | Devonport |
| 6,103,782 A | 8/2000 | Mizobuchi |
| 6,105,502 A | 8/2000 | Wagner et al. |
| 6,107,350 A | 8/2000 | Boes et al. |
| 6,110,266 A | 8/2000 | Gonzalez-Blanco et al. |
| 6,110,994 A | 8/2000 | Cooke et al. |
| 6,116,409 A | 9/2000 | Yokajty |
| 6,120,594 A | 9/2000 | Curtis et al. |
| 6,124,376 A | 9/2000 | Nichols et al. |
| 6,126,731 A | 10/2000 | Kemeny |
| 6,132,021 A | 10/2000 | Smith |
| 6,132,502 A | 10/2000 | Yatake |
| 6,136,286 A | 10/2000 | Okuyama et al. |
| 6,137,502 A | 10/2000 | Anderson et al. |
| 6,139,139 A | 10/2000 | Stoffel et al. |
| 6,142,621 A | 11/2000 | Romano |
| 6,149,327 A | 11/2000 | Ward et al. |
| 6,150,433 A | 11/2000 | Tsang et al. |
| 6,150,453 A | 11/2000 | Mahmud et al. |
| 6,152,038 A | 11/2000 | Wagner et al. |
| 6,169,129 B1 | 1/2001 | Mahmud et al. |
| 6,172,154 B1 | 1/2001 | Brown |
| 6,174,354 B1 | 1/2001 | Takizawa et al. |
| 6,176,629 B1 | 1/2001 | Suzuki et al. |
| 6,177,498 B1 | 1/2001 | Rehman |
| 6,180,691 B1 | 1/2001 | Cheng et al. |
| 6,184,268 B1 | 2/2001 | Nichols et al. |
| 6,187,086 B1 | 2/2001 | Rehman |
| 6,193,364 B1 | 2/2001 | Iida |
| 6,197,274 B1 | 3/2001 | Mahmud et al. |
| 6,206,517 B1 | 3/2001 | Kovacs et al. |
| 6,207,719 B1 | 3/2001 | Pardikes |
| 6,209,998 B1 | 4/2001 | Yue |
| 6,211,279 B1 | 4/2001 | Mahmud |
| 6,214,100 B1 | 4/2001 | Parazak et al. |
| 6,218,067 B1 | 4/2001 | Belmont |
| 6,221,141 B1 | 4/2001 | Takada et al. |
| 6,221,142 B1 | 4/2001 | Wang et al. |
| 6,221,143 B1 | 4/2001 | Palumbo |
| 6,221,932 B1 | 4/2001 | Moffatt et al. |
| 6,224,202 B1 | 5/2001 | Romano, Jr. |
| 6,231,655 B1 | 5/2001 | Marritt |
| 6,239,193 B1 | 5/2001 | Cheng |
| H1967 H | 6/2001 | Woolf |
| 6,241,811 B1 | 6/2001 | Sano |
| 6,242,529 B1 | 6/2001 | Marritt |
| 6,244,687 B1 | 6/2001 | Gast et al. |
| 6,247,808 B1 | 6/2001 | Ma |
| 6,258,864 B1 | 7/2001 | Dalton et al. |
| 6,264,301 B1 | 7/2001 | Helterline |
| 6,271,285 B1 | 8/2001 | Miyabayashi et al. |
| 6,276,791 B1 | 8/2001 | Kovacs et al. |
| 6,277,183 B1 | 8/2001 | Johnson et al. |
| 6,277,184 B1 | 8/2001 | Kato |
| 6,280,512 B1 | 8/2001 | Botros |
| 6,280,513 B1 | 8/2001 | Osumi et al. |
| 6,280,516 B1 | 8/2001 | Lucchi et al. |
| 6,280,871 B1 | 8/2001 | Tosco et al. |
| 6,281,267 B2 | 8/2001 | Parazak |
| 6,281,917 B1 | 8/2001 | Katsuragi et al. |
| 6,284,029 B1 | 9/2001 | Sano |
| 6,291,572 B1 | 9/2001 | Brown et al. |
| 6,299,675 B1 | 10/2001 | Ono |
| 6,300,391 B2 | 10/2001 | Parazak |
| 6,306,204 B1 | 10/2001 | Lin |

(56) References Cited

U.S. PATENT DOCUMENTS

| | | | |
|---|---|---|---|
| 6,312,103 B1 | 11/2001 | Haluzak | |
| 6,314,574 B1 | 11/2001 | Chan et al. | |
| 6,323,257 B1 | 11/2001 | Moffatt et al. | |
| 6,323,258 B1 | 11/2001 | Lin | |
| 6,323,273 B1 | 11/2001 | Mahmud et al. | |
| 6,328,894 B1 | 12/2001 | Chan et al. | |
| 6,332,919 B2 | 12/2001 | Osumi et al. | |
| 6,336,965 B1 | 1/2002 | Johnson et al. | |
| 6,337,358 B1 | 1/2002 | Whitehouse et al. | |
| 6,341,856 B1 | 1/2002 | Thompson et al. | |
| 6,342,094 B1 | 1/2002 | Kabalnov | |
| 6,342,095 B1 | 1/2002 | Takizawa et al. | |
| 6,348,939 B1 | 2/2002 | Xu | |
| 6,350,519 B1 | 2/2002 | Devonport | |
| 6,352,341 B2 | 3/2002 | Kovacs et al. | |
| 6,354,693 B1 | 3/2002 | Looman et al. | |
| 6,361,156 B1 | 3/2002 | Romano, Jr. et al. | |
| 6,364,472 B1 | 4/2002 | Barinaga et al. | |
| 6,364,944 B1 | 4/2002 | Mahmud et al. | |
| 6,367,922 B2 | 4/2002 | Romano, Jr. | |
| 6,368,239 B1 | 4/2002 | Devonport et al. | |
| 6,372,329 B1 | 4/2002 | Graczyk et al. | |
| 6,372,818 B1 | 4/2002 | Kimura et al. | |
| 6,372,820 B1 | 4/2002 | Devonport | |
| 6,375,317 B1 | 4/2002 | Osumi et al. | |
| 6,379,443 B1 | 4/2002 | Komatsu et al. | |
| 6,383,274 B1 | 5/2002 | Lin | |
| 6,383,275 B1 | 5/2002 | Lin | |
| 6,386,695 B1 | 5/2002 | Kowalski | |
| 6,387,168 B1 | 5/2002 | Koitabashi et al. | |
| 6,387,500 B1 | 5/2002 | Behl | |
| 6,391,947 B1 | 5/2002 | Noguchi et al. | |
| 6,398,858 B1 | 6/2002 | Yu et al. | |
| 6,399,029 B1 | 6/2002 | Porteous | |
| 6,399,202 B1 | 6/2002 | Yu | |
| 6,399,674 B1 | 6/2002 | Kashiwazaki et al. | |
| 6,402,313 B1 | 6/2002 | Xu et al. | |
| 6,402,825 B1 | 6/2002 | Sun | |
| 6,406,143 B1 | 6/2002 | Chen et al. | |
| 6,406,528 B1 | 6/2002 | Macholdt et al. | |
| 6,412,935 B1 | 7/2002 | Doumaux | |
| 6,417,249 B1 | 7/2002 | Nguyen | |
| 6,419,732 B1* | 7/2002 | Matsumura et al. | 106/31.75 |
| 6,419,733 B1 | 7/2002 | Sano et al. | |
| 6,423,375 B1 | 7/2002 | Bi et al. | |
| 6,425,331 B1 | 7/2002 | Xu | |
| 6,425,662 B1 | 7/2002 | Teraoka et al. | |
| 6,431,677 B1 | 8/2002 | Anderson et al. | |
| 6,432,194 B2 | 8/2002 | Johnson et al. | |
| 6,432,523 B1 | 8/2002 | Ma et al. | |
| 6,435,240 B1 | 8/2002 | Fagebaume et al. | |
| 6,435,659 B1 | 8/2002 | Bruinsma | |
| 6,436,178 B1 | 8/2002 | Hosmer | |
| 6,439,710 B1 | 8/2002 | Hale | |
| 6,444,017 B1 | 9/2002 | Yue | |
| 6,444,294 B1 | 9/2002 | Malhotra et al. | |
| 6,447,629 B1 | 9/2002 | Thompson et al. | |
| 6,448,309 B2 | 9/2002 | Mahmud et al. | |
| 6,450,098 B1 | 9/2002 | Hale | |
| 6,450,632 B1 | 9/2002 | Tsang | |
| 6,451,098 B1 | 9/2002 | Lye et al. | |
| 6,451,103 B1 | 9/2002 | Uemura et al. | |
| 6,451,379 B1 | 9/2002 | Tsao | |
| 6,454,403 B1 | 9/2002 | Takada et al. | |
| 6,454,846 B2 | 9/2002 | Yatake | |
| 6,458,195 B1 | 10/2002 | Stoffel et al. | |
| 6,458,458 B1 | 10/2002 | Cooke et al. | |
| 6,460,987 B1 | 10/2002 | Katsuragi et al. | |
| 6,460,989 B1 | 10/2002 | Yano et al. | |
| 6,461,418 B1 | 10/2002 | Yue et al. | |
| 6,464,334 B2 | 10/2002 | Lopez et al. | |
| 6,467,896 B2 | 10/2002 | Meyer | |
| 6,468,340 B1 | 10/2002 | Moffatt | |
| 6,468,342 B1 | 10/2002 | Itoh et al. | |
| 6,471,757 B1 | 10/2002 | Koitabashi et al. | |
| 6,471,763 B1 | 10/2002 | Karl | |
| 6,472,471 B2 | 10/2002 | Cooke et al. | |
| 6,475,271 B2 | 11/2002 | Lin | |
| 6,475,612 B1 | 11/2002 | Knight et al. | |
| 6,478,863 B2 | 11/2002 | Johnson et al. | |
| 6,478,963 B1 | 11/2002 | Rossmanith | |
| 6,479,571 B1 | 11/2002 | Cooke et al. | |
| 6,485,138 B1 | 11/2002 | Kubota et al. | |
| 6,486,903 B1 | 11/2002 | Wagner et al. | |
| 6,488,370 B2 | 12/2002 | Hale | |
| 6,488,753 B1 | 12/2002 | Ito et al. | |
| 6,491,976 B2 | 12/2002 | Horiuchi et al. | |
| 6,494,943 B1 | 12/2002 | Yu et al. | |
| 6,494,946 B1 | 12/2002 | Belmont et al. | |
| 6,497,479 B1 | 12/2002 | Stoffel et al. | |
| 6,498,222 B1 | 12/2002 | Kitamura et al. | |
| 6,500,248 B1 | 12/2002 | Hayashi | |
| 6,500,880 B1 | 12/2002 | Parazak | |
| 6,502,917 B1 | 1/2003 | Shinada et al. | |
| 6,502,920 B1 | 1/2003 | Anderson et al. | |
| 6,503,307 B1 | 1/2003 | Noguchi | |
| 6,503,308 B2 | 1/2003 | Stramel | |
| 6,503,311 B1 | 1/2003 | Karl et al. | |
| 6,503,317 B1 | 1/2003 | Ortalano | |
| 6,503,978 B1 | 1/2003 | Tsao | |
| 6,505,910 B1 | 1/2003 | Doval | |
| 6,505,929 B1 | 1/2003 | Chow | |
| 6,506,239 B1 | 1/2003 | Osumi | |
| 6,506,240 B2 | 1/2003 | Takemoto | |
| 6,506,245 B1 | 1/2003 | Kinney et al. | |
| 6,508,871 B1 | 1/2003 | Kato | |
| 6,508,872 B2 | 1/2003 | Nguyen | |
| 6,511,534 B1 | 1/2003 | Mishina et al. | |
| 6,514,330 B1 | 2/2003 | Kanaya et al. | |
| 6,514,920 B1 | 2/2003 | Katsuragi et al. | |
| 6,517,199 B1 | 2/2003 | Tomioka et al. | |
| 6,521,034 B1 | 2/2003 | Osumi et al. | |
| 6,522,522 B2 | 2/2003 | Yu | |
| 6,524,383 B2 | 2/2003 | Komatsu et al. | |
| 6,528,148 B2 | 3/2003 | Niu | |
| 6,530,656 B1 | 3/2003 | Teraoka et al. | |
| 6,533,406 B2 | 3/2003 | Katsuragi | |
| 6,533,407 B2 | 3/2003 | Mouri et al. | |
| 6,533,853 B2 | 3/2003 | Mishina | |
| 6,534,569 B2 | 3/2003 | Mahmud et al. | |
| 6,536,878 B2 | 3/2003 | Kasperchik et al. | |
| 6,536,890 B1 | 3/2003 | Kato et al. | |
| 6,537,364 B2 | 3/2003 | Dietz et al. | |
| 6,538,047 B1 | 3/2003 | Miyabayashi | |
| 6,538,049 B1 | 3/2003 | Kappele | |
| 6,540,329 B1 | 4/2003 | Kaneko et al. | |
| 6,540,334 B1 | 4/2003 | Mrvos et al. | |
| 6,540,345 B1 | 4/2003 | Wagner et al. | |
| 6,541,538 B1 | 4/2003 | Matzinger | |
| 6,543,889 B2 | 4/2003 | Murcia et al. | |
| 6,547,381 B2 | 4/2003 | Watanabe et al. | |
| 6,548,572 B1 | 4/2003 | Breck | |
| 6,550,901 B2 | 4/2003 | Iida | |
| 6,550,902 B2 | 4/2003 | Shinada et al. | |
| 6,550,903 B2 | 4/2003 | Katsuragi | |
| 6,551,393 B2 | 4/2003 | Devonport et al. | |
| 6,554,891 B1 | 4/2003 | Momose | |
| 6,562,121 B2 | 5/2003 | Nickel et al. | |
| 6,565,202 B2 | 5/2003 | Rose et al. | |
| 6,572,226 B2 | 6/2003 | Tyvoll | |
| 6,572,690 B2 | 6/2003 | Rehman et al. | |
| 6,572,692 B1 | 6/2003 | Osumi | |
| 6,578,943 B2 | 6/2003 | Arquilevich et al. | |
| 6,582,508 B2 | 6/2003 | Dietz et al. | |
| 6,585,815 B2 | 7/2003 | Koitabashi et al. | |
| 6,585,817 B2 | 7/2003 | Lee | |
| 6,585,818 B2 | 7/2003 | Thakkar et al. | |
| 6,586,501 B1 | 7/2003 | Dalton et al. | |
| 6,588,880 B1 | 7/2003 | Gasvoda et al. | |
| 6,592,657 B2 | 7/2003 | Lee et al. | |
| 6,596,065 B2 | 7/2003 | Ito | |
| 6,596,068 B1 | 7/2003 | Ito et al. | |
| 6,596,378 B2 | 7/2003 | Hanmura et al. | |
| 6,602,333 B2 | 8/2003 | Miyabayashi | |

(56) References Cited

U.S. PATENT DOCUMENTS

| | | |
|---|---|---|
| 6,602,335 B2 | 8/2003 | Moffatt et al. |
| 6,604,809 B2 | 8/2003 | Katsuragi |
| 6,605,420 B2 | 8/2003 | Nakai et al. |
| 6,607,266 B2 | 8/2003 | Katsuragi et al. |
| 6,607,268 B2 | 8/2003 | Bruinsma |
| 6,607,565 B1 | 8/2003 | Herrmann et al. |
| 6,607,589 B2 | 8/2003 | Adamic et al. |
| 6,610,129 B1 | 8/2003 | Sader et al. |
| 6,616,273 B1 | 9/2003 | Bruinsma |
| 6,618,066 B2 | 9/2003 | Hale |
| 6,620,229 B2 | 9/2003 | Doi et al. |
| 6,630,268 B2 | 10/2003 | Tosco et al. |
| 6,631,984 B2 | 10/2003 | Thompson et al. |
| 6,632,275 B1 | 10/2003 | Schoen et al. |
| 6,632,485 B1 | 10/2003 | Tang et al. |
| 6,632,594 B2 | 10/2003 | Nakai et al. |
| 6,637,876 B2 | 10/2003 | Hori |
| 6,638,350 B2 | 10/2003 | Butler et al. |
| 6,641,259 B1 | 11/2003 | Kopolow et al. |
| 6,641,651 B2 | 11/2003 | Suzuki |
| 6,641,653 B2 | 11/2003 | Yu |
| 6,641,656 B2 | 11/2003 | Yu |
| 6,643,220 B2 | 11/2003 | Anderson |
| 6,644,778 B2 | 11/2003 | Rotering |
| 6,648,950 B2 | 11/2003 | Lee |
| 6,648,953 B2 | 11/2003 | Yamazaki et al. |
| 6,648,954 B2 | 11/2003 | Uemura et al. |
| 6,649,317 B2 | 11/2003 | Wagner et al. |
| 6,652,084 B1 | 11/2003 | Teraoka |
| 6,659,582 B2 | 12/2003 | Underwood |
| 6,660,075 B2 | 12/2003 | Bergemann et al. |
| 6,664,312 B2 | 12/2003 | Devonport |
| 6,673,503 B2 | 1/2004 | Wagner et al. |
| 6,679,576 B2 | 1/2004 | Crivelli |
| 6,679,598 B2 | 1/2004 | Kato et al. |
| 6,685,769 B1 | 2/2004 | Karl et al. |
| 6,686,314 B2 | 2/2004 | Xu et al. |
| 6,686,409 B2 | 2/2004 | Mahmud et al. |
| 6,688,737 B2 | 2/2004 | Nagai et al. |
| 6,689,433 B2 | 2/2004 | Niu et al. |
| 6,699,319 B2 | 3/2004 | Adams |
| 6,706,104 B2 | 3/2004 | Takuhara et al. |
| 6,706,105 B2 | 3/2004 | Takada et al. |
| 6,709,506 B2 | 3/2004 | Mahmud et al. |
| 6,715,866 B2 | 4/2004 | Kasperchik |
| 6,716,278 B2 | 4/2004 | Prasad et al. |
| 6,719,420 B2 | 4/2004 | Tomioka et al. |
| 6,720,367 B2 | 4/2004 | Taniguchi et al. |
| 6,722,765 B2 | 4/2004 | Rolly et al. |
| 6,723,161 B2 | 4/2004 | Langenmayr et al. |
| 6,723,783 B2 | 4/2004 | Palumbo et al. |
| 6,730,152 B2 | 5/2004 | Rehman |
| 6,733,120 B2 | 5/2004 | Ogasawara et al. |
| 6,737,449 B1 | 5/2004 | Yatake |
| 6,740,151 B2 | 5/2004 | Belmont et al. |
| 6,740,689 B1 | 5/2004 | Lee et al. |
| 6,749,773 B2 | 6/2004 | Emanuel |
| 6,753,425 B2 | 6/2004 | Nakai et al. |
| 6,759,459 B2 | 7/2004 | Lin |
| 6,761,759 B2 | 7/2004 | Oki et al. |
| 6,767,640 B2 | 7/2004 | Moffatt |
| 6,776,830 B2 | 8/2004 | Marritt |
| 6,777,462 B2 | 8/2004 | Smith et al. |
| 6,779,864 B2 | 8/2004 | Underwood |
| 6,779,884 B1 | 8/2004 | Ma |
| 6,780,389 B2 | 8/2004 | Karl et al. |
| 6,780,901 B1 | 8/2004 | Endo et al. |
| 6,786,957 B2 | 9/2004 | Choy et al. |
| 6,790,268 B2 | 9/2004 | Lee et al. |
| 6,790,878 B2 | 9/2004 | Kurabayashi |
| 6,793,308 B2 | 9/2004 | Sugimoto et al. |
| 6,793,329 B2 | 9/2004 | Batley et al. |
| 6,793,722 B2 | 9/2004 | Chien et al. |
| 6,793,723 B2 | 9/2004 | Auslander et al. |
| 6,794,427 B2 | 9/2004 | Kurabayashi et al. |
| 6,797,347 B2 | 9/2004 | Chow |
| 6,805,736 B2 | 10/2004 | Wickramanayake |
| 6,806,300 B2 | 10/2004 | Waki et al. |
| 6,806,925 B2 | 10/2004 | Ishii et al. |
| 6,808,555 B2 | 10/2004 | Wang |
| 6,808,583 B2 | 10/2004 | Kwasny et al. |
| 6,811,597 B2 | 11/2004 | Oki et al. |
| 6,814,790 B2 | 11/2004 | Sir et al. |
| 6,814,791 B2 | 11/2004 | Moore |
| 6,814,792 B2 | 11/2004 | Taniguchi |
| 6,814,793 B2 | 11/2004 | Akers et al. |
| 6,818,048 B2 | 11/2004 | Prasad et al. |
| 6,820,972 B2 | 11/2004 | Kinalski |
| 6,821,328 B2 | 11/2004 | Tomioka et al. |
| 6,821,330 B1 | 11/2004 | Sano |
| 6,822,781 B1 | 11/2004 | Amici et al. |
| 6,824,263 B2 | 11/2004 | Taniguchi et al. |
| 6,827,403 B2 | 12/2004 | Paasche et al. |
| 6,827,434 B1 | 12/2004 | Katsuragi et al. |
| 6,827,768 B2 | 12/2004 | Andrievsky et al. |
| 6,830,326 B2 | 12/2004 | Tsao |
| 6,830,327 B2 | 12/2004 | Asakawa |
| 6,830,927 B2 | 12/2004 | Rao |
| 6,832,830 B2 | 12/2004 | Seino |
| 6,833,026 B2 | 12/2004 | Palumbo |
| 6,834,945 B2 | 12/2004 | Ishizawa et al. |
| H2113 H | 1/2005 | Nichols et al. |
| 6,840,614 B2 | 1/2005 | Wagner et al. |
| 6,843,838 B2 | 1/2005 | Zimmer et al. |
| 6,844,035 B2 | 1/2005 | Niu et al. |
| 6,848,779 B2 | 2/2005 | Lo et al. |
| 6,848,781 B2 | 2/2005 | Ogino et al. |
| 6,849,111 B2 | 2/2005 | Suzuki |
| 6,851,787 B2 | 2/2005 | Johnson |
| 6,852,153 B2 | 2/2005 | Uhlir-Tsang |
| 6,852,156 B2 | 2/2005 | Yeh et al. |
| 6,855,193 B2 | 2/2005 | Andrievsky et al. |
| 6,858,301 B2 | 2/2005 | Ganapathiappan |
| 6,860,593 B2 | 3/2005 | Kashiwazaki et al. |
| 6,863,719 B2 | 3/2005 | Butler et al. |
| 6,866,378 B2 | 3/2005 | Wotton et al. |
| 6,866,381 B2 | 3/2005 | Kelly-Rowley et al. |
| 6,866,707 B2 | 3/2005 | Kato |
| 6,867,286 B1 | 3/2005 | Holloway |
| 6,869,470 B2 | 3/2005 | Kato |
| 6,869,647 B2 | 3/2005 | Page |
| 6,871,929 B2 | 3/2005 | Crivelli et al. |
| 6,872,430 B2 | 3/2005 | Burch et al. |
| 6,887,640 B2 | 5/2005 | Zhang et al. |
| 6,896,647 B1 | 5/2005 | Karger |
| 6,899,754 B2 | 5/2005 | Yeh |
| 6,908,185 B2 | 6/2005 | Chen |
| 6,911,073 B2 | 6/2005 | Adams et al. |
| 6,916,088 B2 | 7/2005 | Smith et al. |
| 6,916,089 B2 | 7/2005 | Iida |
| 6,916,367 B2 | 7/2005 | Palumbo |
| 6,921,429 B2 | 7/2005 | Sago et al. |
| 6,921,433 B2 | 7/2005 | Kuribayashi et al. |
| 6,935,717 B2 | 8/2005 | Su et al. |
| 6,945,644 B2 | 9/2005 | Kabalnov |
| 6,948,021 B2 | 9/2005 | Derrico |
| 6,948,804 B2 | 9/2005 | Iida |
| 6,953,239 B2 | 10/2005 | Gondek et al. |
| 6,955,422 B2 | 10/2005 | Miyazawa et al. |
| 6,961,076 B2 | 11/2005 | Wagner |
| 6,964,702 B2 | 11/2005 | Shen et al. |
| 6,966,643 B2 | 11/2005 | Hale |
| 6,969,159 B2 | 11/2005 | Su et al. |
| RE38,952 E | 1/2006 | Hale et al. |
| 6,988,796 B2 | 1/2006 | Rolly et al. |
| 6,991,329 B2 | 1/2006 | Gore |
| 6,991,676 B2 | 1/2006 | Kabalnov et al. |
| 6,997,979 B2 | 2/2006 | Bauer |
| 7,001,649 B2 | 2/2006 | Wagner et al. |
| 7,001,660 B2 | 2/2006 | Garitano |
| 7,001,936 B2 | 2/2006 | Akers, Jr. et al. |
| 7,005,003 B2 | 2/2006 | Mott |
| 7,005,461 B2 | 2/2006 | Sanada et al. |
| 7,008,053 B2 | 3/2006 | Hashii et al. |

(56) References Cited

U.S. PATENT DOCUMENTS

| | | | |
|---|---|---|---|
| 7,008,977 B2 | 3/2006 | Sakai et al. |
| 7,011,397 B2 | 3/2006 | Miyazawa et al. |
| 7,018,030 B2 | 3/2006 | Seino et al. |
| 7,018,953 B2 | 3/2006 | Gore et al. |
| 7,025,813 B2 | 4/2006 | Vanmaele et al. |
| 7,025,820 B2 | 4/2006 | Champlin et al. |
| 7,027,185 B2 | 4/2006 | Subirada et al. |
| 7,030,174 B2 | 4/2006 | Yatake |
| 7,030,175 B2 | 4/2006 | Vincent |
| 7,033,423 B2 | 4/2006 | Rolly |
| 7,034,149 B2 | 4/2006 | Hirokazu et al. |
| 7,034,273 B1 | 4/2006 | O |
| 7,037,398 B2 | 5/2006 | Kwasny et al. |
| 7,041,424 B2 | 5/2006 | Xu |
| 7,045,002 B2 | 5/2006 | Bauer et al. |
| 7,046,389 B2 | 5/2006 | Lopez et al. |
| 7,049,039 B2 | 5/2006 | Tazawa et al. |
| 7,052,535 B2 | 5/2006 | Uhlir-Tsang et al. |
| 7,056,962 B2 | 6/2006 | Johnson et al. |
| 7,058,339 B2 | 6/2006 | Wilcox |
| 7,066,590 B2 | 6/2006 | Lee et al. |
| 7,074,843 B2 | 7/2006 | Nakamura et al. |
| 7,086,732 B2 | 8/2006 | Kasperchik |
| 7,090,719 B2 | 8/2006 | Ishikawa et al. |
| 7,097,275 B2 | 8/2006 | Murcia |
| 7,112,629 B2 | 9/2006 | Niu et al. |
| 7,115,675 B2 | 10/2006 | Schut |
| 7,119,133 B2 | 10/2006 | Vincent |
| 7,125,100 B2 | 10/2006 | Ishizawa et al. |
| 7,129,284 B2 | 10/2006 | Ma |
| 7,148,182 B2 | 12/2006 | Field et al. |
| 7,150,522 B2 | 12/2006 | Sen |
| 7,152,965 B2 | 12/2006 | Ishizawa et al. |
| 7,157,504 B2 | 1/2007 | Ma et al. |
| 7,159,975 B2 | 1/2007 | Yue |
| 7,163,577 B2 | 1/2007 | Tyrell |
| 7,165,836 B2 | 1/2007 | Ahlvin et al. |
| 7,173,078 B2 | 2/2007 | Lamprey et al. |
| 7,204,872 B2 | 4/2007 | Uhlir-Tsang |
| 7,204,873 B2 | 4/2007 | Bauer |
| 7,214,260 B2 | 5/2007 | Doi et al. |
| 7,217,315 B2 | 5/2007 | Bauer |
| 7,220,303 B2 | 5/2007 | Tyvoll |
| 7,220,304 B2 | 5/2007 | Momose et al. |
| 7,220,528 B2 | 5/2007 | Ganapathiappan |
| 7,221,878 B2 | 5/2007 | Chen |
| 7,241,334 B2 | 7/2007 | Srinivas |
| 7,247,195 B2 | 7/2007 | Dodge et al. |
| 7,253,216 B2 | 8/2007 | Miyabayashi |
| 7,264,662 B2 | 9/2007 | Dodge et al. |
| 7,294,183 B2 | 11/2007 | Tyvoll |
| 7,294,185 B2 | 11/2007 | Belmont et al. |
| 7,297,202 B2 | 11/2007 | Ichinose et al. |
| 7,314,273 B2 | 1/2008 | Robertson et al. |
| 7,355,044 B2 | 4/2008 | Vanmaele et al. |
| 7,390,441 B2 | 6/2008 | Bollepalli |
| 7,393,403 B2 | 7/2008 | Lee et al. |
| 7,413,683 B2 | 8/2008 | Bollepalli |
| 7,416,587 B2 | 8/2008 | Kondo |
| 7,416,594 B2 | 8/2008 | Moffatt |
| 7,416,597 B2 | 8/2008 | Rehman |
| 7,497,563 B2 | 3/2009 | Rehman |
| 7,906,590 B2 | 3/2011 | Lee et al. |
| 7,964,033 B2 * | 6/2011 | Sujeeth et al. ............ 106/493 |
| 8,118,924 B2 * | 2/2012 | Sujeeth et al. ............ 106/506 |
| 8,226,761 B2 * | 7/2012 | Sujeeth et al. ............ 106/499 |
| 2001/0018472 A1 | 8/2001 | Parazak et al. |
| 2001/0031422 A1 | 10/2001 | Iwasaki |
| 2002/0005146 A1 | 1/2002 | Palumbo et al. |
| 2002/0088375 A1 | 7/2002 | Komatsu et al. |
| 2002/0130938 A1 | 9/2002 | Kowalski |
| 2002/0144626 A1 | 10/2002 | Schut |
| 2002/0158952 A1 | 10/2002 | Adachi et al. |
| 2002/0195022 A1 | 12/2002 | Moffatt et al. |
| 2003/0019398 A1 | 1/2003 | Komatsu et al. |
| 2003/0019529 A1 | 1/2003 | Reinelt |
| 2003/0024434 A1 | 2/2003 | Butler et al. |
| 2003/0038869 A1 | 2/2003 | Kaneko et al. |
| 2003/0164114 A1 | 9/2003 | Kitayama et al. |
| 2003/0205171 A1 | 11/2003 | Adams et al. |
| 2003/0209166 A1 | 11/2003 | Vanmaele et al. |
| 2004/0006157 A1 | 1/2004 | Gloster et al. |
| 2004/0020407 A1 | 2/2004 | Kato et al. |
| 2004/0035323 A1 | 2/2004 | Suzuki et al. |
| 2004/0074018 A1 | 4/2004 | Wuzik et al. |
| 2004/0092647 A1 | 5/2004 | Chauvin |
| 2004/0103822 A1 | 6/2004 | Champlin |
| 2004/0169165 A1 | 9/2004 | Srinivas |
| 2004/0201658 A1 | 10/2004 | Jackson et al. |
| 2004/0229974 A1 | 11/2004 | Miyabayashi |
| 2004/0252162 A1 | 12/2004 | Gondek et al. |
| 2004/0252173 A1 * | 12/2004 | Ben-Zur et al. ............ 347/101 |
| 2005/0020728 A1 | 1/2005 | Nagasawa et al. |
| 2005/0129015 A1 | 6/2005 | Jamieson et al. |
| 2005/0171238 A1 | 8/2005 | Bauer et al. |
| 2005/0171239 A1 | 8/2005 | Bauer et al. |
| 2005/0171240 A1 | 8/2005 | Bauer et al. |
| 2005/0183629 A1 | 8/2005 | McCain |
| 2005/0187312 A1 | 8/2005 | Akers, Jr. et al. |
| 2005/0190244 A1 | 9/2005 | Tyrell |
| 2005/0199152 A1 | 9/2005 | Hale et al. |
| 2005/0199155 A1 | 9/2005 | Lauw et al. |
| 2005/0204957 A1 | 9/2005 | Momose et al. |
| 2005/0223938 A1 | 10/2005 | Tyvoll |
| 2006/0004790 A1 | 1/2006 | Brown et al. |
| 2006/0070549 A1 | 4/2006 | Jung et al. |
| 2006/0071992 A1 | 4/2006 | Sarkisian et al. |
| 2006/0135361 A1 | 6/2006 | Markel et al. |
| 2006/0150345 A1 | 7/2006 | Mazza |
| 2006/0162612 A1 | 7/2006 | Kabalnov et al. |
| 2006/0176349 A1 | 8/2006 | Nagai et al. |
| 2006/0189717 A1 | 8/2006 | Johnson et al. |
| 2006/0201380 A1 | 9/2006 | Kowalski |
| 2006/0211790 A1 | 9/2006 | Dimotakis et al. |
| 2006/0211791 A1 | 9/2006 | Burns et al. |
| 2007/0100024 A1 * | 5/2007 | Gu et al. ............ 523/160 |
| 2007/0154821 A1 | 7/2007 | Galloway et al. |
| 2007/0277699 A1 | 12/2007 | Bauer |
| 2007/0289072 A1 | 12/2007 | Mazza |
| 2008/0047462 A1 | 2/2008 | Klein et al. |
| 2008/0115695 A1 | 5/2008 | Sujeeth et al. |
| 2008/0119613 A1 | 5/2008 | Klein et al. |
| 2008/0121138 A1 | 5/2008 | Kennedy et al. |
| 2008/0152808 A1 | 6/2008 | Kabalnov et al. |
| 2008/0308002 A1 | 12/2008 | Moffatt |
| 2009/0050014 A1 | 2/2009 | Sujeeth et al. |
| 2009/0111917 A1 | 4/2009 | Bonora |
| 2009/0192248 A1 | 7/2009 | Palumbo et al. |
| 2010/0061951 A1 | 3/2010 | Sujeeth et al. |
| 2010/0271418 A1 | 10/2010 | Shimomura et al. |
| 2011/0239903 A1 | 10/2011 | Sujeeth et al. |

FOREIGN PATENT DOCUMENTS

| | | |
|---|---|---|
| CA | 2207414 | 6/1996 |
| CA | 2258188 | 12/1997 |
| CN | 1275150 | 11/2000 |
| CN | 1665892 | 9/2005 |
| DE | 4215367 | 11/1993 |
| DE | 19618564 | 11/1997 |
| DE | 19823866 | 2/1999 |
| DE | 19831869 | 1/2000 |
| DE | 102005010468 | 9/2006 |
| EP | 0475075 | 3/1992 |
| EP | 0688836 | 12/1995 |
| EP | 0710706 | 5/1996 |
| EP | 0761783 | 3/1997 |
| EP | 0778798 | 6/1997 |
| EP | 0834537 | 4/1998 |
| EP | 0894835 | 3/1999 |
| EP | 0960911 | 12/1999 |
| EP | 1045014 | 10/2000 |
| EP | 1061107 | 12/2000 |
| EP | 1132439 | 9/2001 |

(56) References Cited

FOREIGN PATENT DOCUMENTS

| | | |
|---|---|---|
| EP | 1243625 | 9/2002 |
| EP | 1418209 | 5/2004 |
| EP | 1469042 | 10/2004 |
| EP | 1533347 | 5/2005 |
| EP | 1616913 | 1/2006 |
| EP | 1616915 | 1/2006 |
| EP | 1681320 | 7/2006 |
| FR | 2672307 | 8/1992 |
| GB | 668724 | 3/1948 |
| GB | 688776 | 3/1953 |
| GB | 788195 | 12/1957 |
| GB | 916132 | 1/1963 |
| GB | 1348850 | 3/1974 |
| GB | 1386543 | 3/1975 |
| GB | 1527396 | 10/1978 |
| GB | 1537379 | 12/1978 |
| JP | 59122555 | 7/1984 |
| JP | 59184161 | 10/1984 |
| JP | 60115665 | 6/1985 |
| JP | 3279369 | 12/1991 |
| JP | 5255607 | 10/1993 |
| JP | 6128517 | 5/1994 |
| JP | 7258578 | 10/1995 |
| JP | 8003498 | 1/1996 |
| JP | 8283596 | 10/1996 |
| JP | 10036726 | 2/1998 |
| JP | 10036727 | 2/1998 |
| JP | 10067957 | 3/1998 |
| JP | 10110110 | 4/1998 |
| JP | 10110111 | 4/1998 |
| JP | 10110112 | 4/1998 |
| JP | 10110114 | 4/1998 |
| JP | 10120958 | 5/1998 |
| JP | 10195331 | 7/1998 |
| JP | 10195360 | 7/1998 |
| JP | 10237349 | 9/1998 |
| JP | 10330665 | 12/1998 |
| JP | 11246806 | 9/1999 |
| JP | 11323175 | 11/1999 |
| JP | 11349312 | 12/1999 |
| JP | 2000053902 | 2/2000 |
| JP | 2000345085 | 12/2000 |
| JP | 2000345086 | 12/2000 |
| JP | 2000345094 | 12/2000 |
| JP | 2000345095 | 12/2000 |
| JP | 2002097236 | 4/2002 |
| JP | 2002220557 | 8/2002 |
| JP | 2003105235 | 4/2003 |
| JP | 2003117995 | 4/2003 |
| JP | 2003246953 | 9/2003 |
| JP | 2004010632 | 1/2004 |
| JP | 2004-277507 | 10/2004 |
| JP | 2005-036129 | 2/2005 |
| JP | 2005048114 | 2/2005 |
| JP | 2005097491 | 4/2005 |
| JP | 2005132985 | 5/2005 |
| JP | 2005349827 | 12/2005 |
| JP | 2006265379 | 10/2006 |
| JP | 2007186681 | 7/2007 |
| JP | 2001214085 | 8/2007 |
| JP | 2008-031356 | 2/2008 |
| WO | WO 92/13983 | 8/1992 |
| WO | WO 93/08237 | 4/1993 |
| WO | WO 93/12939 | 7/1993 |
| WO | WO 94/05732 | 3/1994 |
| WO | WO 96/06729 | 3/1996 |
| WO | WO 96/18688 | 6/1996 |
| WO | WO 96/24636 | 8/1996 |
| WO | WO 99/61529 | 12/1999 |
| WO | WO 99/63007 | 12/1999 |
| WO | WO 00/03609 | 1/2000 |
| WO | WO 00/75246 | 12/2000 |
| WO | WO 01/51566 | 7/2001 |
| WO | WO 01/62862 | 8/2001 |
| WO | 02064680 | 8/2002 |
| WO | WO 02/090448 | 11/2002 |
| WO | WO 02/092680 | 11/2002 |
| WO | WO 03/100884 | 12/2003 |
| WO | WO 2004/011558 | 2/2004 |
| WO | WO 2004/012515 | 2/2004 |
| WO | WO 2004/094537 | 11/2004 |
| WO | WO 2005/028576 | 3/2005 |
| WO | WO 2005/113677 | 12/2005 |
| WO | WO 2006/039034 | 4/2006 |
| WO | WO 2006/066132 | 6/2006 |
| WO | WO 2006/069165 | 6/2006 |
| WO | WO 2006/081299 | 8/2006 |
| WO | WO 2006/086660 | 8/2006 |
| WO | 2007/021731 | 2/2007 |
| WO | WO 2007/057111 | 5/2007 |
| WO | WO 2007/136540 | 11/2007 |
| WO | WO 2008/018873 | 2/2008 |
| WO | WO 2008/049735 | 5/2008 |
| WO | WO 2008/055244 | 5/2008 |
| WO | WO 2008/055245 | 5/2008 |
| WO | WO 2009/026552 | 2/2009 |
| WO | WO 2009/075802 | 6/2009 |
| WO | WO 2010/022377 | 2/2010 |

OTHER PUBLICATIONS

United States Patent Office Action for U.S. Appl. No. 12/545,790 dated Jun. 30, 2011 (7 pages).
"Pentaethylenehexamine 4067-16-7" prepared for NCI to support chemical nomination by Technical Resources International, Inc. under contract No. N02-CB-07007 (10/05; 3/06) 1-23.
Air Products and Chemicals, Inc., "Surfynol Surfactants for Pigment Grinding" (1999) 4 pages.
Air Products and Chemicals, Inc., Material Safety Data Sheet No. 300000004701 for Surfynol® CT-131 Grind Aid (2006) 1-7.
Allinger, N.L. et al., "Organische Chemie," Kapitel 8. Verbindungen mit Carbonyl-Gruppen, Walter deGruyter, Berlin (1980) p. 292.
American Ink Maker (1923-2001) (1996) vol. 44(2):30-2, 34-6, 66.
BASF Corporation, Joncryl® 1163, data sheet (Dec. 5, 2008) 2 pages.
BASF Corporation, Joncryl® 142, data sheet (Dec. 5, 2008) 3 pages.
BASF Corporation, Joncryl® 1536, data sheet (Dec. 5, 2008) 2 pages.
BASF Corporation, Joncryl® 1655, data sheet (Dec. 5, 2008) 4 pages.
BASF Corporation, Joncryl® 1670, data sheet (Dec. 5, 2008) 2 pages.
BASF Corporation, Joncryl® 1680, data sheet (Dec. 5, 2008) 2 pages.
BASF Corporation, Joncryl® 1695, data sheet (Dec. 5, 2008) 2 pages.
BASF Corporation, Joncryl® 2153, data sheet (Dec. 5, 2008) 2 pages.
BASF Corporation, Joncryl® 2350, data sheet (Dec. 12, 2008) 2 pages.
BASF Corporation, Joncryl® 2640, data sheet (Dec. 5, 2008) 2 pages.
BASF Corporation, Joncryl® 2641, data sheet (Nov. 14, 2008) 2 pages.
BASF Corporation, Joncryl® 2646, data sheet (Dec. 5, 2008) 2 pages.
BASF Corporation, Joncryl® 2660, data sheet (Nov. 13, 2008) 3 pages.
BASF Corporation, Joncryl® 2664, data sheet (Dec. 5, 2008) 4 pages.
BASF Corporation, Joncryl® 50, data sheet (Dec. 10, 2008) 2 pages.
BASF Corporation, Joncryl® 537, data sheet (Dec. 10, 2008) 3 pages.
BASF Corporation, Joncryl® 538-A, data sheet (Nov. 14, 2008) 3 pages.
BASF Corporation, Joncryl® 58, data sheet (Dec. 10, 2008) 2 pages.
BASF Corporation, Joncryl® 585, data sheet (Dec. 10, 2008) 2 pages.
BASF Corporation, Joncryl® 60, data sheet (Dec. 11, 2008) 2 pages.
BASF Corporation, Joncryl® 61, data sheet (Dec. 11, 2008) 2 pages.

(56) References Cited

OTHER PUBLICATIONS

BASF Corporation, Joncryl® 611, data sheet (Dec. 11, 2008) 3 pages.
BASF Corporation, Joncryl® 617-A, data sheet (Nov. 13, 2008) 2 pages.
BASF Corporation, Joncryl® 62, data sheet (Dec. 11, 2008) 2 pages.
BASF Corporation, Joncryl® 624, data sheet (Nov. 13, 2008) 2 pages.
BASF Corporation, Joncryl® 63, data sheet (Dec. 11, 2008) 2 pages.
BASF Corporation, Joncryl® 631, data sheet (Dec. 11, 2008) 2 pages.
BASF Corporation, Joncryl® 636, data sheet (Dec. 5, 2008) 2 pages.
BASF Corporation, Joncryl® 646, data sheet (Dec. 11, 2008) 3 pages.
BASF Corporation, Joncryl® 655, data sheet (Dec. 11, 2008) 3 pages.
BASF Corporation, Joncryl® 660, data sheet (Dec. 11, 2008) 3 pages.
BASF Corporation, Joncryl® 67, data sheet (Dec. 11, 2008) 2 pages.
BASF Corporation, Joncryl® 678, data sheet (Dec. 11, 2008) 3 pages.
BASF Corporation, Joncryl® 680, data sheet (Dec. 11, 2008) 2 pages.
BASF Corporation, Joncryl® 682, data sheet (Dec. 11, 2008) 3 pages.
BASF Corporation, Joncryl® 690, data sheet (Dec. 11, 2008) 3 pages.
BASF Corporation, Joncryl® 693, data sheet (Dec. 11, 2008) 3 pages.
BASF Corporation, Joncryl® 74, data sheet.
BASF Corporation, Joncryl® 74-A, data sheet (Nov. 12, 2008) 2 pages.
BASF Corporation, Joncryl® 74-A, data sheet (Dec. 5, 2008) 2 pages.
BASF Corporation, Joncryl® 750, data sheet (Nov. 13, 2008) 3 pages.
BASF Corporation, Joncryl® 77, data sheet (Dec. 11, 2008) 2 pages.
BASF Corporation, Joncryl® 80, data sheet (Nov. 13, 2008) 2 pages.
BASF Corporation, Joncryl® 89, data sheet (Dec. 11, 2008) 2 pages.
BASF Corporation, Joncryl® 9010, preliminary data sheet (Jan. 22, 2009) 4 pages.
BASF Corporation, Joncryl® 99, data sheet (Dec. 11, 2008) 2 pages.
BASF Corporation, Joncryl® DFC 3025, data sheet (Nov. 12, 2008) 2 pages.
BASF Corporation, Joncryl® DFC 3030, data sheet (Nov. 12, 2008) 2 pages.
BASF Corporation, Joncryl® DFC 3040, data sheet (Nov. 13, 2008) 2 pages.
BASF Corporation, Joncryl® DFC 3050, data sheet (Nov. 12, 2008) 2 pages.
BASF Corporation, Joncryl® ECO 2124, data sheet (Nov. 14, 2008) 2 pages.
BASF Corporation, Joncryl® FLX 5000, data sheet (Nov. 14, 2008) 3 pages.
BASF Corporation, Joncryl® HPD 196, data sheet (Mar. 12, 2009) 3 pages.
BASF Corporation, Joncryl® HPD 296, data sheet (Dec. 11, 2008) 3 pages.
BASF Corporation, Joncryl® HPD 671, data sheet (Dec. 11, 2008) 4 pages.
BASF Corporation, Joncryl® HPD 696, data sheet (Nov. 26, 2008) 3 pages.
BASF Corporation, Joncryl® HPD 71, data sheet (Dec. 11, 2008) 2 pages.
BASF Corporation, Joncryl® HPD 96, data sheet (Dec. 11, 2008) 2 pages.
BASF Corporation, Joncryl® HRC 1645, data sheet (Nov. 13, 2008) 2 pages.
BASF Corporation, Joncryl® HRC 1661, data sheet (Nov. 13, 2008) 2 pages.
BASF Corporation, Joncryl® HRC 1663, data sheet (Nov. 13, 2008) 2 pages.
BASF Corporation, Joncryl® LMV 7000 Series User's Guide (2009) 3 pages.
BASF SE, "Faster, stronger and more efficient! Joncryl® HPD 296—water-based resin technology for high performance pigment dispersions" brochure (2009) 8 pages.
BASF, "BASF Resins," http://www2.basfus/naftaresins/, Publication date unknown, last printed Mar. 10, 2009, 1 page.
Bristow, J.A., "Liquid absorption into paper during short time intervals," Svensk Papperstidning (1967) 70(19):623-629.
BYK-Chemie GmbH, Data Sheet W210 for DISPERBYK-190, DISPERBYK-191, DISPERBYK-192, DISPERBYK-194 (2008) 4 pages.
Cabot Corporation, "CAB-O-JET® 200" (Feb. 2009) 1 page.
Carbon Black Handbook, published by Carbon Black Society, issued by Tosho Shuppan Co. p. 440-441.
Cary Company, The, "Degussa Carbon Blacks," http://www.thecarycompany.com/products/Degussa-Blacks.html (Jun. 8, 2007) 3 pgs.
Casas-Ballester, R., Recharger Magazine (Jul. 1999).
Columbian Chemicals brochure, "Raven blacks: industrial applications require powerful solutions," Apr. 22, 2005, 5 pages.
Concise Encyclopedia of Polymers, Science & Engineering (1990) 160-171.
Cytec Surface Specialties, "Fiche de donnees de securite conforme a la Directive 2001/58/CE, Ebercryl 2003" (2005) 8 pages.
Degussa, "Purity of Pigment Black," Technical Information TI 1223 (Feb. 2001) 3 pages.
Degussa, What is Carbon Black? brochure, 9 pages.
Donnet, J.B. et al., "No. 294—Etude de Faction chimique des oxydants sur le noir de carbone" or "No. 294—Study of he chemical action of oxidants on carbon black," (1962) 1727-1735 (with English translation).
Donnet, J.B. et al., "Radical reactions and surface chemistry of carbon black No. 252," Bull. Soc. Chim. Fr. (1960) 1609-1618.
Donnet, J.B. et al., "Surface chemistry and priviledged sites of fine charges," Extract from the revue General du Caoutchouc (1959) 3-12 (28 pages).
Ehrburger, D.F. et al., "Use of N2, Ar and CO2 adsorption for the determination of microporosity and surface fractal dimension of carbon blacks and silicas," Pure & Appl. Chem. (1993) 65(10):2223-2230.
Fujiu, T. et al., "Oxidation of hydrazino-1,3,5-triazine," Nippon Kagaku Kaishi (1989) 1652-1654.
Galgoci, E.C. et al., "Innovative molecular defoamer technology," Air Products and Chemicals, Inc., Pub. No. 120-05-017-GLB (2004) 1-19.
Hanke, M.T. et al., "Studies on proteinogenous amines. XIV. A microchemical colorimetric method for estimating tyrosine, tyramine and other phenols," J. Biol. Chem. (1922) 50:235-270.
Harris, J.M., "Laboratory synthesis of polytheylene glycol derivatives," JMS—Rev. Macromol. Chem. Phys. (1985) C25(3):325-373.
Hirtt, P., "Carbon black oil absorption, ASTM D2414 and D3493 recent evolution and changes," India Rub Tech Expo 2004, Feb. 13-14, 2004, Mysore, Karnataka, India.
http:inoxairproducts.com/chemicals/surfynoladditives.html Surfynol & Dynol Additives (Aug. 14, 2009—originally accessed Sep. 10, 2007).
http://www.answers.com/topic/sulfonation-and-sulfation, "Sulfonation and sulfation" (2009) 1 page.
http:www.nissin-chem.co.jp/english/products/new.htrnl, "Surfynol/Olfine" (Aug. 14, 2009—originally accessed Sep. 10, 2007).
Huntsman Corporation, "JEFFSPERSE® X3102 Dispersant" Advanced Technical Bulletin (2008) 2 pages.
Huntsman Corporation, "SURFONAMINE® B-60 Amine" Technical Bulletin (2007) 2 pages.
Huntsman Corporation, "SURFONAMINE® L-100 Amine" Technical Bulletin (2007) 2 pages.
Huntsman Corporation, "SURFONAMINE® L-207 Amine" Technical Bulletin (2007, 2008) 2 pages.
Huntsman Corporation, "SURFONAMINE® L-300 Amine" Technical Bulletin (2007, 2008) 2 pages.

(56) References Cited

OTHER PUBLICATIONS

Huntsman Corporation, "The use of SURFONAMINE® amines in ink and pigment applications," Technical Bulletin (2006) 5 pages.
International Agency for Research on Cancer (IARC)—Summaries and Evaluations "Carbon Black" (1996) 65:149.
Johnson Polymer, Material Safety Data Sheet for Joncryl® HPD 296 (2005) 1-5.
Johnson Polymer, Material Safety Data Sheet for Joncryl® HPD 96 (2004) 1-5.
Johnson, J.E., "Surface modification of black pigments: a novel approach for advancing black pigment performance in imaging systems," Proceedings of IS&T Annual Conference XX, XX, No. 50th Conference (1997) 310-312.
Knapp, D.R., "Derivation of particular compound types," in Handbook of analytical derivatization reactions, 9th Edition, John Wiley & Sons (1979) p. 60.
Koessler, K.K. et al., "Studies on proteinogenous amines. II. A microchemical colorimetric method for estimating imidazole derivatives," J. Biol. Chem. (1919) 39:497-519.
Kunishima, M. et al., "Development of chlorotriazine polymer dehydrocondensing reagents (Poly-Trzs)," Tetrahedron (2007) 63:2604-2612.
Lahaye, J. et al., "Surface chemistry of carbon: an atomistic approach," Pure & Appl. Chem. (1989) 61(11):1853-1858.
Lessard, B. et al., "Styrene/acrylic acid random copolymers synthesized by nitroxide-mediated polymerization: effect of free nitroxide on kinetics and copolymer composition," Macromolecules (2008) 41(10):3446-3454.
Luthge, T. et al., "New methods of carbon black surface modification," IS&T's NIP 19:2003 International Conference on Digital Printing Technologies, p. 194-198.
MacKenzie, J.D. et al., "Physical properties of sol-gel coatings," J. Sol-Gel Science & Tech. (2000) 19:23-29.
Mellor, J.W., "Oxides and oxyacids of chlorine, etc.," from Modern Inorganic Chemistry, Longmans, Green and Co., New York (1925) p. 334-335.
National Industrial Chemicals Notification and Assessment Scheme (NICNAS), Full Public Report "Polymer in Joncryl® HPD 96 MEA," (2006) 1-7.
Nippon Shokubai, "Polyethyleneimine. EPOMIN" taken from http://www.shokubai.co.jp/eng/products/epomin.html (2006) 10 pages.
PMB, Ltd., "What is masterbatch?" http://www.pmb.co.uk/masterbatch.htm (2007) 2 pages.
Powell Fabrication & Manufacturing Inc., "General Information about sodium hypochlorite," http://www.powellfab.com/technical_information/preview/general_info_about_sodium_hypo.asp, First date available unknown, Jun. 10, 2009.
Sartomer Company, Inc., Product Bulletin: SMA® 1440 H Solution (2002) 1 page.
Sartomer Company, Inc., Product Bulletin: SMA® 17352 H Solution (2002) 1 page.
Sax, N.I., Dangerous Properties of Industrial Materials, Reinhold Publishing Corporation, New York (1957) 778 and 1122.
Sensient Imaging Technologies, Inc., Material Safety Data Sheet for Joncryl 678 SOL EXP. 8003-112-01 (2008) 1-4.
Subramanian, R.V., "Electrochemical polymemrization and deposition on carbon fibers," Pure & Appl. Chem. (1980) 52:1929-1937.
Suetsugu, A. et al., "Effects of amphiphilic amines on moisture characteristics of alluvial and volcanic soils," Soil. Sci. Soc. Am. J. (2001) 65:1129-1135.
Textile Printing, LCW Miles, 2nd Edition (1994) ch. 3.2, pp. 60-87.
Torres, L. et al., "Isolation and characterization of an Fe(III)-chelating compound produced by pseudomonas syringae," App. Environ. Microbiol. (1986) 52(1):157-160.
Tsubokawa, N. et al., "Grafting of polyesters onto carbon black. 2. Effect of temperature and solvent on the polymerization of beta-propiolactone initiated by COOK groups on the surface of carbon black," Polymer Bulletin (1982) 7:589-596.
Tsubokawa, N., "Carbon-black," Polymer Sci. Tech. (1991) 2(2):71-80.
Tsubokawa, N. et al., "Grafting onto carbon black having few functional group 1. Introduction of carboxyl group by use of radical initiator and its application for grating of polyesters," Nihon Gomu Kyoukaishi (1989) 62:668-673 (Abstract only).
Tsubokawa, N. et al., "Reactive carbon black having isocyanate or acyl azide group. Preparation and reaction with polymers having hydroxyl group," Polymer Bulletin (1985) 13:215-222.
Tsubokawa, N. et al., "Grafting of functional polymers onto reactive carbon black having chlorotriazinyl groups," Polymer Journal (1988) 20(9):721-728.
Tsubokawa, N. et al., "Grafting onto carbon black by the reaction of reactive carbon black having acyl chloride group with several polymers," Polymer Bulletin (1987) 17:87-93.
Tsubokawa, N. et al., "Grafting onto carbon black by the reaction of reactive carbon black having epoxide groups with several polymers," J. Poly. Sci. Part A: Poly Chem. (1980) 27:1701-1718.
Tsubokawa, N., "Functionalization of carbon black by surface grafting of polymers," Prog. Polym. Sci. (1992) 17:417-470.
Vancha, A.R. et al., "Use of polyethyleneimine polymer in cell culture as attachment factor and lipofection enhancer," BMC Biotechnology (2004) 4:23, 12 pages.
Voorhies, J.D. et al., "Coulometry with the carbon black electrode," Anal Chem. (1960) 32(13):1855-1857.
International Search Report and Written Opinion of Application No. PCT/US2007/083257 dated Apr. 14, 2008 (9 pages).
International Search Report and Written Opinion of Application No. PCT/US2007/083258 dated Apr. 14, 2008 (9 pages).
Partial International Search for Application No. PCT/US2008/074086 dated Apr. 6, 2009 (3 pages).
International Search Report and Written Opinion for Application No. PCT/US2008/074086 dated Aug. 18, 2009 (13 pages).
Invitation to Pay Additional Fees and Partial International Search for Application No. PCT/US2009/054700 dated Jul. 8, 2010 (5 pages).
International Search Report and Written Opinion for Application No. PCT/US2009/054700 dated Sep. 28, 2010 (20 pages).
United States Office Action for U.S. Appl. No. 11/933,116 dated Feb. 13, 2009 (8 pages).
United States Patent Office Action for U.S. Appl. No. 11/933,116 dated Jun. 18, 2010 (5 pages).
United States Office Action for U.S. Appl. No. 11/933,192 dated Apr. 2, 2009 (11 pages).
United States Patent Office Action for U.S. Appl. No. 11/933,192 dated Feb. 22, 2010 (13 pages).
United States Patent Office Action for U.S. Appl. No. 11/933,192 dated Sep. 15, 2010 (10 pages).
United States Patent Office Action for U.S. Appl. No. 12/197,087 dated Apr. 5, 2010 (6 pages).
Australian Office Patent Examination Report No. 1 for Application No. 2010234392 dated Dec. 16, 2013 (5 pages).
Japanese Patent Office Action for Application No. 2012-504842 dated Apr. 8, 2014 (7 pages, English translation included).
Office Action from the Chinese Patent Office for Application No. 201080025310.9 dated Aug. 5, 2013 (English Translation and Original, 7 pages).
European Examination Report for Application No. 10714738.1 dated Jan. 15, 2014 (6 pages).
Australian Patent Examination Report No. 2 for Application No. 2010234392 dated Mar. 23, 2015 (3 pages).
Japanese Patent Office Action for Application No. 2012-504842 dated Apr. 14, 2015 (4 pages, English translation included).
Chinese Patent Office Action for Application No. 201080025310.9 dated Mar. 25, 2015 (9 pages, English translation included).
European Patent Office Action for Application No. 10714738.1 dated Sep. 23, 2015 (5 pages).

* cited by examiner

SELF-DISPERSING PARTICLES AND METHODS FOR MAKING AND USING THE SAME

CROSS-REFERENCE TO RELATED APPLICATIONS

The present application claims priority to U.S. Provisional Patent Application No. 61/167,419 filed Apr. 7, 2009, the entire contents of which are herein incorporated by reference.

FIELD OF USE

The present invention relates to the surface modification of particles, and more particularly, dye particles (e.g., a solvent dye, a disperse dye, a water insoluble dye, a sparingly soluble dye, or a combination thereof), inorganic pigment particles, and additives (e.g., a sublimable UV absorber or a sublimable optical brightener) to form a self-dispersing particle. The invention further relates to end use applications for the self-dispersing particles including, but not limited to, coatings, metal coatings, paints, papers, adhesives, latexes, toners, textiles, fibers, plastics (flexible films and bulk materials), cosmetics, and inks. Specific examples of inks include, without limitation, printing ink for paper, textiles, polyesters, fibers, plastics (flexible films and bulk materials), metals, metal deco and plastics, UV curing, wood stains, writing instruments, felt pens, sublimation printing on man-made fibers, coated natural fibers, coated materials, plastics, coated hard substrates, and color filters. Other examples of end uses include, without limitation, printing ink for sublimation printing, transfer, direct and inkjet printing applications.

INTRODUCTION

Aqueous dispersions comprising dye particles, inorganic pigment particles, and additives may offer several advantages over water-soluble dyes when it comes to end applications including, but not limited to, inks, coatings, paints, papers, adhesives, latexes, toners, textiles, fibers, wood stains, color filters, cosmetics, and plastics. For example, they may exhibit at least one of greater optical density and edge acuity compared to water-soluble dyes. Additionally, dye particles and additives showing sublimation properties generally can only be printed as dispersions. Unfortunately, these particles can also have a propensity to settle during storage, thus initially limiting their use in demanding applications such as inkjet inks. Good stability of dye particle-based inks may be difficult to obtain.

Stabilization of the dye particles in suspension has been obtained using dispersant-stabilization (i.e., providing steric and/or electrostatic stabilization), and the result, although industrially applicable, only has a limited shelf life. The advent of media mills to grind particles to sub-micron level combined with dispersants for colloidal stability has propelled the use of dye dispersions in inkjet ink formulations. However, dispersants can increase the viscosity of dispersions such that it becomes difficult to jet inks containing the dispersions from small orifices in an inkjet print head. Moreover, dispersants can add significant cost to the preparation of the materials listed above and are therefore economically unfavorable as well. Dispersants are generally not covalently bonded to the surface of the dye and therefore, stabilization may be compromised.

Accordingly, a need remains for self-dispersed particles that can overcome at least some of the problems typically associated with current end applications comprising current dye particle systems (e.g., current water-soluble dye-based systems and current dye particle systems employing dispersants).

SUMMARY

In one aspect, a method is provided of modifying a particle. The method may comprise reacting a reactive compound having an X—[Y]$_n$ reactive group with a secondary compound N—S-ZM to form a substituted reactive intermediate [Y]$_a$—X—(N—S-ZM)$_b$, and reacting the particle with the substituted reactive intermediate [Y]$_a$—X—(N—S-ZM)$_b$ to attach the substituted reactive intermediate to the surface of the particle to form a surface modified particle. The particle may comprise at least one of a dye particle, an inorganic pigment particle, an additive, or a combination thereof. X may be a sulfonyl, phosphoryl, or 1,3,5-triazinyl group. Y may be a halogen leaving group. N may be a nucleophilic group. S may be an organic group. ZM may be an ionizable end group, and n is an integer between 1 and 3, b is an integer between 1 and 3, and a=n–b, wherein n is equal to or greater than b, and wherein if b is 2 or 3, each N—S-ZM can be the same or different.

In another aspect, another method of modifying a particle is provided. The method may comprise attaching a reactive compound group to a surface of the particle. The particle may comprises at least one of a dye particle, an inorganic pigment particle, an additive, or a combination thereof. Subsequently, the reactive group may be displaced with an organic substrate having an ionizable end group. The particle may be selected from the group consisting of Disperse Blue 14, Disperse Blue 19, Disperse Blue 72, Disperse Blue 334, Disperse Blue 359, Disperse Blue 360, Disperse Orange 25, Disperse Yellow 54, Disperse Yellow 64, Disperse Red 55, Disperse Red 60, Macrolex Red H, Disperse Brown 27, Solvent Blue 67, Solvent Blue 70, Solvent Red 49, Solvent Red 146, Solvent Red 160, Solvent Yellow 162, Solvent Violet 10, Solvent Black 29, Acid Yellow 204, Acid Yellow 151, Acid Orange 60, Acid Red 182, Acid Red 357, Acid Red 359, Acid Blue 193, Acid Brown 355, Acid Violet 90, Acid Black 172, Acid Black 194, Acid Black 52, Acid Black 60, titanium (IV) oxide, iron (III) oxide, and zinc oxide.

In a further aspect, an additional method of modifying a particle is provided. The method may comprise attaching a reactive group X—Y to a surface of the particle. The particle may comprise at least one of a dye particle, an inorganic pigment particle, an additive, or a combination thereof. Subsequently, the method comprises displacing Y with an organic substrate N—S-ZM to form a surface-modified particle having attached X—N—S-ZM; wherein X is a sulfonyl, phosphoryl, or 1,3,5-triazinyl group; Y is fluorine, chlorine, bromine, or iodine; N is an amine, an imine, a pyridine, or a thiol group; S is substituted or unsubstituted alkyls, aryls, or polymer chains having a molecular weight range from about 300 to about 8000; Z is a carboxyl, sulfonyl, phenolic, phosphoryl, ammonium, trimethylammonium, or tributylammonium group; and M is a halide, a negatively charged ion, a proton in salt form, or a cation in salt form.

In yet a further aspect, provided is a surface modified that may comprise a dye particle, an inorganic pigment particle, an additive, or a combination thereof having about 0.1 to about 0.8 mMoles of active hydrogen per gram of particle.

In another aspect, provided is a surface modified particle that may comprise a particle comprising at least one of a dye particle, an inorganic pigment particle, an additive, or a combination thereof and a total amount of alkali metal equivalent to about 0.1 to about 0.8 mMoles of active hydrogen per gram of particle.

In an additional aspect, provided is a modified particle that may comprise at least one of a dye particle, an inorganic pigment particle, an additive, or combination thereof; and a group comprising (N—S-ZM) attached thereto, wherein N is a nucleophilic group; S is an organic group; and ZM is an ionizable end group.

DETAILED DESCRIPTION

Figure 1:
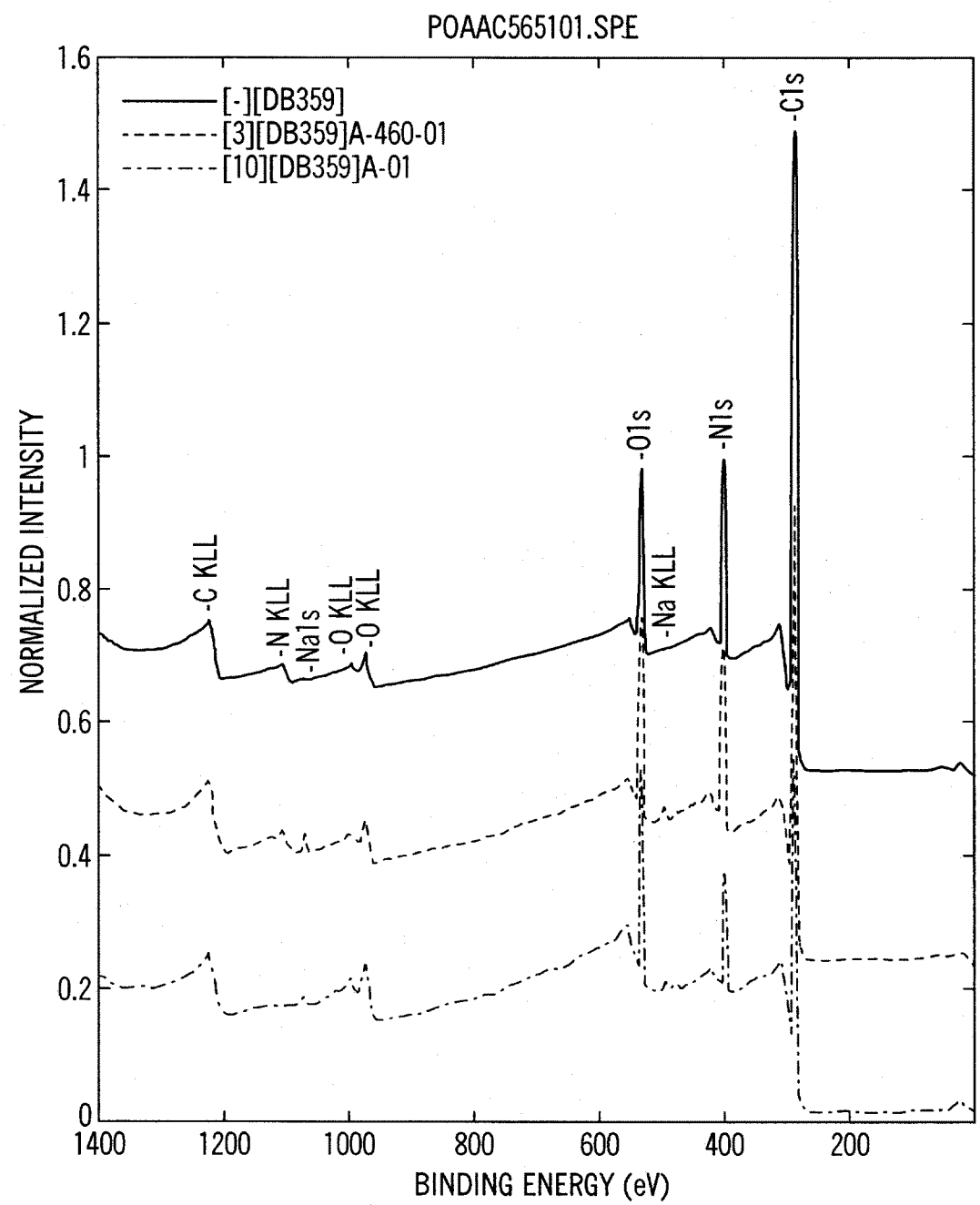
FIG. 1 shows low resolution X-Ray Photoelectron Spectroscopy (XPS) spectra of Disperse Blue 359 and modified Disperse Blue 359 samples from Examples 3 and 10.
Figure 2:
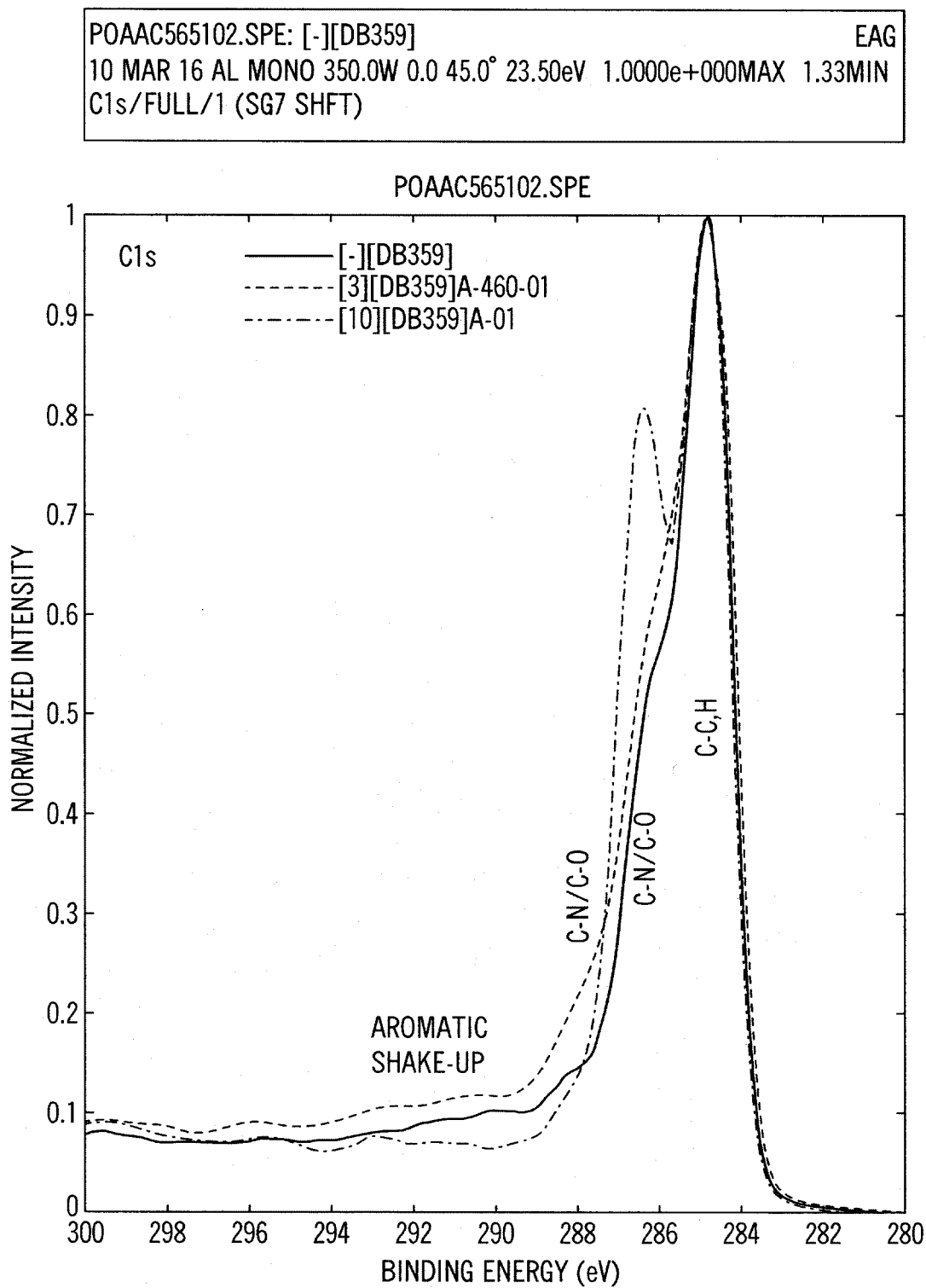
FIG. 2 shows high energy resolution C1s spectra of Disperse Blue 359 and modified Disperse Blue 359 samples from Examples 3 and 10.
Figure 3:
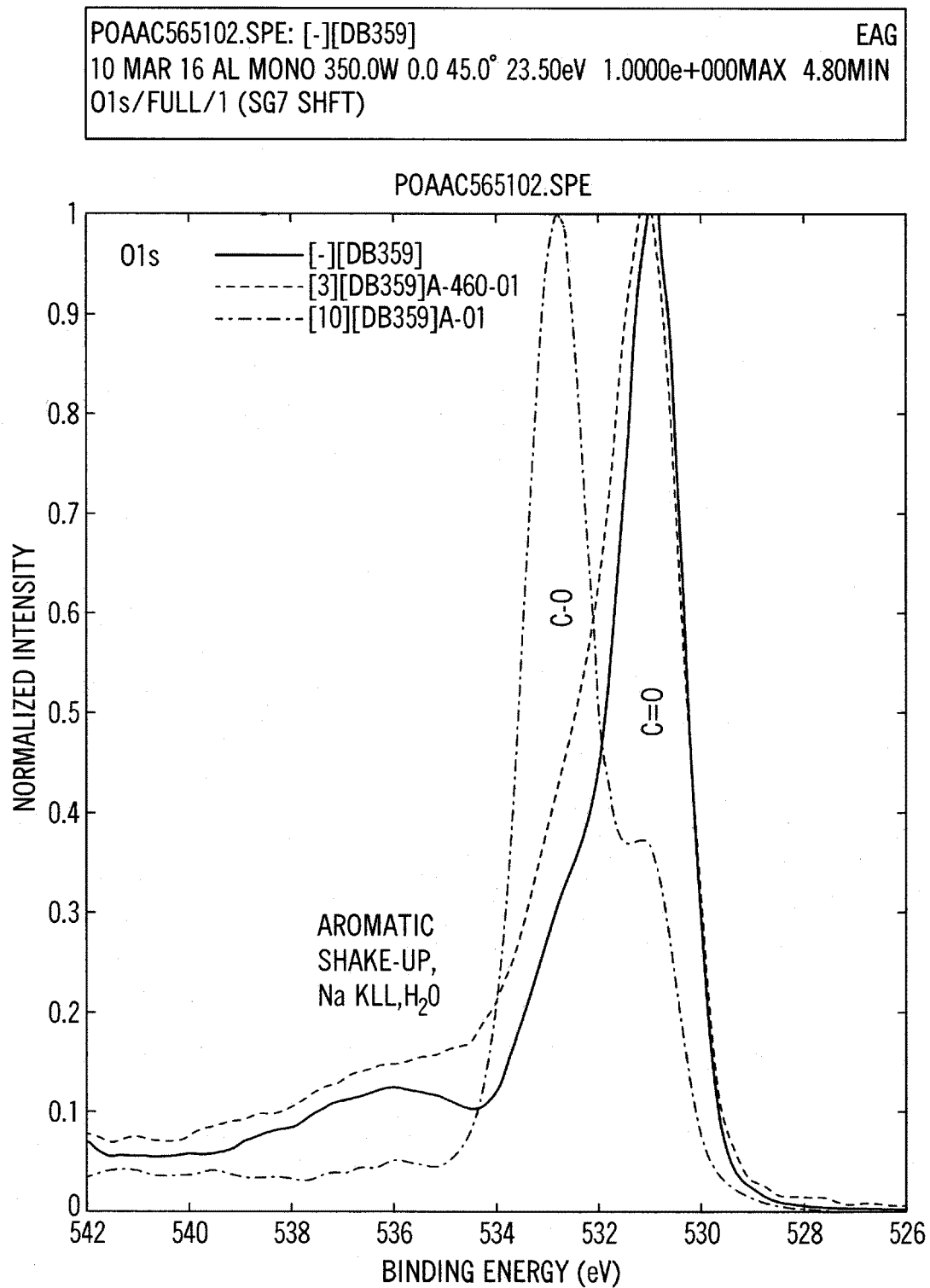
FIG. 3 shows high energy resolution O1s spectra of Disperse Blue 359 and modified Disperse Blue 359 samples from Examples 3 and 10.

Before any embodiments of the invention are explained in detail, it is to be understood that the invention is not limited in its application to the details of construction and the arrangement of components set forth in the following description. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

In one aspect, the invention may provide a method of modifying a particle that may include reacting cyanuric chloride with about three equivalents of a secondary compound or a mixture of secondary compounds to displace all reactive chlorines to form a substituted triazine. The substituted triazine may be reacted with a surface of a particle to form a self-dispersing particle.

In another aspect, the invention may provide a method of modifying a particle that may include reacting a reactive compound having an X—[Y]$_n$ reactive group with a secondary compound N—S-ZM to form a substituted reactive intermediate [Y]$_a$—X—(N—S-ZM)$_b$. The method may also include reacting a particle with the substituted reactive intermediate [Y]$_a$—X—(N—S-ZM)$_b$ to attach the substituted reactive intermediate to the surface of the particle to form a self-dispersing particle. X represents a 1,3,5-triazinyl group. Y may be a leaving group such as a halogen, N may be a nucleophilic group, S may be an organic group, and ZM may be an ionizable end group. Also, n may be an integer between 1 and 3, b may be an integer between 1 and 3, and a=n−b. When n is equal to or greater than b, and if b is 2 or 3, each N—S-ZM can be the same or different.

In a further aspect, the invention may provide a method of modifying a particle that may include attaching a reactive group X—Y to a surface of a particle. Subsequently Y may be displaced with an organic substrate N—S-ZM to form a self-dispersing particle having attached X—S-ZM. X represents a 1,3,5-triazinyl group. Y may be a leaving group such as fluorine, chlorine, bromine, or iodine. N may be an amine, an imine, a pyridine, or a thiol group. S may be substituted or unsubstituted alkyls, aryls, or polymer chains having a molecular weight range from about 300 to about 8000. Z may be a carboxyl, sulfonyl, phenolic, phosphoryl, ammonium, trimethylammonium, or tributylammonium group. M may be a halide, a negatively charged ion, a proton in salt form, or a cation in salt form.

In another aspect, the invention may provide a method of modifying a particle that may include milling and dispersing a particle with a grinding aid to form a particle dispersion. The method may also include reacting a reactive compound having an X—$[Y]_n$ reactive group with a secondary compound N—S-ZM to form a substituted reactive intermediate $[Y]_a$—X—$(N—S-ZM)_b$. The method may also include reacting a dispersion with the substituted reactive intermediate $[Y]_a$—X—$(N—S-ZM)_b$ to attach the substituted reactive intermediate to the surface of the particle to form a self-dispersing particle. The method may also include purifying the self-dispersing particle to remove impurities, including the grinding aid. X represents a 1,3,5-triazinyl group. Y may be a leaving group such as a halogen, N may be a nucleophilic group, S may be an organic group, and ZM may be an ionizable end group. Also, n may be an integer between 1 and 3, b may be an integer between 1 and 3, and a=n−b. When n is equal to or greater than b, and if b is 2 or 3, each N—S-ZM can be the same or different.

In a further aspect, the invention may provide a method of modifying a particle that may include reacting cyanuric chloride with about three equivalents of a secondary compound or a mixture of secondary compounds to displace all reactive chlorines to form a substituted triazine. The substituted triazine may be reacted with a particle dispersion (D)(R) that may include particle (D), a dispersant or polymer (R), and water to form a self-dispersing particle. The method may also include adding additional polymer to a particle dispersion. The additional polymer may be the same or different than (R). The self-dispersing particle may have attached at least one of the substituted triazine(s), (R), and additional polymer. The particle dispersion (D)(R) may optionally be formed by milling and dispersing a particle. The method may also include purifying the self-dispersing particle to remove impurities, including the unattached dispersant and/or polymer. Each secondary compound can be the same or different. The group R may be an oligomer, polymer, polymeric resin, dispersant or binder already present in a raw particle dispersion; an oligomer, polymer, polymeric resin, dispersant or binder added to a raw particle; additional oligomer, polymer, polymeric resin, dispersant or binder added to a raw particle dispersion; or combinations thereof.

In one embodiment, the invention provides a method of modifying a particle. The method may include attaching an organic group with charged end groups (negative or positive) through the intermediacy of a reactive molecule to produce a surface stabilized modified particle. Without being limited by theory, it is believed that the stabilization is achieved by repulsion forces which are generated by an even distribution of similarly charged groups, which are covalently attached on sub micron sized particles.

In yet another embodiment, the invention provides a dispersion that includes a self-dispersing particle that has been formed by a reaction of a particle with a reactive intermediate that has been attached to suitable organic molecules as described above. The selection of reactive intermediates that are stable in an aqueous environment is another aspect of the present invention.

In another embodiment, the invention provides a method of modifying a particle that may include attaching a reactive group to a surface of a particle and subsequently displacing the reactive group with an organic substrate having an ionizable end group.

In a further embodiment, the invention provides a dispersion that includes a self-dispersing particle comprising about 0.1 to about 10 mMoles of sulfur and about 0.1 to about 10 mMoles of active hydrogen per gram of particle, and water In another aspect, the invention provides an oligomer, polymer, polymeric resin, dispersant or binder attachment to a particle or self-dispersing particle, which enhances at least one durability property such as crock fastness (water fastness), and rub resistance, as well as color depth. These properties are relevant to certain of the applications discussed herein, such as digital printing. Fast print speeds and small jet volumes (2-5 pico liters) also dictate low viscosity ink formulations particularly for thermal ink jetting. Attaching the oligomer, polymer, polymeric resin, dispersant or binder reduces the quantity requirement. Additionally, the polymer stays with the particle, and therefore, affords low viscosity formulations with comparable results.

Method for Making Self-Dispersing Particles

One aspect of the present invention relates to a method for making stable, self-dispersing particles.

As used herein, the term "particle" refers to a water-insoluble component. The particle may comprise at least one of a dye particle, an inorganic pigment particle, an additive, or a combination thereof.

As used herein, the term "dye particle" is meant to comprise at least one of a solvent dye, a disperse dye, a water insoluble dye, a sparingly soluble dye, or a combination thereof. Dye particles may be used to impart color to a substrate. Examples of substrates may include, but are not limited to, plain or coated paper, film and other receiving media like textiles (e.g., woven, non woven, knitwear, etc.). Dye particles may be in the form of fine dispersions.

As used herein, the term "inorganic pigment particle" is meant to comprise an inorganic colorant used to impart color to a substrate such as plain or coated paper, film and other types of receiving media. The inorganic pigment particle may also impart color to cosmetic formulations. Inorganic pigment particles may be white, black as well as other colors.

As used herein, the term "additive" is meant to comprise a non-dye molecule or particle or a non-pigment molecule or particle that can improve or provide certain properties in an end product. Examples of additives include, but are not limited to, non-dye molecules such as sublimable UV absorbers or sublimable optical brighteners. Additives may be colorless.

As used herein, the term "self-dispersing" particle means a particle having stabilizing groups covalently attached to its surface such that the particle forms a stable aqueous dispersion in the absence of any additional dispersing agents.

As used herein, the term "stable" means that on aging the dispersion will undergo minimal changes as demonstrated by less than 10% change in measured critical properties (such as at least one of mean particle size, viscosity, surface tension and pH) when stored at ambient temperature over a period of at least about three months to six months to two years. Accelerated test methods include a heat stability test at about 60° C. for at least about one week or a heat stability test at about 60° C. for at least about four weeks. The self-dispersing particles show an unchanged color yield upon sublimation on a man-made fiber (example: polyester).

In some embodiments, "attached," "attaching," or "attachment" may be direct or indirect.

In a first embodiment, the method for making a self-dispersing particle generally comprises (1) reacting a particle (D) with a reactive compound having an X—Y reactive group and a halogen-containing reagent to attach the reactive group X—Y to the surface of the particle (D), and thereby form a particle reactive intermediate (D)X—Y; and (2) reacting the particle reactive intermediate (D)X—Y with a secondary compound N—S-ZM to form a self-dispersed particle (D)-X—S-ZM ("the substitution step"). One example of this embodiment may include, without limitation, a method of modifying a particle that may comprise attaching a reactive group X—Y to a surface of a particle; and subsequently displacing Y with an organic substrate N—S-ZM to form a self-dispersing particle having attached X—S-ZM.

In a second embodiment, the method for making the self-dispersing particle (D)-X—S-ZM may comprise (1) reacting a reactive compound having an X—Y reactive group with a secondary compound N—S-ZM to form a substituted reactive intermediate X—S-ZM ("the substitution step"); and (2) reacting a particle (D) with the substituted reactive intermediate X—S-ZM to attach the substituted reactive intermediate X—S-ZM to the surface of the particle using a secondary displacement reaction to form a self-dispersing particle (D)-X—S-ZM. One example of this embodiment may include, without limitation, a method of modifying a particle that may comprise reacting a reactive compound having an X—$[Y]_n$ reactive group with a secondary compound N—S-ZM to form a substituted reactive intermediate $[Y]_a$—X—$(S\text{-}ZM)_b$; and reacting a particle with the substituted reactive intermediate $[Y]_a$—X—$(S\text{-}ZM)_b$ to attach the substituted reactive intermediate to the surface of the particle to form a self-dispersing particle; wherein n is an integer between 1 and 3; b is an integer between 1 and 3; and a=n−b; wherein n is equal to or greater than b, and wherein if b is 2 or 3, each N—S-ZM may be the same or different. In one embodiment, if b is 2 or 3, each N—S-ZM may be different.

In a third embodiment, the method for making the self-dispersing particle (D)-X—S-ZM may comprise (1) reacting a reactive compound having an X—Y reactive group with a secondary compound N—S-ZM to form a first substituted reactive intermediate X—S-ZM ("the substitution step"); (2) reacting a reactive compound having an X—Y reactive group with a different secondary compound N2-S2-Z2M2 from step (1) to form a second substituted reactive intermediate X—S2-Z2M2 ("the substitution step"); (3) reacting a particle (D) with the substituted reactive intermediates X—S-ZM and X—S2-Z2M2 to attach the substituted reactive intermediates to form a self-dispersed particle Z2M2-S2-X-(D)-X—S-ZM. Optionally S-ZM and S2-Z2M2 could be the same and all reactive groups will be substituted. The final attachment to the particle surface could be one of radical assisted disproportionation reaction.

In a fourth embodiment, the method for making the self-dispersing particle (D)-X—S-ZM may comprise (1) using a grinding aid and milling and dispersing a particle to form an aqueous particle dispersion; (2) reacting a reactive compound having an X—Y reactive group with a secondary compound N—S-ZM to form a first substituted reactive intermediate X—S-ZM ("the substitution step"); (3) reacting a reactive compound having an X—Y reactive group with a different secondary compound N2-S2-Z2M2 from step (2) to form a second substituted reactive intermediate X—S2-Z2M2 ("the substitution step"); (4) reacting a particle (D) pre-milled with a grinding aid with the substituted reactive intermediates X—S-ZM and X—S2-Z2M2 to attach the substituted reactive intermediates X—S-ZM and X—S2-Z2M2 to the surface of the particle using a radical initiated reaction to form a self-dispersing particle Z2M2-S2-X-(D)(R)—X—S-ZM; and (5) purifying the self-dispersed particle to remove impurities, including the grind aid. Optionally S-ZM and S2-Z2M2 could be the same.

In a fifth embodiment, the method for making a self-dispersing particle (D)(R)—X—S-ZM may comprise (1) optionally milling and dispersing a particle to form an aqueous particle dispersion (D)(R), the aqueous particle dispersion (D)(R) comprising particle (D), a dispersant or polymer (R) and water; (2) reacting cyanuric chloride with about three equivalents of a secondary compound SZM or a mixture of secondary compounds (SZM, $S_2Z_2M_2$ and $S_3Z_3M_3$) to displace all reactive chlorines to form a substituted triazine; (3) reacting the substituted triazine with the aqueous particle dispersion (D)(R) to form a self-dispersed particle (D)(R)—X—S-ZM, —X—$S_2$-$Z_2M_2$, —X—$S_3$-$Z_3M_3$, wherein one or more of X—S-ZM, —X—$S_2$-$Z_2M_2$, —X—$S_3$-$Z_3M_3$ is attached to (D)(R); and 4) purifying the self-dispersed particle to remove impurities, including the unattached dispersant. Optionally S-ZM, —$S_2$-$Z_2M_2$, $S_3$-$Z_3M_3$ could be the same or different. In this embodiment, X may be a triazine group.

In a sixth embodiment, a particle dispersion stabilized with polymer additives may be used for making the self-dispersing particle (D)(R)—X—S-ZM instead of the solid particle.

During the substitution step, at least one leaving group Y of the X—Y reactive group is substituted with the secondary compound N—S-ZM. In one example, without limitation, during the substitution step, at least one chlorine of the cyanuric chloride is substituted with the secondary compound N—S-ZM. N is a nucleophilic group including, without limitation, an amine, an imine, pyridine, or thiol. S may include, without limitation, organic groups such as, substituted or unsubstituted, alkyls, aryls and polymer chains having from about 1 to greater than 100 carbons or having a molecular weight range from about 300 to about 8000, and in the case of stabilization by negative charge, ZM is an acidic tail group, wherein Z may be, without limitation, carboxyl, sulfonyl, phenolic, and phosphoryl and M may be either a proton or a cation if it is present as a salt form.

The substitution reaction may impart charge and bulk to the surface of the particle. The substitution step may take place in an aqueous media. The choice of functional groups at the acidic tail is dictated by the final application while the functional groups at the basic head must have sufficient nucleophilicity to displace the leaving group Y. In one example, without limitation, the functional groups at the basic head must have sufficient nucleophilicity to displace the chlorine in cyanuric chloride. The secondary compound may comprise polymers, amines, amino acids, alcohols, thiols, and combinations thereof. Examples of secondary compounds (N—S-ZM and N2-S2-Z2M2, $N_3$—$S_3$-$Z_3M_3$) include, without limitation, amino benzoic acids, amino benzene sulfonic acids, amino phenols, amino sulfonic acids, polyethoxylated amino acids, sodium sulfanilate, sulfanilic acid, sodium p-aminobenzoate, p-aminophenol, ethyl 4-aminobenzoate, taurine, oleic acid (amino), sodium aminooleate, tetramethylammonium 4-aminobenzoate, and sodium 4-aminophenolate. Additional secondary compounds include organic polymeric substrates. Examples of organic polymeric substrates may include, without limitation, SMA (polystyrene-co-maleicanhydride resins), poly(styrene-co-maleic anhydride) cumene terminated resins, PEI, PEHA, SA (styrene-acrylic), pentaethylenehexamine, linear alkyl and branched ethoxy and propoxy chain polymers with a known molecular weight range of 300-3000 MW, available from Huntsman Chemicals under the trade name "Surfonamines," linear polyethoxy polymeric amines, linear propoxy polymeric amines, styrene acrylic copolymers available from BASF under the trade name "Joncryls," and polyethyleneimines sold under the trade name "Epomines."

In the case of stabilization by positive charge, ZM may be a positively charged quaternary ammonium type tail group, wherein Z may be, without limitation, ammonium, trimethylammonium, and tributylammonium, and M may be a halide or any negatively charged ion. Examples of secondary compounds N—S-ZM, N2-S2-Z2M2, and N3-S3-Z3M3 include, without limitation, simple diamino aromatics or cationic polymers consisting of polyethyleneimines, polyguanidines, quaternary ammonium compounds etc.

The final self-dispersing particle may be represented by the formula (D)-X—S-ZM for the first and second embodiments. In some instances, there may be multiple —S-ZMs attached to the particle that comprise different secondary compounds. For the third embodiment, the final self-dispersing particle may be represented by the formula Z2M2-S2-X-(D)-X—S-ZM. For the fourth embodiment, the final self-dispersing particle may be represented by the formula Z2M2-S2-X-(D)(R)—X—S-ZM. For the fifth embodiment, the final self-dispersing particle may be represented by the formula (D)(R)—X—S-ZM, —X—$S_2$-$Z_2$$M_2$, —X—$S_3$-$Z_3$$M_3$, wherein one or more of X—S-ZM, —X—$S_2$-$Z_2$$M_2$, —X—$S_3$-$Z_3$$M_3$ is attached to (D)(R). For the sixth embodiment, the final self-dispersing particle may be represented by the formula (D)(R)—X—S-ZM. And finally, the use of "2" or "3" to modify N, Z, M and S is meant to denote that N, Z, M and S and MN2, Z2, M2 and S2 and N3, Z3, M3 and S3 may be the same or different from each other. N2, Z2, M2 and S2 and N3, Z3, M3, and S3 may be selected from the same options set forth above with respect to N, Z, M and S.

R may be an oligomer, a polymer, a polymeric resin, a dispersant or binder. In one embodiment, a dispersant may be a polymer with functional groups that may be activated to form a radical and attach to the surface of the particles. R may be an oligomer, a polymer, polymeric resin, dispersant or binder already present in a raw particle dispersion; an oligomer, a polymer, polymeric resin, dispersant or binder added to a raw particle; additional polymer, polymeric resin, dispersant or binder added to a raw particle dispersion; or combinations thereof. Specific examples of polymers include, but are not limited to SMA (polystyrene-co-maleicanhydride resins), poly(styrene-co-maleic anhydride) cumene terminated resins, PEI, PEHA, SA (styrene-acrylic), pentaethylenehexamine, linear alkyl and branched ethoxy and propoxy chain polymers with a known molecular weight range of 300-3000 MW, available from Huntsman Chemicals under the trade name "Surfonamines," linear polyethoxy polymeric amines, linear propoxy polymeric amines, styrene acrylic copolymers available from BASF under the trade name "Joncryls," polyethyleneimines sold under the trade name "Epomines," and PU resins such as these made by Alberdingk, Bayer (Impranil), Huntsman Specialty (Dicrylan)." Specific examples of oligomers include urethane-acrylates, polyester-acrylates, and PEG-acrylates (from Cytec, Sartomer, Rahn).

To help illustrate the invention, a specific example of the second embodiment is provided below, wherein D represents a particle.

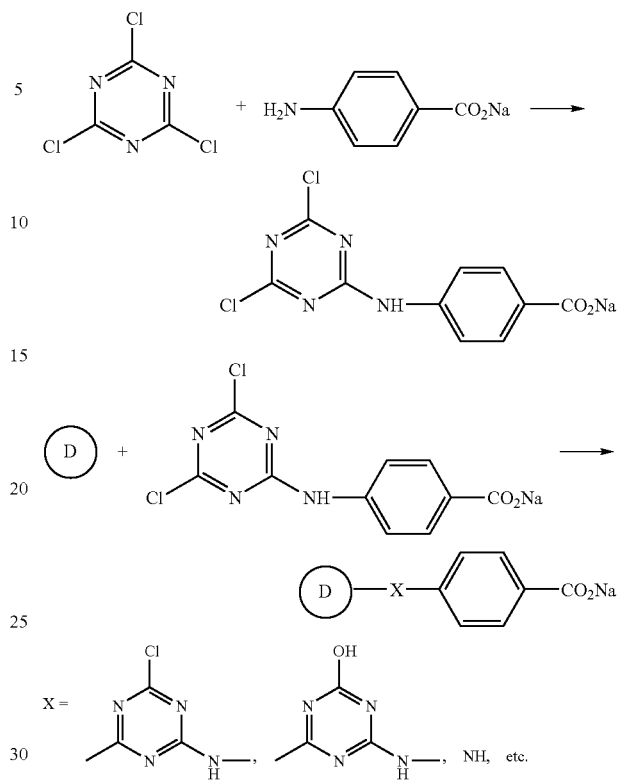

To help illustrate the invention, a specific example of the third embodiment is provided below, wherein D represents a particle.

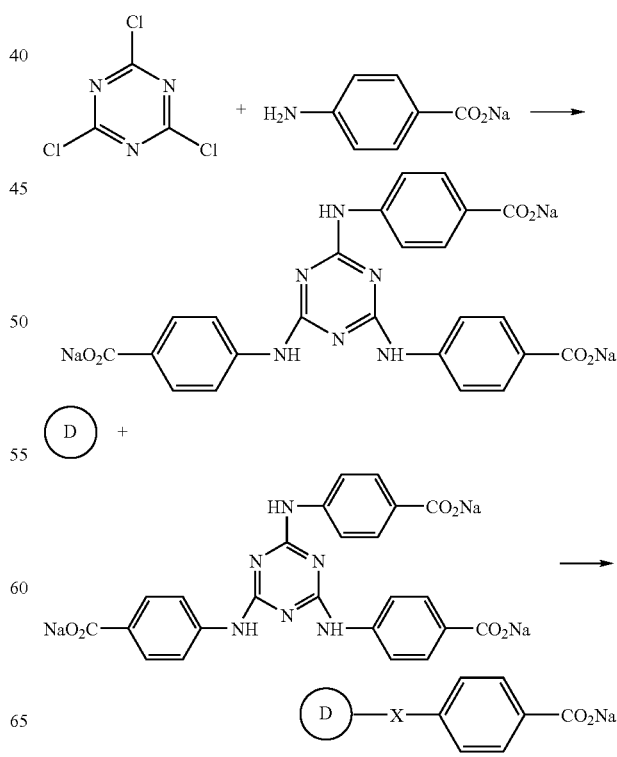

-continued

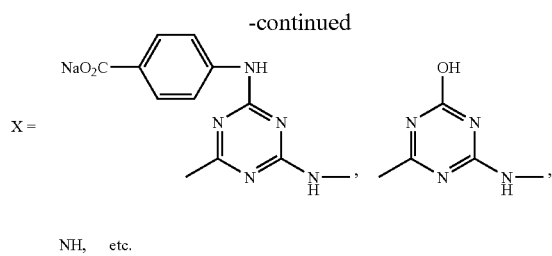

NH, etc.

To help illustrate the invention, a specific example of the fifth embodiment is provided below, wherein D represents a particle and R represents a polymer, polymeric resin or dispersant.

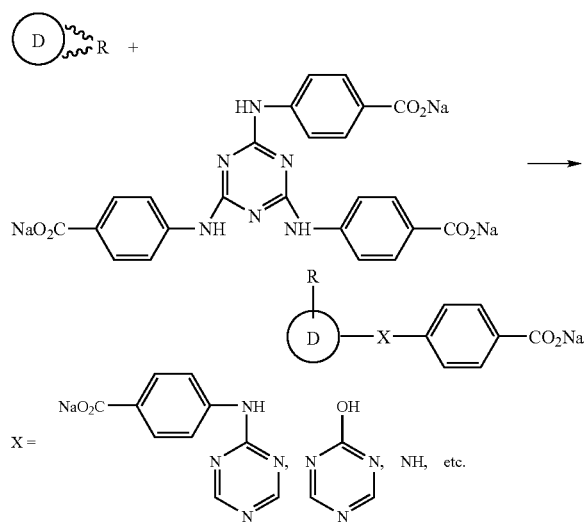

R = Polymeric Resin

More generally speaking, self-dispersing particles may be formed by milling raw particles or a wet press cake to a fine grind (typically less than about 200 nm) and subsequently attaching small organic molecules as stabilizing groups. Surface modification chemistries, including those described herein, may also be used on raw particle dispersions that comprise raw particle, a dispersant, and water. A raw particle may be dispersed as known in the art using one or several dispersant(s) and additives to form a raw particle dispersion. The raw particle dispersion, rather than the raw particle (e.g., in powder form), may be used in the surface modification techniques described herein, as well as other surface modification techniques that are well known in the art. In addition, raw particle dispersions and raw particle may be used together in the surface modification techniques described herein. Any combination of raw particles, raw particle dispersions, self-dispersing particles, and self-dispersing particles from raw particle dispersions, may be used in the surface modification techniques described herein.

In using any of the previous surface modification chemistries to modify a raw particle dispersion, the dispersant in the raw particle dispersion, as well as the compounds described above, may attach to the surface of the raw particle during the surface modification. In this way, dispersants capable of forming radicals and substituted reactive intermediates (for example, X—S-ZM) may be attached to the surface of the particle simultaneously. This may form a stable particle dispersion. Any remaining dispersant that does not attach to the surface of the particle during the surface modification process, i.e., any dispersant that is only adsorbed by the particle, and not attached, may be removed through a purification process.

In one embodiment, the commercial particle dispersion may be modified without any milling required. If smaller particles are desired, then the dispersion may be milled prior to or at any point during the attachment process. For example, a Buhler micro media mill may be used. In a further embodiment, the dispersant may be added to a raw particle and the particle and dispersant may then be milled prior to or at any point during the attachment process. In yet a further embodiment, the dispersant may be added to a raw particle and the particle and dispersant may then be milled, or a raw particle dispersion may be milled, and before or at any point during milling, additional polymer or substituted reactive intermediate may be added. A grind aid may also be milled with the raw particle and dispersant. The amount of dispersant added may be controlled to affect the final amount of dispersant attached to the surface of the particle. Milling performed prior to chemical treatment may allow the use of common mill chambers and parts while preventing re-agglomeration during the attachment process.

The particle modified by using this process may have a lower viscosity and higher surface tension than conventionally dispersed particles.

In some, but not all embodiments, the methods, modified particles, or dispersions comprising the modified particles may exclude elemental and alloyed metals, polymers (e.g., polyurethanes), clays, sol gels, plastic beads, or latex paints.

The embodiments of the invention are discussed in more detail below. Generally, the methods for making the self-dispersing particle begins with selecting a source of particle.

Particles

Dye particles that may be surface modified according to the present invention include all dyestuffs that are considered disperse and solvent dyes according to the Color Index. Dye particles that may be surface modified according to the present invention may include, but are not limited to, Disperse Blue 14, Disperse Blue 19, Disperse Blue 72, Disperse Blue 334, Disperse Blue 359, Disperse Blue 360, Disperse Orange 25, Disperse Yellow 54, Disperse Yellow 64, Disperse Red 55, Disperse Red 60, Macrolex Red H, Disperse Brown 27, Solvent Blue 67, Solvent Blue 70, Solvent Red 49, Solvent Red 146, Solvent Red 160, Solvent Yellow 162, Solvent Violet 10, Solvent Black 29, Acid Yellow 204, Acid Yellow 151, Acid Orange 60, Acid Red 182, Acid Red 357, Acid Red 359, Acid Blue 193, Acid Brown 355, Acid Violet 90, Acid Black 172, Acid Black 194, Acid Black 52, and Acid Black 60. Other suitable materials are available under the trade names Macrolex (available from Lanxess) and Elbasol.

Examples of commercial aqueous dye particle dispersions (D)(R) that may be used in the present invention, include, but are not limited to, Bafixan (BASF), Foron (Clariant), Transcorona (Huber), and Papicel (Eastwell). Examples of dye particle dispersions available from Sensient Imaging Technologies—Specialty Inks and Colors (Switzerland) include, but are not limited to, the Teraprint, Subli, and Elvajet products.

The quality of dye particles utilized may have an impact on the critical properties of the dispersion such as mean particle size, opacity, color shade, stability, etc. However, in one embodiment of the present invention, it is possible to use lower quality dye particles in the surface modification techniques of the present invention and produce a finished product that is of good quality. In the process of purifying the self-dispersing dye particles of the present invention, impurities from the raw dye particles or raw dye particle dispersions may be removed.

Dye powders and dyes in wet press cakes are available in a variety of particle sizes. Generally, smaller particle sizes are associated with larger surface areas, and larger surface areas can accommodate a higher concentration of hydrophilic surface groups, which ultimately enhance the dispersing ability of the dyes in aqueous-based media. Therefore, particle size can influence the dispersing ability of a self-dispersing dye particle. For example, the average primary particle size of a typical disperse dye in dry powder is between about 0.1 and 100 microns, particularly about 1 and 20 microns. Dye particles with large dimensions may be comminuted to a desired size either before or during surface modification using any number of techniques known to those skilled in the art. Such techniques may include, but are not limited to, a ball mill, an attritor, a flow jet mixer, an impeller mill, a colloidal mill and a sand mill (e.g., one commercially sold under the trade name 'Super Mill', 'Agitator Mill', 'Dyno-mill' or 'Beads Mill'). Mill media may include, but are not limited to, glass beads, zirconia beads and stainless steel beads. Mill media may comprise particles ranging in size from about 0.01 mm to about 5 mm, particularly from about 0.1 mm to about 3 mm.

Inorganic pigment particles that may be surface modified according to the present invention may include, but are not limited to, metal oxides, metal borates, metal sulfates, metal sulfides, metal chromates, metal carbonates, metal selenides, and combinations thereof. In some embodiments, suitable inorganic pigments can include, for example, titanium (IV) oxide, iron (III) oxide, zinc oxide, or combinations thereof.

Other inorganic pigments that may be surface modified according to the present invention may include, without limitation, pigments that have been FDA approved. These may be suitable for cosmetic applications. Acceptable inorganic pigments that may be used incosmetics may be found in 21 C.F.R. §§70-82, which are hereby incorporated by reference.

Particles are available in a variety of particle sizes. Generally, smaller particle sizes are associated with larger surface areas, and larger surface areas can accommodate a higher concentration of hydrophilic surface groups, which ultimately enhance the dispersibility of the pigment in aqueous-based media. Therefore, particle size can influence the dispersibility of a surface-modified particle. For example, the average primary particle size of particles in the present invention may be less than about 50 nm, particularly less than about 30 nm, particularly less than about 20 nm, and more particularly less than about 10 nm. Aggregates of particles may be less than about 200 nm, particularly less than about 150 nm, and more particularly less than about 100 nm. The surface area of particles may be greater than about 100 m2/g, particularly greater than about 150 m2/g, and more particularly greater than about 200 m2/g. Particles with larger dimensions may be comminuted to a desired size either before or during surface modification using any number of techniques known to those skilled in the art. Such techniques may include, but are not limited to, a ball mill, an attritor, a flow jet mixer, an impeller mill, a colloidal mill and a sand mill (e.g., one commercially sold under the trade name 'Super Mill', 'Agitator Mill', 'Dyno-mill' or 'Beads Mill'). Mill media may include, but are not limited to, glass beads, zirconia beads, plastic beads and stainless steel beads. Mill media may comprise particles ranging in size from about 0.01 mm to about 5 mm, suitably from about 0.1 mm to about 3 mm. If the pigment is easily crumbled, a rotary homogenizer or an ultrasonic homogenizer may be used to reduce particle size.

In some instances, prior to the creation of the self-dispersing particles, the particle may be wetted and milled to nano-sized particles and dispersed using a grind-aid and/or a polymeric resin. The particle may be in powder or wet cake form prior to milling with the aid of a grind aid. The milling may take place prior to, at any point during, or after the reaction with the substituted reactive intermediate or additional polymer. After the attachment reaction is complete, unattached grind-aid/resin may be removed using purification methods that are known to those skilled in the art, forming a dispersion containing primarily the modified pigment with attached substrates and water. Examples of grind aids include, but are not limited to Triton X-100 (available from Ashland Inc., Dublin, Ohio), Igepal CA-630 (available from Rhodia, Cranbury, N.J.), Surfynol CT 121, 131, 141, and 231 (available from Air Products, Allentown, Pa.), and Lemantex Binder (available from Sensient Imaging Technologies S.A., Switzerland).

In such instances, a radical initiator such as a persulfate moiety is used to disproportionate and facilitate the attachment process. In some embodiments, the reaction may be carried out at a temperature of about 25° C. to about 90° C. The particle may be milled to less than about 100 nm before, during, or after reacting the pigment with the substituted triazine. A defoamer may be added as needed to control foaming. Dye solutions and/or surfactants may be used as needed for wetting the particle.

Examples of additives include, without limitation, sublimable UV absorbers such as 2-[2-hydroxy-5-methyl-3-(t-butyl)phenyl]-5-chloro-2H-benzotriazole, sublimable optical brighteners such as benzo-oxazole derivates, Hostalux KCB (Clariant), and combinations thereof.

In some instances, prior to the creation of the self-dispersing particles, the particles may be wetted and milled to nano sized particles and dispersed using a grinding aid and/or a polymeric resin. The particle may be in powder or wet cake form prior to milling with the aid of a grind aid and/or polymeric resin. The milling may take place prior to, at any point during, or after the reaction with the substituted reactive intermediate or additional polymer. After the attachment reaction is complete, unattached grind-aid/resin may be removed using purification methods that are known to those skilled in the art, forming a dispersion containing primarily the self-dispersing particle with attached substrates and water. Examples of grind aids include, but are not limited to Triton X-100 (available from Ashland Inc., Dublin, Ohio), Igepal CA-630 (available from Rhodia, Cranbury, N.J.), Surfynol 104, CT 121, 131, 141, and 231 (available from Air Products, Allentown, Pa.), Efka (available from CIBA Specialty chemicals, Switzerland), Simulsol (available from Seppic, France), various anionic grinding aids such as, without limitation, lignosulfonates from Mead Westvaco, Borregaard and sulfonates of naphthalenic acid-formaldehyde condensates from Nufarm, Rohm & Haas.

In one example of the second embodiment, reactive compounds comprising cyanuryl groups are substituted with a secondary compound that comprises organic groups. The substituted reactive intermediate —X—S-ZM is then attached to a particle by using cyanuric chloride. The combination of pH, reaction temperature, and duration determine how many groups are attached to the surface of the particle. In one embodiment, the reaction is carried out with 15 grams of 4-aminobenzoic acid and 29.6 grams per 30 grams of particle.

In some embodiments, a slurry of a secondary compound that comprises an organic group, cyanuric chloride, water, ice, and base is created. The secondary compound that comprises an organic group may be selected by the desired end application for the particle.

In an example of the third embodiment, reactive compounds comprising cyanuryl groups are substituted with a secondary compound that comprises two organic groups, which may be the same or different. The two substituted reactive intermediates X—S-ZM and X—S2-Z2M2 are then attached to a particle by using the cyanuric chloride. The combination of pH, reaction temperature, and duration determine how many groups are attached to the surface of the particle. This process can be done sequentially by first reacting with a slurry of secondary compound that comprises an organic group, cyanuric chloride, water, ice, and base. A second slurry of a different secondary compound that comprises an organic group, cyanuric chloride, water, ice, acid, and base is used to complete the sequence.

The ratio of cyanuryl chloride to secondary compound is typically determined by stoichiometry and the concentration is controlled to allow for good mixing. Reaction between the cyanuric chloride and the secondary compound may occur for a period of about 2 hours to about 4 hours with mixing.

In an example of the third embodiment, all the reactive chlorines in cyanuryl chloride are displaced by the secondary compound or a mixture of secondary compounds by manipulating the stoichiometry (three equivalents to displace all three chlorines) and temperature (a higher temperature of about 90° C.) prior to the reaction with a particle. This reaction forms a substituted triazine, which facilitates the surface modification of the particle. The mixture of secondary compounds may include one, two, or three different secondary compounds. In such instances, a radical initiator such as a persulfate moiety is used to disproportionate and facilitate the attachment process.

In some embodiments of the present invention, a radical initiator such as a persulfate moiety is used to disproportionate and facilitate the attachment process. In some embodiments, the reaction may be carried out at a temperature of about 25° C. to about 90° C., particularly about 40° C. to about 60° C. The particle may be milled to less than about 100 nm before, during, or after reacting the particle with the substituted triazine. The particle may be milled for about 2 to about 20 hours, particularly about 4 to about 15 hours, more particularly about 7 to about 11 hours. A defoamer may be added as needed to control foaming.

Reaction of the particles with reactive compounds or secondary groups that include acid derivatives may create acidic surface groups that can lower the pH of the reaction mixture. A decrease in pH may result in a destabilization of the self-dispersing particle dispersion or slurry of reactive compound and secondary compound during the substitution and may also result in an increase in viscosity. Therefore, the pH may be adjusted, as needed, before and during the substitution with a basic reagent. The pH of the reaction mixture during substitution may be greater than or equal to about 7, particularly greater than or equal to about 8, and more particularly greater than or equal to about 9. The pH may be adjusted by any known method in the art including, for example, the addition of base. Suitable bases may include, but are not limited to, alkali hydroxides and calcium-free alkali hydroxides (e.g., NaOH, KOH, LiOH, $NH_4OH$), alkali carbonates and bicarbonates (e.g., $NaHCO_3$, $KHCO_3$), and organic bases (e.g., dimethylethanol amine and triethanol amine). In particular, a suitable pH adjuster comprises calcium free sodium hydroxide.

Self-Dispersing Particle

After the reactions described above are complete, the self-dispersing particle may be isolated from the reaction mixture as a dry powder. The resultant self-dispersing particle may be purified by using any number of techniques known to those skilled in the art to remove unreacted raw materials, byproduct salts and other reaction impurities. Purification techniques may include, but are not limited to, filtration, centrifugation, or a combination of the two. The self-dispersing particle may also be isolated, for example, by evaporation or it may be recovered by filtration and drying using techniques known to those skilled in the art.

Alternatively, the self-dispersing particle may be delivered as concentrated aqueous particle dispersion. Dispersions of the self-dispersing particles of the present invention may be purified to remove organic and inorganic impurities and other undesirable free species which can co-exist in the dispersion as a result of the manufacturing process. Purification techniques may include, but are not limited to, water washing, reverse osmosis, and ultrafiltration. In some embodiments, dissolved impurities may be removed by ultrafiltration until the chloride and sulfate content of the feed sample adjusted to 10% solids is less than about 150 ppm, particularly less than about 100 ppm, and more particularly less than about 25 ppm. If necessary, the pH of the dispersion may be adjusted prior to purification. A sufficient amount of acid or base may be added to adjust the pH of the dispersion to at least about 7, particularly to at least about 8, and more particularly to at least about 9. This includes embodiments where the pH of the dispersion is about 7 to about 9. The dispersion may be concentrated if desired by removal of some of the water. In some embodiments, the dispersion is concentrated to at least about 8% solids, in others to at least about 14% solids, and in yet others to at least about 20% solids. This includes embodiments where the dispersion is concentrated to about 8% to about 16% solids. In other embodiments, the dispersion is concentrated to at least about 10% solids, in others to at least about 18% solids, and in yet others to at least about 20% solids. This includes embodiments where the dispersion is concentrated to about 8% to about 14% solids.

A biocide may also be added to the dispersion to inhibit the growth of microorganisms. Examples of suitable biocides include, but are not limited to, sodium benzoate, pentachlorophenol sodium, 2-pyridinethiol-1-oxide sodium, sodium sorbate, sodium dehydroacetate, benzisothiazolinone, 1,2-dibenzothiazolin-3-one, methylisothiazolinone, chloromethylisothiazolinone, and 1-(3-chlorallyl)-3,5,7-triaza-1 azoniaadamantane chloride (CTAC). Commercially available biocides include Proxel® CRL, Proxel® BDN, Proxel® GXL, Proxel® XL-2, and Proxel® TN (available from Arch Chemicals, Smyrna, Ga.), Nipacide TBX (available from Clariant, Charlotte, N.C.) and XBINX® (available from PMC Specialties Group, Inc., Cincinnati, Ohio). Typically, a small amount, such as 0.05 to 5%, particularly 0.1 to 1%, and more particularly 0.2 to 0.4% by weight of biocide, is used in the dispersion. This includes 0.3% by weight biocide.

Agents may also be added to impart fluidity and stability to the dispersion. Examples of such agents may be found in U.S. Pat. No. 5,059,248 issued Oct. 22, 1991, U.S. Pat. No. 5,591,455 issued Jan. 7, 1997 and U.S. Pat. No. 5,595,592 issued Jan. 21, 1997, each of which is hereby incorporated by reference. Examples include, but are not limited to, linear aliphatic substituted glycine compounds and salts thereof. As used herein, the term "linear aliphatic substituted glycine" designates glycine compounds in which the amino group of glycine has been substituted with linear aliphatic groups. Illustrative of agents of this type which may be used in the practice of the invention are ethylene diamine tetraacetic acid, nitrilo triacetic acid, diethylene triamine pentaacetic acid, hydroxyethylene diamine triacetic acid, dihydroxyethyl glycine, iminodiacetic acid and ethanol diglycine and the alkali metal (e.g., sodium), alkaline earth metal (e.g., calcium) and ammonium salts thereof. Other similar linear aliphatic substituted glycine compounds and salts thereof known to those skilled in the art may also be used. In some embodiments, the aforementioned salts of ethylenediaminetetraacetic acid are used because of their availability, cost effectiveness and nontoxicity. In some embodiments, these agents may constitute approximately 0.5 to 3.5 wt. %, preferably about 1.5 to 2.5 wt. %, of the particle in the dispersion compositions.

The dispersion may be filtered through filter cartridges as required for the designated end use of the dispersion. In some embodiments, the nominal pore size of the filter cartridge is less than or equal to about 5 microns, particularly less than or equal to about 1 micron, particularly less than or equal to about 0.5 micron, and more particularly less than or equal to about 0.2 micron.

In addition to powders and dispersions, the self-dispersing particle may also be isolated as a wet presscake. In presscake form, the self-dispersing particle is not agglomerated to the extent that it is in dry form and thus the self-dispersing particle does not require as much deagglomeration when used, for example, in the preparation of inks.

If desired, the charge-balancing counterions associated with the surface-modifying groups as a result of the attachment/substitution process may be at least partially substituted or changed with the use of suitable base or salt form or exchanged or substituted with other suitable cations using known ion-exchange techniques such as ultrafiltration, reverse osmosis, conversion to acid form as an intermediate and the like. Examples of counterions include, but are not limited to, alkaline earth metal ions, alkali metal ions (e.g., $Na^+$, $K^+$ and $Li^+$), $NR_1R_2R_3H^+$, and combinations thereof, wherein $R_1$, $R_2$ and $R_3$ may independently be H or $C_1$-$C_5$ alkyl groups that may be unsubstituted or substituted (e.g., tetraethylammonium ion (TEA), tetramethylammonium ion (TMA), monoethanolammonium ion, triethanolammonium ion, tetrabutylammonium ion, etc).

Properties of Self-Dispersing Particles

The self-dispersing particle may exhibit at least one of long-term and high temperature stability and have a particle size distribution suitable for use in high speed jetting applications. Compared to more conventional systems, the dispersions containing the self-dispersing particles may be more robust and stable. This provides advantages in terms of at least one of product reliability (for example, for piezoelectric and thermal print heads), smaller influence of raw material purity, improved stability against storage, transportation thermal conditions, logistics (providing the possibility of manufacturing larger batches), and cost management. When the surfaces are modified through covalent bonding they may behave like a self dispersed pigment. One notable difference is the sublimability of some of these dyes even after such modification which finds great use in the sublimation printing market. The surface modifications may be carried out in an aqueous environment making the product and the process eco friendly.

The self-dispersing particle may possess the following properties. The percent of solids in the self-dispersing particle may be from about 5% to about 30%, particularly from about 7% to about 20%.

The pH of the self-dispersing particle dispersion may be from about 6 to about 10, particularly about 7 to 9.

The viscosity of the self-dispersing particle dispersion may be from about 2 to about 30 cps, particularly about 3 to about 20 cps.

The surface tension of the self-dispersing particle dispersion may be from about 35 to about 70 dynes/cm.

Applications of Self-Dispersing Particles

The self-dispersing particle according to the present invention may be used in a number of end use applications. These uses include, but are not limited to, coatings, metal coatings, paints, papers, adhesives, latexes, toners, textiles, fibers, plastics (flexible films and bulk materials), inks, and ink jet inks. The self-dispersing particles according to the present invention may also be used in cosmetic applications, such as, without limitation, mascaras, eye liners, oil-in-water and water-in-silicone dispersions, aqueous nail polish, and hair coloring or hair dyes. The self-dispersing particles according to the present invention may additionally be used in writing instruments (e.g., pens, markers) and in correction fluids.

Specific examples include, without limitation, printing ink for paper, textiles, polyesters, fibers, plastics (flexible films and bulk materials), metals, metal deco and plastics, UV curing, wood stains, writing instruments, felt pens for writing or drawing, sublimation printing on man-made fibers, coated natural fibers, coated materials, plastics, coated hard substrates, and color filters. In one example, an inkjet ink incorporating a particle of the present invention may be useful in high quality prints in an inkjet photo printer. The self-dispersing particles produced by the process of the invention are particularly well-suited for use in sublimation printing applications, transfer applications, and direct printing applications. Examples of transfer printing are disclosed in U.S. Pat. Nos. 4,406,662, 4,713,081, 5,246,518, 5,248,363, 5,302,223, 7,001,660, Great Britain Patent No. 1527396 and European Patent No. 1533347, which are herein incorporated by reference in their entireties. Further examples of other printing and application techniques are disclosed in U.S. Pat. Nos. 7,001, 649, 6,961,076, 6,840,614, 6,686,314, 6,631,984, 6,540,345, 6,488,370, 6,486,903, 6,450,098, 6,447,629, 6,439,710, 6,425,331, 6,402,313, 6,341,856, 6,152,038, 6,103,041, 5,830,263, 5,746,816, 5,734,396, 5,642,141, 5,640,180, 5,601,023, which are herein incorporated by reference in their entireties. Explanations of textile printing may be found in *Textile Printing*, LCW Miles, Second Edition, 1994, chapter 3.2, which is herein incorporated by reference in its entirety.

Sublimation transfer depends on the use of a sublimable dye in the printed design. When a printed substrate (paper, film, etc.) is heated, the dye molecules leave the substrate and go into the vapor phase. If the heated paper has been previously put in contact with an appropriate receiving material (fabric, coated surface, plastic, etc), the dye molecules are preferentially adsorbed on the surface of the receiving material. If the substrate has been heated properly, and if the dye has an affinity to the material, the dye molecules diffuse into the warm substrate and are then dissolved in it.

Further examples of end use applications include, without limitation, applications on flexible substrates. For instance, printed flexible film may allow the performance of a 3D sublimation transfer on an already shaped 3D object. Another example of an end use application includes, without limitation, outdoor architectural coatings. Sublimation transfers for outdoor architectural coatings may be made on coated metals.

One aspect of the present invention relates to inkjet ink formulations using the self-dispersing particle described above. Inkjet formulations containing such particles may do at least one of the following: 1) provide uniform, bleed-free images with high resolution and high density on print media; 2) not cause nozzle clogging which typically occurs due to drying of the ink at a distal end of a nozzle; 3) rapidly dry on substrate (paper, fabric, film, etc.); 4) demonstrate good long-term storage stability; and 5) demonstrate print characteristics which are independent of the paper quality. Inkjet formulations containing such particles may also provide better ink stability and robustness against fluctuating temperature conditions during transport and storage, which may cause nozzle clogging, banding, and poor print quality.

The ink compositions of the present invention may be prepared by combining the above self-dispersing particles with an aqueous vehicle and any other suitable components, some of which are discussed below. The amount of self-dispersing particle (by weight) in the ink composition is at least about 0.1%, particularly at least about 10%, and more particularly at least about 20%. Furthermore, the amount of self-dispersing particle (by weight) in the ink composition is less than or equal to about 12%, particularly less than or equal to about 8%, and more particularly less than or equal to about 5%. This includes embodiments where the amount of self-dispersing particle (by weight) in the ink composition is present in an amount ranging from about 0.1% to about 12%.

The aqueous vehicle may comprise water or water in combination with one or more water-soluble organic solvents. Water-soluble organic solvents may be combined with water to make up the aqueous vehicle. Water-soluble organic solvents may include alcohols, polyhydric alcohols such as ethylene glycol, glycerine, PEG, ketones and ketone alcohols such as acetone and diacetone alcohol, ethers such as tetrahydrofuran and dioxane, lower alkyl ethers of polyhydric alcohols, such as ethylene glycol monomethyl (or monoethyl) ether, nitrogen-containing solvents such as pyrrolidone, N-methyl-2-pyrrolidone, sulfur-containing solvents such as thiodiethanol, sugars and derivatives thereof such as glucose, an oxyethylene adduct of glycerin; and an oxyethylene adduct of diglycerin. The water-soluble organic solvents may be used alone or in combination. If a mixture of water and a water-soluble organic solvent is used, the amount of water-soluble organic solvent (by weight) in the ink composition is at least about 5%, particularly at least about 15%, and more particularly at least about 25%. Furthermore, the amount of water-soluble organic solvent (by weight) in the ink composition is less than or equal to about 50%, particularly less than or equal to about 40%, and more particularly less than or equal to about 25%. This includes embodiments where the amount of water-soluble organic solvent (by weight) in the ink composition is about 5% to about 30%. The amount of water in the ink composition is at least about 40%, particularly at least about 50%, and more particularly at least about 60%. Furthermore, the amount of water (by weight) in the ink composition is less than or equal to about 90%, particularly less than or equal to about 80%, and more particularly less than or equal to about 70%. This includes embodiments where the amount of water (by weight) in the ink composition is about 40% to about 80%.

Components may be incorporated into the aqueous vehicle to impart any number of desired properties, such as might be needed to adapt the ink to the requirements of a particular inkjet printer or to provide a balance of light stability, smear resistance, viscosity, surface tension, coating penetration, optical density, color depth, adhesion, highlighter resistance or crust resistance. Penetrants, for example, may be added to reduce bleed, improve wetting of the print media, and otherwise improve overall performance of the print image. Examples of penetrants may include, but are not limited to, alkyl alcohols having 1 to 4 carbon atoms, such as ethanol, glycol ethers, such as ethylene glycol monomethyl ether, diols such as 1,2-alkyl diols, formamide, acetamide, dimethylsulfoxide, sorbitol and sulfolane. The penetrants may be used alone or in combination. The amount of penetrant (by weight) in the ink composition ranges from 0% to about 60%, particularly from about 2% to about 40%, and more particularly from about 5% to about 20%. This includes embodiments where the amount of penetrant (by weight) in the ink composition is present in an amount ranging from about 10% to about 15%.

Surfactants may be added to the aqueous medium to reduce the surface tension of the ink composition. The surfactants may be anionic surfactants, non-ionic surfactants and/or cationic surfactants. Suitable surfactants may include those listed below and in U.S. Pat. No. 5,116,409 issued May 26, 1992, U.S. Pat. No. 5,861,447 issued Jan. 19, 1999, and U.S. Pat. No. 6,849,111 issued Feb. 1, 2005, each of which is hereby incorporated by reference.

Surfactants are commercially available under various well-known trade names, such as the PLURONIC® series (BASF Corporation, Parsippany, N.J.), the TETRONIC® series (BASF Corporation, Parsippany, N.J.), the ARQUAD® series (Akzo Chemical Inc., Chicago, Ill.), the TRITON® series (Union Carbide Corp., Danbury, Conn.), the SURFONIC® series (Texaco Chemical Company, Houston, Tex.), the ETHOQUAD® series (Akzo Chemical Inc., Chicago, Ill.), the ARMEEN® series (Akzo Chemical Inc., Chicago, Ill.), the ICONOL® series (BASF Corporation, Parsippany, N.J.), the SURFYNOL® series (Air Products and Chemicals, Inc. Allentown, Pa.), and the ETHOMEEN® series (Akzo Chemical Inc., Chicago, Ill.), to name a few.

The surfactants may be used alone or in combination. The amount of surfactant (by weight) in the ink composition may range from 0% to about 10%, particularly from about 0.1% to about 10%, and more particularly from about 0.3% to about 5%. This includes embodiments where the amount of surfactant (by weight) in the ink composition may range from about 0.1% to about 8%.

One or more humectants may be added to the aqueous vehicle to prevent clogging, caused by drying out during periods of latency, of inkjet nozzles. Humectants may be selected from materials having high hygroscopicity and water-solubility. Examples of humectants include, but are not limited to, polyols such as glycerol, lactams such as 2-pyrrolidone, urea compounds such as urea, 1,3-dimethylimidazolidinone, saccharides such as sorbitol, 1,4-cyclohexanedimethanol, 1-methyl-2-piperidone, N-ethylacetamide, 3-amino-1,2-propanediol, ethylene carbonate; butyrolactone and Liponic EG-1. There are no particular limitations on the amount used of the humectant, but in general the amount of humectant (by weight) in the ink composition may range from 0% to about 30%, particularly from about 1% to about 15%, and more particularly from about 5% to about 10%.

Polymers may be added to the ink composition to improve the water-fastness, rub and lightfastness of the images on print media. Suitable polymers may include, but are not limited to, polyvinyl alcohol, polyester, polyestermelamine, styrene-acrylic acid copolymers, styrene-maleic acid copolymers, styrene-maleic acid-alkyl acrylate copolymers, styrene-metacrylic acid copolymers, styrene-methacrylic acid-alkyl acrylate copolymers, styrene-maleic half ester copolymers, vinyl-naphthalene-acrylic acid copolymers, vinyl naphthalene-maleic acid copolymers and salts thereof. The amount of polymer (by weight) in the ink composition may range from 0% to about 10%, particularly from about 0.1% to about 6%, and more particularly from about 0.2% to about 4%. This includes embodiments where the amount of polymer (by weight) in the ink composition may range from about 0.1% to about 5.0%.

Ink compositions of the present invention may be buffered to a desired pH using any number of pH modifiers. Suitable pH modifiers may include alkali hydroxides, alkali carbonates and bicarbonates, triethylamine, dimethylethanolamine, triethanolamine, mineral acids, hydrochloric acid, and sulfuric acid. The pH modifiers may be used alone or in combination. The amount of pH modifier (by weight) in the ink composition may range from 0% to about 3.0%, particularly from about 0.1% to about 2.0%, and more particularly from about 0.5% to about 1.5%. This includes embodiments where the amount of pH modifier (by weight) in the ink composition ranges from about 0.2% to about 2.5%.

Preservatives, such as biocides and fungicides, may also be added to the ink composition. Examples of suitable preservatives include sodium benzoate, pentachlorophenol sodium, 2-pyridinethiol-1-oxide sodium, sodium sorbate, sodium dehydroacetate, benzisothiazolinone, 1,2-dibenzothiazolin-3-one, CTAC, methylisothiazolinone and chloromethylisothiazolinone. Commercially available biocides include UCARCIDE® 250 (available from Union Carbide Company), Proxel® CRL, Proxel® BDN, Proxel® GXL, Proxel® XL-2, Proxel® TN (available from Arch Chemicals, Smyrna, Ga.), Dowicil® (Dow Chemical, Midland, Mich.), Nuosept® (Huls America, Inc., Piscataway, N.J.), Omidines® (Olin Corp., Cheshire, Conn.), Nopcocides® (Henkel Corp., Ambler, Pa.), Troysans® (Troy Chemical Corp., Newark, N.J.), and XBINX® (PMC Specialties Group, Inc., Cincinnati, Ohio). The preservatives may be used alone or in combination. The amount of preservatives (by weight) in the ink composition may range from 0% to about 1.5%, particularly from about 0.05% to about 1.0%, and more particularly from about 0.1% to about 0.3%. This includes embodiments where the amount of preservative (by weight) in the ink composition may range from about 0.05% to about 0.5%.

The ink composition may contain one or more viscosity modifiers. Viscosity modifiers may include rosin compounds, alginic acid compounds, polyvinyl alcohol, hydroxypropyl cellulose, carboxymethyl cellulose, hydroxyethyl cellulose, methyl cellulose, salts of polyacrylic acid, polyvinyl pyrrolidone, gum arabic and starch, HEUR (hydrophobic ethoxylated urethanes), HASE (hydrophobically modified alkali swellable emulsions), ASE (alkali swellable emulsions), and combinations thereof. The amount of viscosity modifier (by weight) in the ink composition may range from 0% to about 10%, particularly from about 0.5% to about 8%, and more particularly from about 1% to about 5%. This includes embodiments where the amount of viscosity modifier (by weight) in the ink composition may range from about 1% to about 7%.

Other components which may be incorporated into the aqueous vehicle may also include antioxidants, ultraviolet absorbers, chelating agents, electric conductivity adjusters, viscosity modifiers, oxygen absorbers, anti-kogation agents, anti-curling agents, anti-bleed agents, defoamers, and buffers. The ink compositions of the present invention may contain one or more colorants in addition to the dye particle dispersion of the present invention.

The ink compositions of the present invention are particularly suited for use as an ink composition for inkjet printing wherein droplets of the ink composition are ejected from a printing apparatus and deposited onto a substrate to generate an image. Suitable printing apparatus include, but are not limited to, Continuous Ink Jet (CIJ), prop-on-Demand Valve (DoD Valve), prop-on-Demand Piezo-Electric (DoD Piezo) and Thermal Ink Jet (TIJ). Similarly, any suitable substrate may be employed including plain papers, bonded papers, coated papers, transparency materials, textile materials, plastics, polymeric films and inorganic substrates. However, it should be recognized by those skilled in the art that the above ink compositions may also have use in other applications including, but not limited to, general writing utensil applications and stamp applications.

Textile Printing (by Sublimation and Direct Printing)

Another aspect of the present invention relates to aqueous formulations using the self-dispersing particle described above in textile printing applications. Textile printing formulations containing particles of the present invention may exhibit at least one of the following properties: 1) accepted fastnesses to textile fabrics such as nylon, polyester, polyacrylic, or blends of the same; and 2) ease of application and fixation.

Transfer on Plastics and Coated Substrates

Another aspect of the present invention relates to aqueous formulations using the self-dispersing particle described above in sublimation transfer printing applications. Sublimation transfer printing formulations containing particles of the present invention may exhibit at least one of the following properties: 1) accepted light fastness to coated materials and plastics (ABS, etc); and 2) ease of application and fixation.

The wash, rubbing, water and light fastness properties of the colored textile may be measured by ISO and AATCC test methods, known to those of skill in the art. The lightfastness of the coated materials and plastics may be measured by ISO and AATCC test methods.

Cosmetic Applications

Another aspect of the present invention relates to formulations using the self-dispersing particles described above in cosmetic applications. Cosmetic applications may include those directed to, without limitation, the face, eyes, lips, hair, skin, and nails. Cosmetic applications may include, without limitation, mascaras, eye liner, spray-on hair mascara, aqueous nail polish, brush-on-brow, eye shadows, lipsticks, blushers and rouge, make-up, foundation, and hair coloring or hair dyes. The self dispersing particle dispersions may be easy to incorporate into any aqueous phase portion of a cosmetic formula as they blend easily with polyols and preservatives. Better compatibility with silicones, esters (such as, without limitation, CCT), waxes (such as, without limitation, carnauba wax), and solvents (such as, without limitation, isododecane) helps in the emulsification and yields stable products. The self-dispersed particles enable a formulator to create a product with higher color strength at equivalent particle load than with use of a conventional particle dispersion using a glycerine-water dispersion. The fluidity of the product allows the formulator the flexibility for even higher particle loads which will enhance the product's pay-off leading to fewer strokes on application.

The properties of mascara comprising self-dispersed particles of the present invention can be evaluated visually by applying the mascara evenly to the skin and comparing it side-by-side with mascaras that do not comprise self-dispersed particles of the present invention.

Coating Applications

Coating formulations containing dispersions of the present application may exhibit high hiding power (e.g., titanium dioxide) or high penetration (e.g., solvent dye in wood and concrete stains), offering ease of application and reduced environmental impact.

EXAMPLES

Exemplary embodiments of the present invention are provided in the following examples. The following examples are presented to illustrate the present invention and to assist one of ordinary skill in making and using the same. The examples are not intended in any way to otherwise limit the scope of the invention.

Example 1a

Example of preparation of a cyanuryl tris adduct with sulfanilic acid.

A solution of sulfanilic acid (114 g) in DI water (310 g), calcium-free sodium hydroxide (32 g) and sodium bicarbonate (55 g) at a pH of 8.5 was added to a stirred mixture of cyanuric chloride (40.2 g, available from Lonza Walkersville, Inc., Walkersville, Md.), ice (570 g) and DI water (480 g) in three stages controlling the temperature <0° C., <3° C. and <10° C., respectively. After the addition, the pH was 7.1 and the reaction mixture was heated to and held at 95-100° C. over 4.5 hours to get 1000 g of a clear liquid.

Example 1b

Example of preparation of a cyanuryl tris adduct with 4-aminophenol.

A clear solution of a cyanuryl tris adduct with 4-aminophenol is prepared by substituting 4-aminophenol for 4-aminobenzoic acid in equivalent amount (72 g) in example 1a.

Example 2

Example of preparation of a cyanuryl tris adduct with 4-aminobenzoic acid ("Tris 4-ABA").

A solution of 4-aminobenzoic acid (90.1 g) in DI water (300 g), calcium-free sodium hydroxide (30 g) and sodium bicarbonate (55 g) at a pH of 7.2 were added to a stirred mixture of cyanuric chloride (40.2 g, available from Lonza Walkersville, Inc., Walkersville, Md.), ice (550 g) and DI water (500 g) in three stages controlling the temperature <0° C., <3° C. and <10° C., respectively. After the addition, the pH was 7.1 and the reaction mixture is heated to and held at 95-100° C. over 5 hours to get 600 g of a clear liquid.

Example 3

Example of converting a water-insoluble dye particle to a self dispersed aqueous dispersion by treatment of cyanuryl tris adduct with 4-aminobenzoic acid.

Disperse Blue 359 (available from Sensient Colors Inc., St. Louis, Mo.) 60 g and 100 g of the Tris 4-ABA reagent described in Example 2 was milled in a Hockmeyer media mill (available from Hockmeyer Equipment Corp., Elizabeth City, N.C.) with 0.2 mm YTZ media (available from Quackenbush Co., Inc., Crystal Lake, Ill.) for 4 hours. During the milling the reaction mixture was heated to 45° C. A solution of 29.6 g potassium persulfate and 9.2 g sodium bicarbonate in hot, 50° C. DI water (300 g) was introduced slowly while the pH was maintained between 7.5 and 9.0 with the addition of calcium free sodium hydroxide (19 g). After the milling, the reaction mixture was heated to 45° C. [Step 1]. The dissolved impurities were removed by ultrafiltration until the chloride and sulfate content of the feed sample were less than 50 ppm. The product was then concentrated to 9.3% solids and mixed with (0.3%, wt/wt) Proxel GXL (available from Arch Chemicals, Smyrna, Ga.). Finally, the product (352 g) was filtered through a 0.7 micron GF filter.

Example 4

Example of milling a water-insoluble dye particle to size with a non ionic grind aid and converting to a self dispersed aqueous dispersion by treatment with cyanuryl tris adduct with 4-aminobenzoic acid.

Disperse Yellow 54 (120 g, available from Sensient Colors Inc., St. Louis, Mo.) was slowly added to a stirred mixture of SURFYNOL® CT-131 (42.8 g, available from Air Products and Chemicals, Inc. Allentown, Pa.) and 140 g of DI water. This mixture was milled with a Hockmeyer media mill (available from Hockmeyer Equipment Corp., Elizabeth City, N.C.) with 0.4 mm YTZ media (available from Quackenbush Co., Inc., Crystal Lake, Ill.). Milling was continued for a total of 21 hours at about 3300 rpm and below 40° C. to get a mean PSD of 145 nm. The mill base was combined with the rinse and heated to 50° C. with good mixing. Slowly an equivalent of 9.9 g of the Tris 4-ABA reagent as described in Example 2 was added without causing particle growth. A solution of 26 g of potassium persulfate and 10 g of sodium bicarbonate in hot (50° C.) DI water (200 g) was introduced slowly while maintaining the pH between 10.5 and 9.0 with the addition of calcium-free sodium hydroxide. Continued heating and mixing to hold the temperature at about 55° C. for 16 hours. The dissolved impurities were removed by ultrafiltration until each of the chloride content and the sulfate content of the feed sample are less than 100 ppm. A solution of EDTA (15 g) as sodium salt was introduced and the purification was continued until most of the EDTA was removed and the salt (as chloride and sulfate) level is below 50 ppm. The particles were agglomerated with a mean PSD of about 250 nm and the dispersion was unstable. The reaction mixture was subjected to a second stage reaction, this time on the mill with 4-ABA Tris reagent (equivalent of 30 g 4-ABA) and 20 g potassium persulfate as described above for a total of 17 hours. The product was once again purified by ultrafiltration to remove the dissolved salts and then concentrated to 12.4% solids and mixed with 0.3%, wt/wt Proxel GXL (available from Arch Chemicals, Smyrna, Ga.). Finally, the product was centrifuged at 10,000 rpm for 5 minutes and filtered through 0.7 micron GF filter.

Examples 5-8

Examples 5-12 were prepared following the same process as set forth above for Examples 4.

TABLE 1

Examples of attaching small molecules to a disperse dye particle via a Tris 4-ABA-Cyanuric adduct.

| Example | Dye | | NaHCO$_3$ | K$_2$S$_2$O$_8$ | 4-ABA equiv-alent | Rxn | Mill |
|---|---|---|---|---|---|---|---|
| [#] | Type | (g) | (g) | (g) | (g) | ° C. | h |
| 5 | DY54 | 120 | 10 | 66 | 39.9 | ~60 | 38.5 |
| 6 | DBr27[1] | 120 | 0 | 30 | 30 | 52 | 33 |
| 7 | DBr27[1] | 129 | 10 | 30 | 36 | ~55 | 40 |
| 8* | DB72[2] | 125 | 0 | 15 | 15 | 52 | 10 |

*Single stage reaction only.
[1]Disperse Brown 27 powder available from Sensient Imaging - Specialty Colors and Inks, Switzerland.
[2]Disperse Blue 72 powder available from Sensient Colors Inc, St. Louis, MO.

Example 9

Glycerol (17 g), BYK024 defoamer (0.4 g, available from BykChemie) and the Tris 4-ABA reagent (125 g), equivalent of 17.5 g of 4-aminobenzoic acid, as described in Example 2 were mixed. The mixture was heated at 55° C. in an attritor mill (available from NETZSCH-Feinmahltechnik GmbH, Selb, Germany). 17.5 g of Disperse Red 60 are added under agitation. The pH was maintained between 8 and 9.5 with the addition of calcium free sodium hydroxide. Potassium persulfate (13.4 g) and sodium bicarbonate (4.2 g) were added under agitation. 17.5 g of Disperse Red 60 (available from Huntsman), Potassium persulfate (13.4 g) and sodium bicarbonate (4.2 g) were added under agitation. 0.5 mm Zirstar (available form Saint Gobain) media mill was added and the milling was done at 55° C. at 1100 rpm. During milling, The pH was maintained between 8 and 9.5 with the addition of calcium free sodium hydroxide. Every hour, 15 g Tris 4-ABA reagent from example #2, 1 g sodium bicarbonate, 3.2 g of potassium persulfate are added. After 10 hours of milling, the mean particle size was 0.2 micron. The dissolved impurities were removed by ultrafiltration. After ultrafiltration the dye concentration of the dispersion was 9%. Dowicil 200 (0.1% wt/wt, available form Dow Chemical) was added to the dispersion. Finally, the product was filtered through a 0.7 micron GF filter.

Example 10

Dispersed Dye Dispersion (example of converting a polymer stabilized dispersion to a self dispersed dye dispersion with cyanuryl tris adduct with 4-aminobenzoic acid).

A polymeric dispersant stabilized 23% concentrate of Blue 770[4] (Disperse Blue 359, available from Sensient Imaging—Specialty Colors and Inks, Switzerland) 312 g, was slowly added to a mixture of 91 g of the Tris 4-ABA reagent described above and 950 g of DI water.

After one hour, the reaction mixture was heated to 54° C. A solution of 33 g potassium persulfate and 10.5 g sodium bicarbonate in hot, 50° C. DI water (200 g) was introduced slowly while the pH was maintained between 7.5 and 9.5 with the addition of calcium free sodium hydroxide. After the addition of potassium persulfate solution, the reaction mixture was held at 55° C. [Step 1], overnight for about 16 hours. The dissolved impurities were removed by ultrafiltration until the chloride and sulfate content of the feed sample were less than 50 ppm. The product was then concentrated to 25% solids and mixed with (0.3%, wt/wt) Proxel GXL (available from Arch Chemicals, Smyrna, Ga.). Finally, the product (413.5 g) was filtered through a 0.7 micron GF filter.

Examples 11-13

TABLE 2

Examples of attaching molecules to a polymeric dispersant stabilized dye particle via a cyanuric adduct with 4-aminobenzoic acid.

| Example | Dye | | $NaHCO_3$ | $K_2S_2O_8$ | 4-ABA equiv-alent | Reaction | |
|---|---|---|---|---|---|---|---|
| [#] | Type | (g) | (g) | (g) | (g) | ° C. | h |
| 11 | DB359[4] | 73.5 | 11.7 | 37.7 | 22.05 | 55 | 22 |
| 12 | DB360[5] | 73.3 | 11.7 | 37.6 | 22 | 55 | 28 |
| 13 | DB72[6] | 74.3 | 11.8 | 38.1 | 22.3 | 55 | 28 |

[4]Disperse Blue 359 [23%] available from Sensient Imaging - Specialty Colors and Inks, Switzerland.
[5]Disperse Blue 360 [24%] available from Sensient Imaging - Specialty Colors and Inks, Switzerland.
[6]Disperse Blue 72 [30%] available from Sensient Imaging - Specialty Colors and Inks, Switzerland.

Examples 14-16

Solvent dyes used in printing and coating applications were similarly surface treated as in example 4.

TABLE 3

Examples of attaching molecules to a solvent dye particle via a cyanuric adduct with 4-aminobenzoic acid.

| Example | Dye | | $NaHCO_3$ | $K_2S_2O_8$ | 4-ABA equiv-alent | Rxn | Mill |
|---|---|---|---|---|---|---|---|
| [#] | Type | (g) | (g) | (g) | (g) | ° C. | h |
| 14* | SB67[7] | 93 | 0 | 10 | 15 | 52 | 12 |
| 15* | SR146[8] | 120 | 0 | 15 | 16.5 | 52 | 21 |
| 16* | SR146[8] | 200 | 0 | 30 | 30 | 52 | 15 |

*Single stage reaction only.
[7]Solvent Blue 67 powder available from Sensient Colors Inc. St. Louis, MO.
[8]Solvent Red 146 powder available from Sensient Colors Inc. St. Louis, MO.

Examples 17-19

Inorganic pigments used in cosmetic applications were similarly surface treated as in example 4.

TABLE 4

Examples of attaching molecules to an inorganic pigment particle via a cyanuric adduct with 4-aminobenzoic acid.

| Example | Dye | | $NaHCO_3$ | $K_2S_2O_8$ | 4-ABA equiv-alent | Rxn | Mill |
|---|---|---|---|---|---|---|---|
| [#] | Type | (g) | (g) | (g) | (g) | ° C. | h |
| 17* | $TiO_2$[9] | 200 | 0 | 30 | 30 | 52 | 12 |
| 18* | $TiO_2$[10] | 200 | 0 | 30 | 30 | 52 | 21 |
| 19* | $Fe_2O_3$[11] | 200 | 0 | 30 | 31 | 52 | 24 |

*Single stage reaction only.
[9]Unipure White LC 981 AS, 28204, Triethoxycaprylylsilane treated TiO2 powder, available from Sensient Cosmetic Technologies LCW, South Plainfield, NJ.
[10]Unipure White LC 981, TiO2 powder, available from Sensient Cosmetic Technologies LCW, South Plainfield, NJ.
[11]Yellow Iron Oxide, available from Rockwood Pigments, St. Louis, MO.

Example 20

The physical properties of the modified dyes from the examples above are set forth in the following tables.

TABLE 5-1

Analytical Results of Dye Dispersions.

| Example | Dye | Solids | pH | Cl | $SO_4$ | Viscosity | Conductivity |
|---|---|---|---|---|---|---|---|
| [#] | Type | (%) | | ppm | ppm | cps | µS |
| 3 | DB359[3] | 9.3 | 7.5 | 9 | 2 | 1.78 | 714 |
| 4 | DB359[3] | 12.6 | 8.0 | 2 | <1 | 1.77 | 1430 |
| 5 | DB359[3] | 11.6 | 8.8 | 7 | 4 | 1.46 | 1580 |
| 6 | DBr27[1] | 9.2 | 8.6 | 14 | 34 | 1.86 | 2510 |
| 7 | DBr27[1] | 9.3 | 9.0 | 17 | 33 | 1.37 | 1800 |
| 8 | DB72[2] | 11.9 | 8.4 | 3 | 13 | 1.66 | 960 |
| 10 | DB359[4] | 24.32 | 8.5 | 5 | 32 | 8.96 | 2180 |

TABLE 5-1-continued

Analytical Results of Dye Dispersions.

| Example [#] | Dye Type | Solids (%) | pH | Cl ppm | SO$_4$ ppm | Viscosity cps | Conductivity μS |
|---|---|---|---|---|---|---|---|
| 11 | DB359[4] | 25.0 | 7.9 | 2 | 4 | 8.6 | 1770 |
| 12 | DB360[5] | 6.23 | 8.0 | 4 | 7 | 1.86 | 1030 |
| 13 | DB72[6] | 15.6 | 8.4 | 6 | 11 | 2.26 | 1407 |
| 14 | SB67[7] | 9.1 | 8.4 | 3 | 2 | 3.13 | 1.221 |
| 15 | SR146[8] | 12.6 | 8.0 | 2 | <1 | 1.77 | 1430 |
| 16 | SR146[8] | 9.7 | 8.8 | 2 | 12 | 1.28 | 1110 |
| 17 | TiO$_2$[9] | 10.6 | 9.3 | 1 | 4 | 1.33 | 1310 |
| 18 | TiO$_2$[10] | 14.2 | 9.3 | 17 | 39 | 2.02 | 1590 |
| 19 | Fe$_2$O$_3$[11] | 11.7 | 9.6 | 14 | 22 | 1.55 | 1187 |

[1]Disperse Brown 27 powder available from Sensient Imaging - Specialty Colors and Inks, Switzerland.
[2]Disperse Blue 72 powder available from Sensient Colors Inc, St. Louis, MO.
[3]Disperse Red 60 powder available from Huntsman
[4]Disperse Blue 359 [23%] available from Sensient Imaging - Specialty Colors and Inks, Switzerland.
[5]DB 360 [24%] available from Sensient Imaging - Specialty Colors and Inks, Switzerland.
[6]DB 72 [30%] available from Sensient Imaging - Specialty Colors and Inks, Switzerland.
[7]Solvent Blue 67 powder available from Sensient Colors Inc. St. Louis, MO.
[8]Solvent Red 146 powder available from Sensient Colors Inc. St. Louis, MO.
[9]Unipure White LC 981 AS, 28204, Triethoxycaprylylsilane treated TiO$_2$ powder, available from Sensient Cosmetic Technologies LCW, South Plainfield, NJ.
[10]Unipure White LC 981, TiO$_2$ powder, available from Sensient Cosmetic Technologies LCW, South Plainfield, NJ.
[11]Yellow Iron Oxide, available from Rockwood Pigments, St. Louis, MO.

TABLE 5-2

Analytical Results of Dye Dispersions.

| Example [#] | Dye Type | Surface tension Dynes/cm | Zeta Potential | D50 nm | Na ppm | K ppm | S ppm | Heavy metals[12] Ppm |
|---|---|---|---|---|---|---|---|---|
| 3 | DB359[3] | 67.7 | −64 | 199 | 212 | 199 | 29 | 100 |
| 4 | DY54 | 37.9 | −67 | 166 | 638 | 96 | 134 | 12 |
| 5 | DY54 | 42 | −66 | 160 | 531 | 88 | 157 | 17 |
| 6 | DBr27[1] | 38.7 | −64 | 250 | 1209 | 159 | 207 | 24 |
| 7 | DBr27[1] | 42 | −60 | 188 | 657 | 87 | 124 | 55 |
| 8 | DB72[2] | 46 | −71 | 153 | 364 | 49 | 142 | 16 |
| 10 | DB359[4] | 45.9 | −64 | 125 | 1056 | 926 | 444 | 241 |
| 11 | DB359[4] | 45.8 | −59 | 130 | 683 | 679 | 157 | 220 |
| 12 | DB360[5] | 51 | −57 | 168 | 355 | 313 | 17553 | 677 |
| 13 | DB72[6] | 37.3 | −58 | 143 | 629 | 82 | 194 | 51 |
| 14 | SB67[7] | 38.4 | −74 | 209 | 1363 | 235 | 6825 | 14 |
| 15 | SR146[8] | 42 | −57 | 159 | 398 | 217 | 82 | 101 |
| 16 | SR146[8] | 39.8 | −70 | 159 | 498 | 55 | 11 | 45 |
| 17 | TiO$_2$[9] | 39 | −71 | 190 | 483 | 176 | 153 | 86 |
| 18 | TiO$_2$[10] | 35.5 | −72 | 217 | 802 | 379 | 127 | 149 |
| 19 | Fe$_2$O$_3$[11] | 36.9 | −70 | 129 | 457 | 77 | 262 | 28* |

*Excluding Iron
[1]Disperse Brown 27 powder available from Sensient Imaging - Specialty Colors and Inks, Switzerland.
[2]Disperse Blue 72 powder available from Sensient Colors Inc, St. Louis, MO.
[3]Disperse Red 60 powder available from Huntsman
[4]Disperse Blue 359 [23%] available from Sensient Imaging - Specialty Colors and Inks, Switzerland.
[5]DB 360 [24%] available from Sensient Imaging - Specialty Colors and Inks, Switzerland.
[6]DB 72 [30%] available from Sensient Imaging - Specialty Colors and Inks, Switzerland.
[7]Solvent Blue 67 powder available from Sensient Colors Inc. St. Louis, MO.
[8]Solvent Red 146 powder available from Sensient Colors Inc. St. Louis, MO.
[9]Unipure White LC 981 AS, 28204, Triethoxycaprylylsilane treated TiO$_2$ powder, available from Sensient Cosmetic Technologies LCW, South Plainfield, NJ.
[10]Unipure White LC 981, TiO$_2$ powder, available from Sensient Cosmetic Technologies LCW, South Plainfield, NJ.
[11]Yellow Iron Oxide, available from Rockwood Pigments, St. Louis, MO.
[12]Sum of Ca, Mg, and Fe present as a contaminant in the raw materials and/or formed during the milling process.

Example 21

X-Ray Photoelectron Spectroscopy ("XPS") Analyses

XPS data were collected and analyzed for samples identified by example number in table 6.

TABLE 6

XPS of particle samples.

| Sample | Sample ID | Source |
|---|---|---|
| 1 | [—] [DB359] | |
| 2 | [3] [DB359] | Dispersion from Example 3 with 4-ABA attachment |
| 3 | [9] [DB359] | Dispersion from Example 9 with 4-ABA attachment |
| 4 | [10] [DB359] | Dispersion from Example 10 with 4-ABA attachment |
| 5 | [—] [DY54] | |
| 6 | [5] [DY54] | Dispersion from Example 4 with 4-ABA attachment |
| 7 | [—] [DBr27] | |
| 8 | [7] [DBr27] | Dispersion from Example 6, with 4-ABA attachment |
| 9 | [—] [SR146] | |

TABLE 6-continued

XPS of particle samples.

| Sample | Sample ID | Source |
|---|---|---|
| 10 | [16] [SR146] | Dispersion from Example 16 with 4-ABA attachment |
| 11 | [—] [DB72] | |
| 12 | [8] [DB72] | Dispersion from Example 8 with 4-ABA attachment |
| 13 | [—] TiO$_2$ | |
| 14 | [—] TiO$_2$ Treated | |
| 15 | [17] [TiO$_2$] | Dispersion from Example 17 with 4-ABA attachment |
| 16 | [18] [TiO$_2$] | Dispersion from Example 18 with 4-ABA attachment |
| 17 | [—] [Fe$_2$O$_3$] | |
| 18 | [19] [Fe$_2$O$_3$] | Dispersion from Example 19 with 4-ABA attachment |
| 19 | [—] [SB 67] | |
| 20 | [14] [SB 67] | Dispersion from Example 14 with 4-ABA attachment |

The XPS data were acquired by EAG Labs (in Chanhassen, Minn.) using a probe beam of focused, monochromatic Al K$_\alpha$, radiation. The x-rays generate photoelectrons that are energy analyzed and counted to reveal the atomic composition and chemistry of the sample surface. The escape depths of 15-35 Å of the photoelectrons limits the depth of analysis to the outer ~50-100 Å. Typically, 95% of the signal originates from within this depth. The data presented includes low resolution survey scans, which give the full spectrum between 0 and 1400 eV binding energy. Also included in the data are high resolution spectra from selected elements, which provide chemical state information. The spectra are used to obtain surface composition by integrating the areas under the photoelectron peaks and applying empirical sensitivity factors. The XPS data are presented in FIGS. 1-21.

TABLE 7

Analytical Conditions.

| Instrument: | Physical Electronics 5802 Multitechnique, Quantum 2000 Scanning XPS |
|---|---|
| X-ray Source: | Monochromatic Al K$_\alpha$ 1486.6 eV |
| Analysis Area: | 1.5 mm × 0.6 mm - 5802, 1.2 mm × 0.2 mm - Quantum 2000 |
| Take-off Angle: | 45° |
| Charge Correction: | C—C, C—H in C1s spectra set to 284.8 eV |
| Charge Neutralization: | Low energy electron and ion floods |

The following tables were normalized to 100% of the elements detected. XPS does not detect H or He. Detection limits are typically between 0.05% and 1.0% for other elements. A dash "-" indicates the element was not detected. Major factors affecting detection limits are the element itself (heavier elements generally have lower detection limits), interferences (can include photoelectron peaks and Auger electron peaks from other elements) and background (mainly caused by signal from electrons that have lost energy to the matrix).

Chemical state assignments for a given element have been made by consulting reference data from the literature. Chemical state assignments must be considered tentative in cases where the available reference data is limited or in cases where similar binding energies are observed for a number of different chemical states. Non-linear least squares (NLLS) curve fitting has been applied to selected high resolution spectra to assist in possible chemical state assignment. Results of the NLLS fits are shown on the individual spectra and Chemistry tables (Tables 8-10). The levels of N, Na, and K present in all samples, except the untreated particle, is a measure of charge groups present either as amino benzoic or surface acidic groups as corresponding sodium salts.

TABLE 8

XPS Surface Concentrations of Disperse Dye Samples (Atomic %).

| [Example] [Particle Type] | C | N | O | Na | S | Si | Ca | Cl | Br | Zr |
|---|---|---|---|---|---|---|---|---|---|---|
| [—][DB359] | 78.7 | 12.4 | 8.8 | 0.1 | — | — | — | — | — | — |
| [3][DB359] | 77.0 | 13.1 | 9.6 | 0.3 | — | — | — | — | — | — |
| [10][DB359] | 77.1 | 6.9 | 15.7 | 0.3 | — | — | — | — | — | — |
| [—][DY54] | 85.5 | 4.0 | 10.5 | — | — | — | — | — | — | — |
| [5][DY54] | 80.1 | 3.9 | 15.2 | 0.7 | — | — | — | 0.1 | — | — |
| [—][DBr27] | 70.1 | 7.7 | 13.7 | — | — | — | — | 8.4 | 0.1 | — |
| [7][DBr27] | 72.8 | 6.6 | 15.2 | 0.1 | — | 0.5 | — | 4.9 | — | 0.03 |
| [—][DB72] | 83.8 | 3.5 | 11.8 | 0.1 | 0.06 | — | 0.4 | 0.4 | | |
| [8][DB72] | 82.0 | 3.4 | 14.2 | 0.4 | — | — | — | — | | |

TABLE 8-1

Carbon Chemistries of DB359 Samples (% of total C).

| [Example] [Particle Type] | C—C,H | C—N/C—O | C=O | Aromatic Shake-up |
|---|---|---|---|---|
| [—][DB359] | 60 | 29 | 6 | 5 |
| [3][DB359] | 58 | 26 | 11 | 5 |
| [10][DB359] | 55 | 39 | 4 | 2 |

TABLE 8-2

Carbon Chemistries of DY54 Samples (% of total C).

| [Example] [Particle Type] | C—C,H | C—N | C—O | C=O | O—C=O | Aromatic Shake-up |
|---|---|---|---|---|---|---|
| [—][DY54] | 74 | 4 | 11 | 4 | 2 | 5 |
| [5][DY54] | 67 | 6 | 16 | 6 | 1 | 3 |

TABLE 8-3

Carbon Chemistries of DBr27 Samples (% of total C).

| [Example] [Particle Type] | C—C,H | C—NO2 | C=O | O—C=O | Aromatic Shake-up |
|---|---|---|---|---|---|
| [—][DBr27] | 46 | 46 | 3 | 3 | 2 |
| [7][DBr27] | 51 | 43 | 3 | 2 | 1 |

TABLE 8-4

Carbon Chemistries of DB72 Samples (% of total C).

| [Example] [Particle Type] | C—C,H | C—O/C—N | C=O | O—C=O | Aromatic Shake-up |
|---|---|---|---|---|---|
| [—][DB72] | 69 | 16 | 5 | 2 | 8 |
| [8][DB72] | 65 | 23 | 4 | 2 | 6 |

TABLE 8-5

Nitrogen Chemistries of DB359 Samples (% of total N).

| [Example] [Particle Type] | N—C=N | NH | Aromatic Shake-up |
|---|---|---|---|
| [—][DB359] | 82 | 8 | 10 |
| [3][DB359] | 78 | 11 | 11 |
| [10][DB359] | 84 | 8 | 7 |

TABLE 8-6

Nitrogen Chemistries of DY54 Samples (% of total N).

| [Example] [Particle Type] | C—N? | C2N | NO2 |
|---|---|---|---|
| [—][DY54] | 11 | 85 | 4 |
| [5][DY54] | 14 | 84 | 3 |

TABLE 8-7

Nitrogen Chemistries of DBr27 Samples (% of total N).

| [Example] [Particle Type] | C—N=N—C | C3N | C—NO? | C—NO2 |
|---|---|---|---|---|
| [—][DBr27] | 55 | 14 | 6 | 24 |
| [7][DBr27] | 68 | 13 | 5 | 15 |

TABLE 8-9

Oxygen Chemistries of DB359 Samples (% of total O).

| [Example] [Particle Type] | C=O | C—O | Aromatic Shake-up |
|---|---|---|---|
| [—][DB359] | 64 | 20 | 16 |
| [3][DB359] | 59 | 25 | 16 |
| [10][DB359] | 21 | 77 | 1 |

TABLE 8-10

Oxygen Chemistries of DY54 Samples (% of total O).

| [Example] [Particle Type] | C=O | C—O | Aromatic Shake-up |
|---|---|---|---|
| [—][DY54] | 56 | 40 | 4 |
| [5][DY54] | 32 | 67 | 1 |

TABLE 8-11

Oxygen Chemistries of DB72 Samples (% of total O).

| [Example] [Particle Type] | C=O | C—O | Aromatic Shake-up |
|---|---|---|---|
| [—][DB72] | 43 | 50 | 8 |
| [8][DB72] | 24 | 72 | 4 |

TABLE 9

XPS Surface Concentrations of Solvent Dye Samples (Atomic %).

| [Example] [Particle Type] | C | N | O | Na | S | Cu | Br |
|---|---|---|---|---|---|---|---|
| [—][SB67] | 70.7 | 13.0 | 11.5 | — | 3.8 | 0.9 | — |
| [14][SB67] | 66.9 | 12.1 | 15.0 | 1.0 | 4.0 | 1.0 | — |
| [—][SR146] | 84.8 | 3.3 | 11.7 | — | — | — | 0.1- |
| [16][SR146] | 81.9 | 2.7 | 15.1 | 0.3 | — | — | — |

TABLE 9-1

Carbon Chemistries of SB67 Samples (% of total C).

| [Example] [Particle Type] | C—C,H | N—C=N | CN—Cu | COONa/ CSO3Na | Aromatic Shake-up |
|---|---|---|---|---|---|
| [—][SB67] | 72 | 23 | 2 | 1 | 1 |
| [14][SB67] | 64 | 29 | 4 | 1 | 2 |

TABLE 9-2

Carbon Chemistries of SR146 Samples (% of total C).

| [Example] [Particle Type] | C—C,H | C—O/C—N | C=O | O—C=O | Aromatic Shake-up |
|---|---|---|---|---|---|
| [—][SR146] | 73 | 18 | 2 | 2 | 6 |
| [16][SR146] | 67 | 24 | 2 | 2 | 5 |

TABLE 9-3

Nitrogen Chemistries of SB67 Samples (% of total N).

| [Example] [Particle Type] | N—C=N | CN—Cu | CNSOx | Aromatic Shake-up |
|---|---|---|---|---|
| [—][SB67] | 71 | 17 | 4 | 7 |
| [14][SB67] | 72 | 20 | 2 | 5 |

TABLE 9-4

Oxygen Chemistries of SR146 Samples (% of total O).

| [Example] [Particle Type] | C=O | C—O | Aromatic Shake-Up |
|---|---|---|---|
| [—][SR146] | 39 | 56 | 5 |
| [16][SR146] | 28 | 69 | 2 |

TABLE 10

XPS Surface Concentrations of Inorganic Pigment Samples (Atomic %).

| [Example] [Particle Type] | C | N | O | Na | Si | P | K | Ti | Fe |
|---|---|---|---|---|---|---|---|---|---|
| [—][TiO2] | 15.5 | — | 57.5 | — | — | 2.4 | 2.7 | 22.0 | — |
| [—][TiO2 Treated] | 31.4 | — | 45.5 | — | 3.4 | 1.9 | 1.8 | 16.0 | — |
| [17] [TiO2] | 48.3 | 1.2 | 35.7 | 0.9 | 1.1 | 0.4 | 0.6 | 11.5 | — |
| [18] [TiO2] | 46.1 | 1.1 | 37.4 | 1.1 | — | 0.4 | 0.6 | 13.2 | — |
| [—] [Fe2O3] | 22.2 | — | 53.7 | — | 0.5 | — | — | — | 23.6 |
| [19] [Fe2O3] | 47.3 | 1.1 | 40.5 | 0.9 | — | — | — | — | 10.3 |

TABLE 10-1

Nitrogen Chemistries of Inorganic Pigment Samples (% of total N).

| [Example] [Particle Type] | N—C=N | NH |
|---|---|---|
| [—][TiO$_2$] | — | — |
| [—][TiO$_2$ Treated] | — | — |
| [17] [TiO$_2$] | 44 | 56 |
| [18] [TiO$_2$] | 36 | 64 |
| [—] [Fe$_2$O$_3$] | — | — |
| [19] [Fe$_2$O$_3$] | 40 | 60 |

TABLE 10-2

Oxygen Chemistries of Inorganic Pigment Samples (% of total O).

| [Example] [Particle Type] | Oxide | C=O/Hydroxide | C—O |
|---|---|---|---|
| [—][TiO$_2$] | 73 | 21 | 6 |
| [—][TiO$_2$ Treated] | 64 | 19 | 18 |
| [17] [TiO$_2$] | 63 | 16 | 22 |
| [18] [TiO$_2$] | 65 | 18 | 16 |
| [—] [Fe$_2$O$_3$] | 49 | 44 | 7 |
| [19] [Fe$_2$O$_3$] | 31 | 44 | 25 |

The XPS results as shown in Table 8, indicate that the surface modification as disclosed yields a modified Disperse Blue 359 dye with an increase in surface oxygen and corresponding decrease in nitrogen due to attachment of polymeric material present in the original dispersion. This is further corroborated by the curve fit protocol (FIGS. 2 and 3) showing the additional oxygen is largely Carbon-Oxygen bond type.

Figure 4:
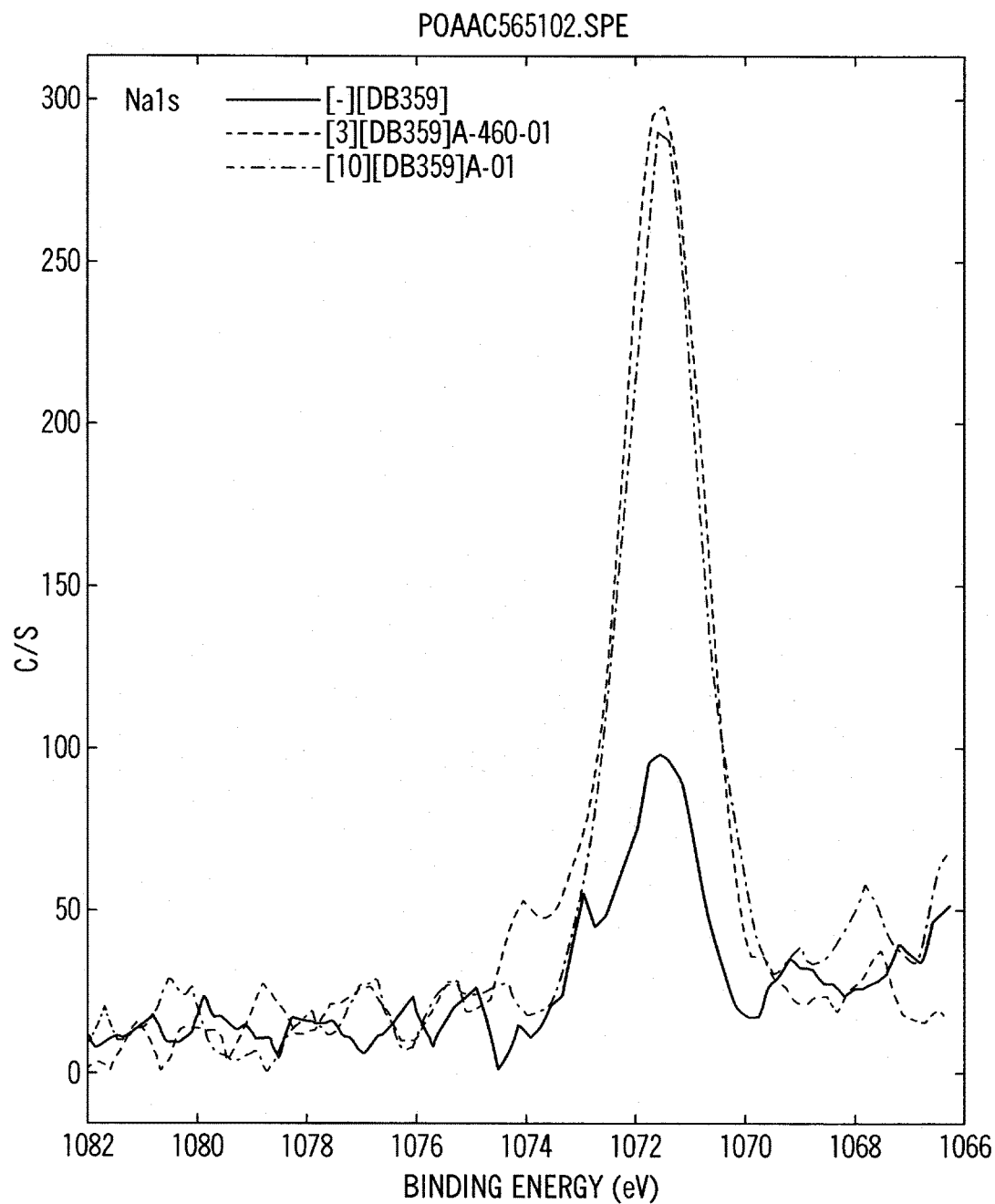
FIG. 4 shows high energy resolution Na1s spectra of Disperse Blue 359 and modified Disperse Blue 359 samples from Examples 3 and 10.
Figure 5:
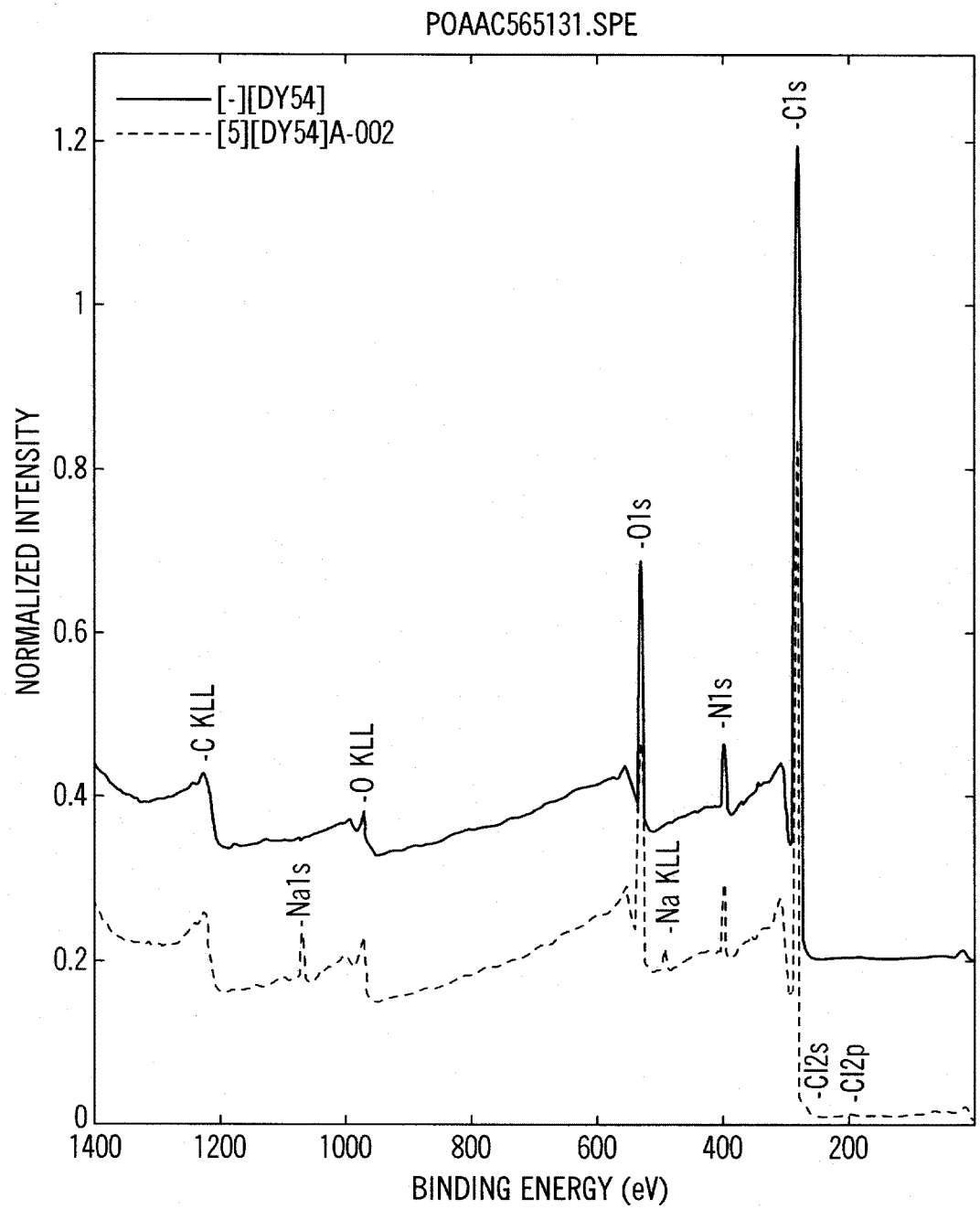
FIG. 5 shows low resolution X-Ray Photoelectron Spectroscopy (XPS) spectra of Disperse Yellow 54 and modified Disperse Yellow 54 sample from Example 5.
Figure 6:
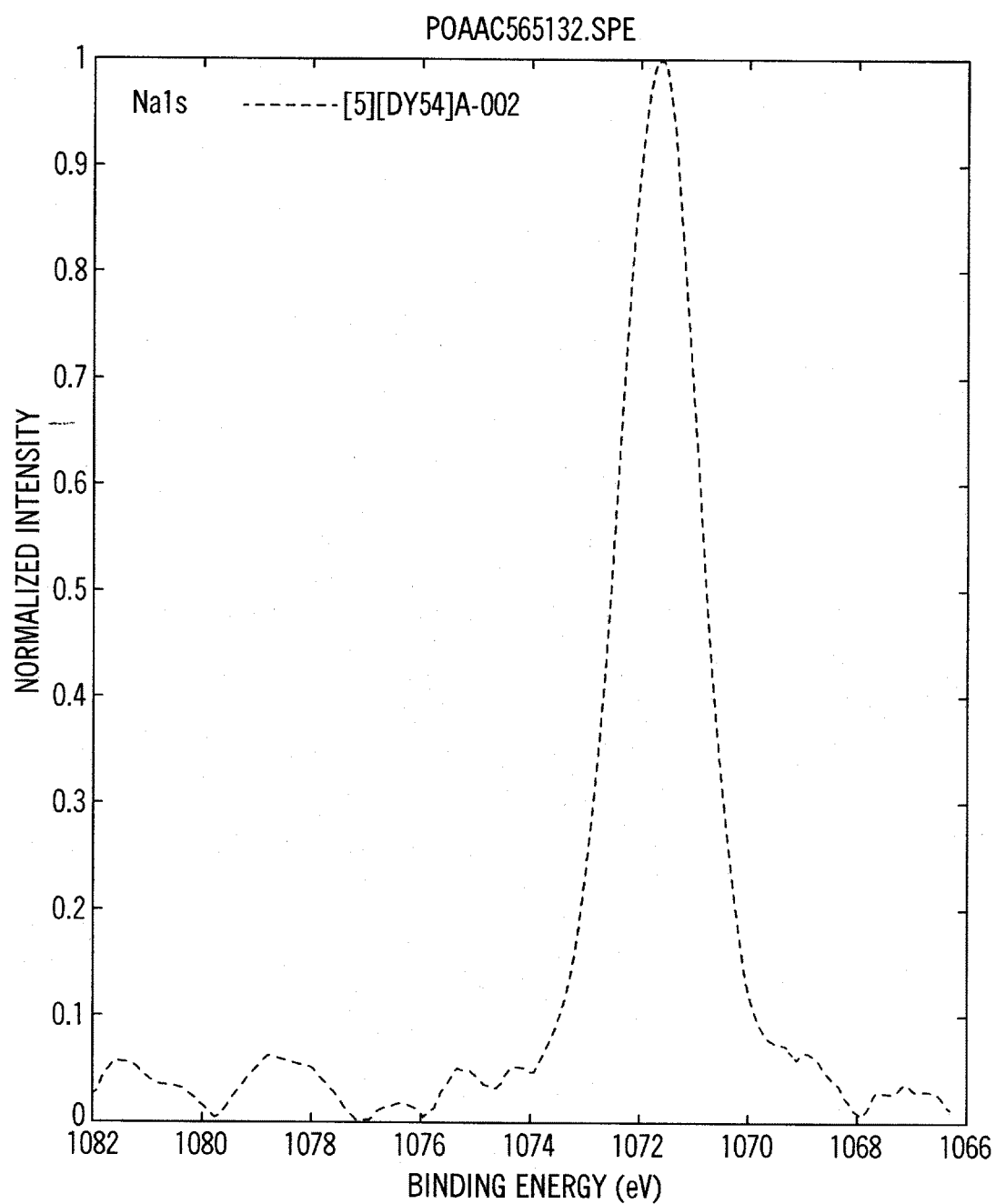
FIG. 6 shows high energy resolution Na1s spectrum of modified Disperse Yellow 54 sample from Example 5.
Figure 7:
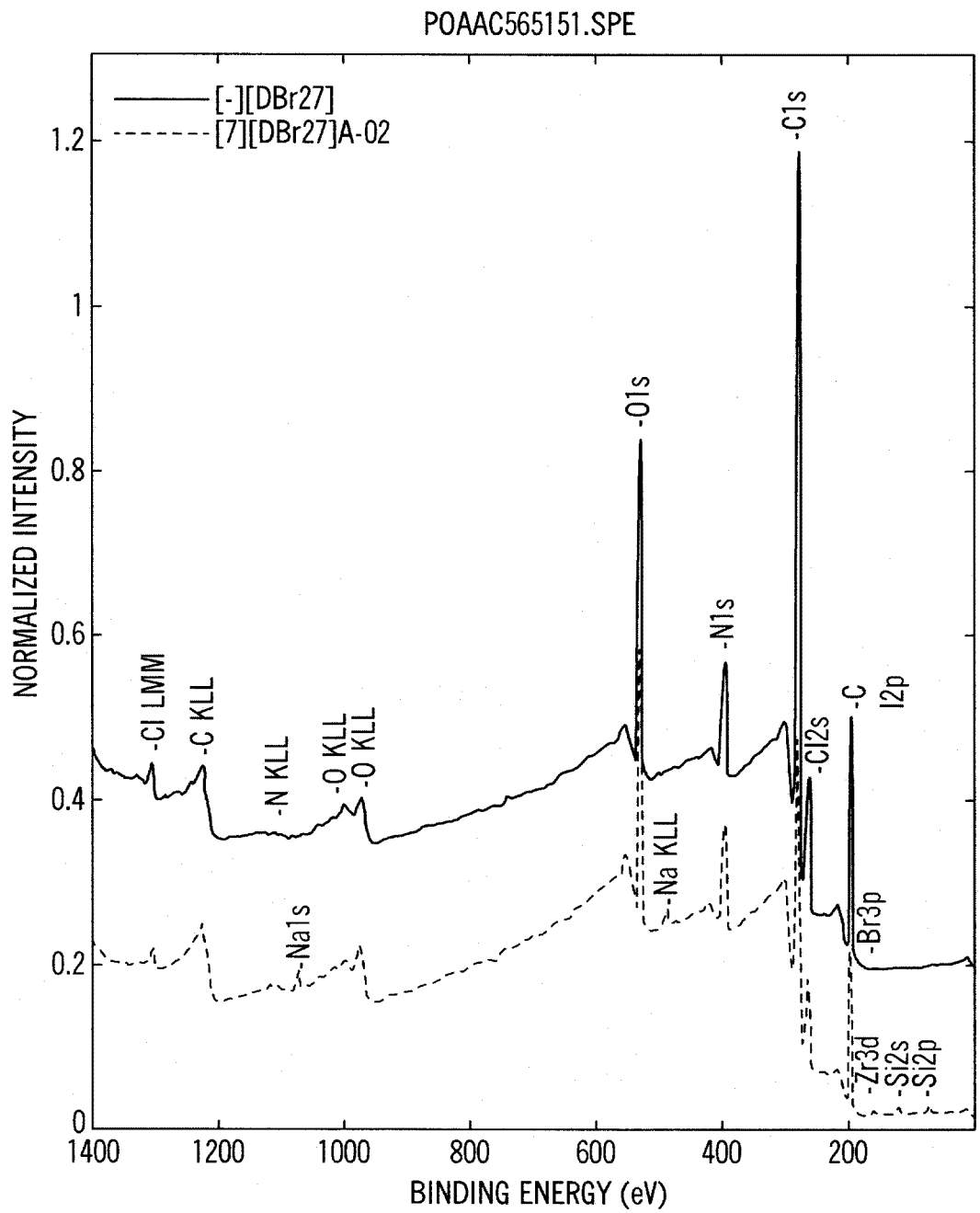
FIG. 7 shows low resolution X-Ray Photoelectron Spectroscopy (XPS) spectra of Disperse Brown 27 and modified Disperse Brown 27 sample from Example 7.
Figure 8:
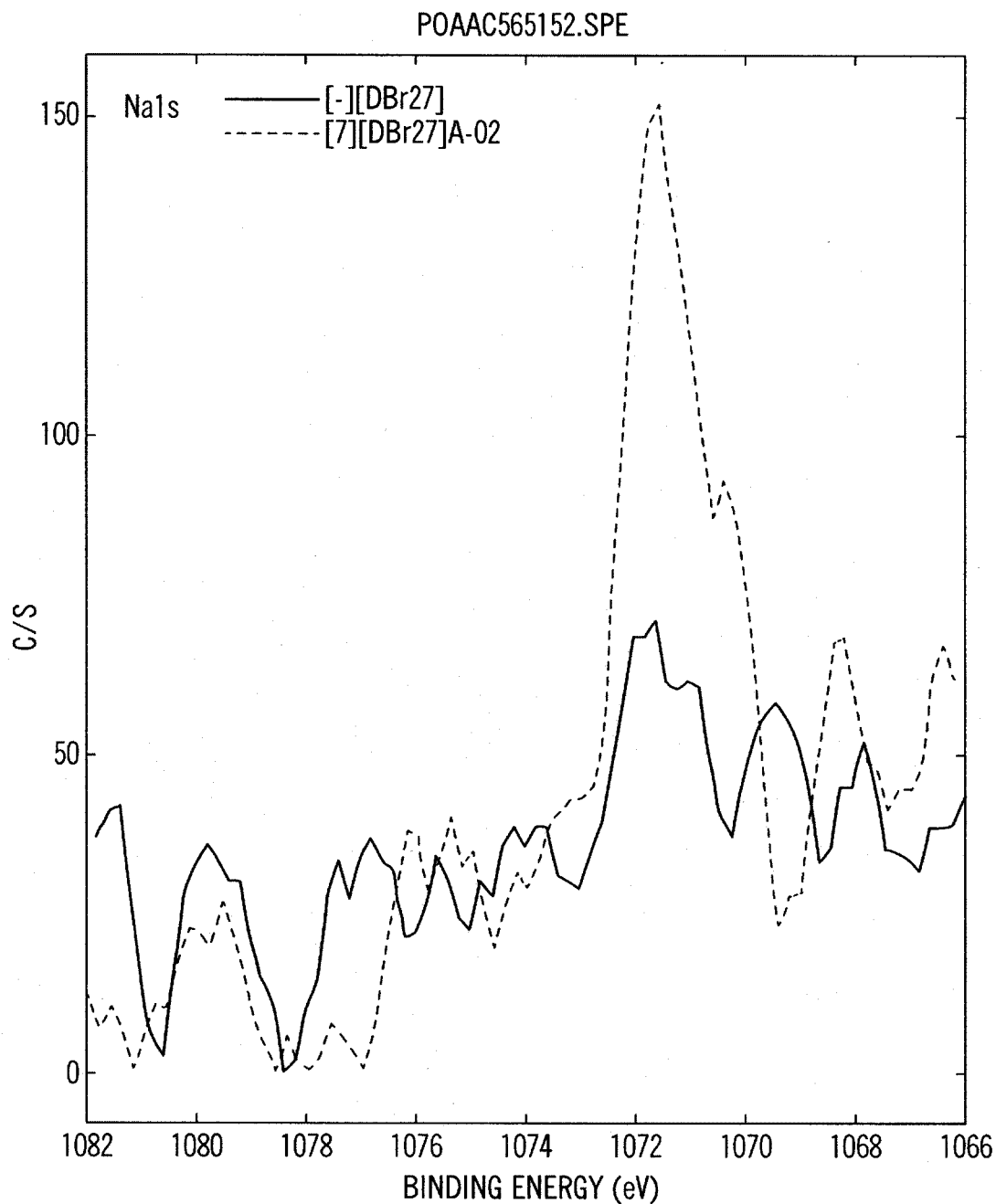
FIG. 8 shows high energy resolution Na1s spectra of Disperse Brown 27 and modified Disperse Brown 27 sample from Example 7.
Figure 9:
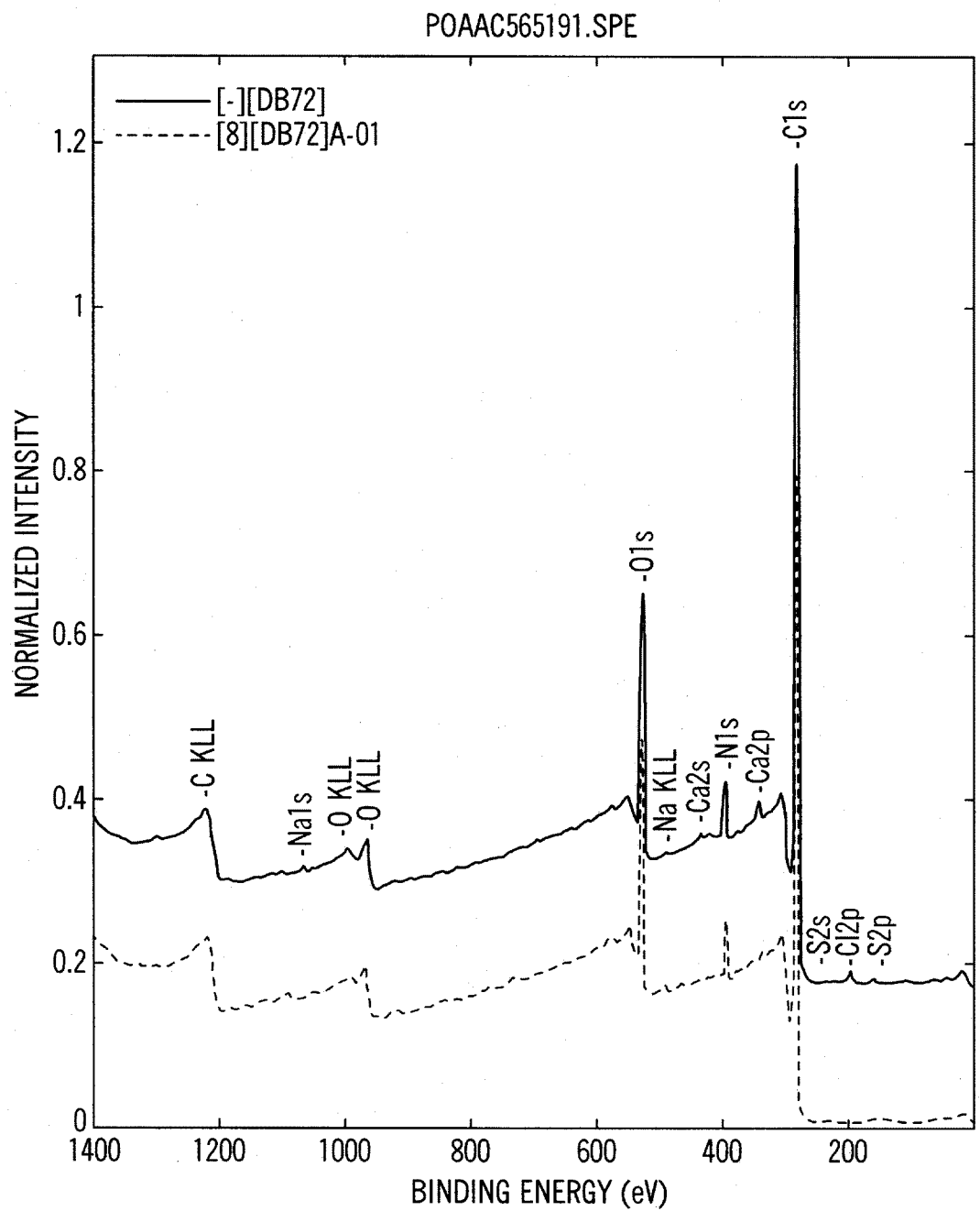
FIG. 9 shows low resolution X-Ray Photoelectron Spectroscopy (XPS) spectra of Disperse Blue 72 and modified Disperse Blue 72 sample from Example 8.
Figure 10:
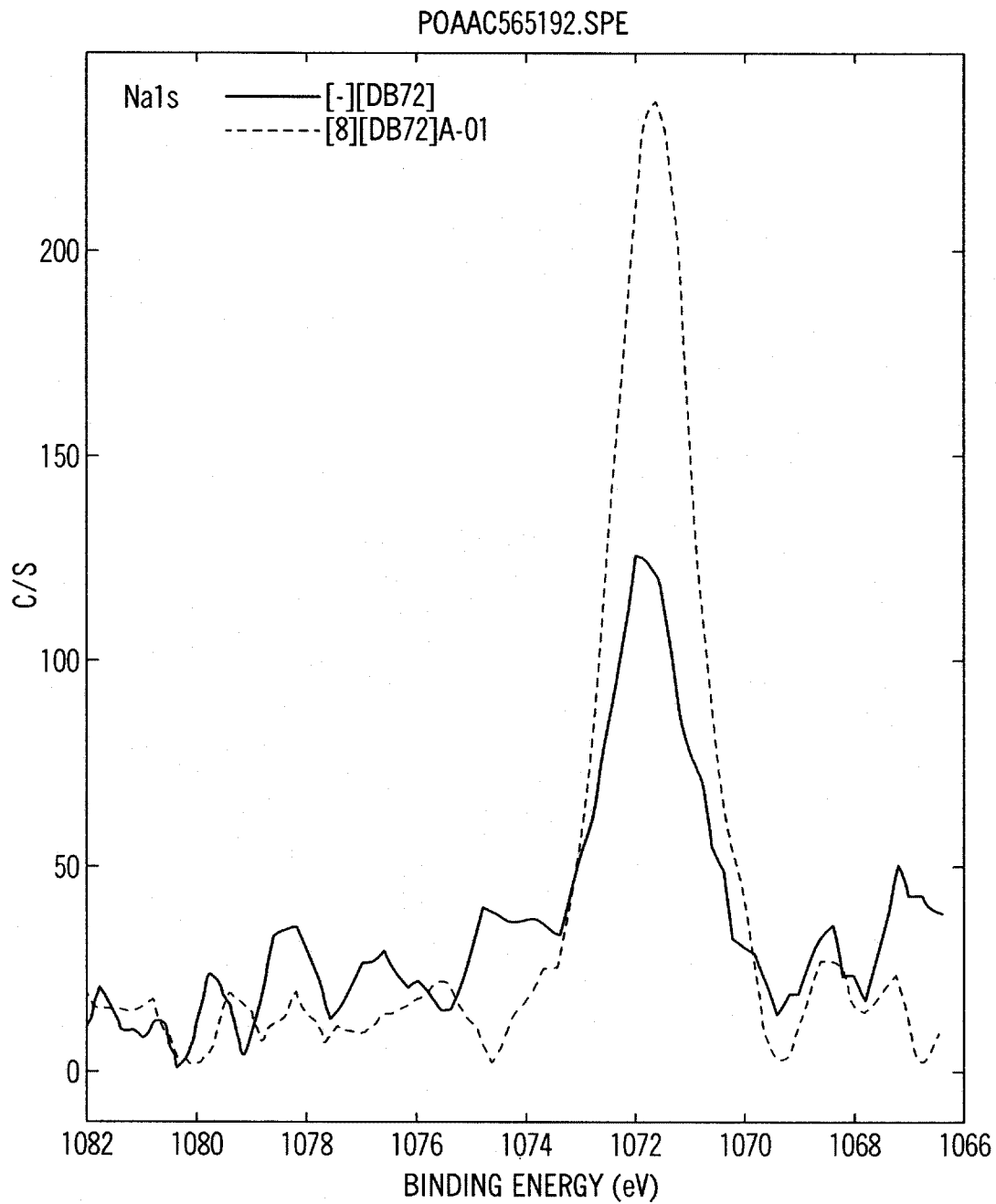
FIG. 10 shows high energy resolution Na1s spectra of Disperse Blue 72 and modified Disperse Blue 72 sample from Example 8.
Figure 11:
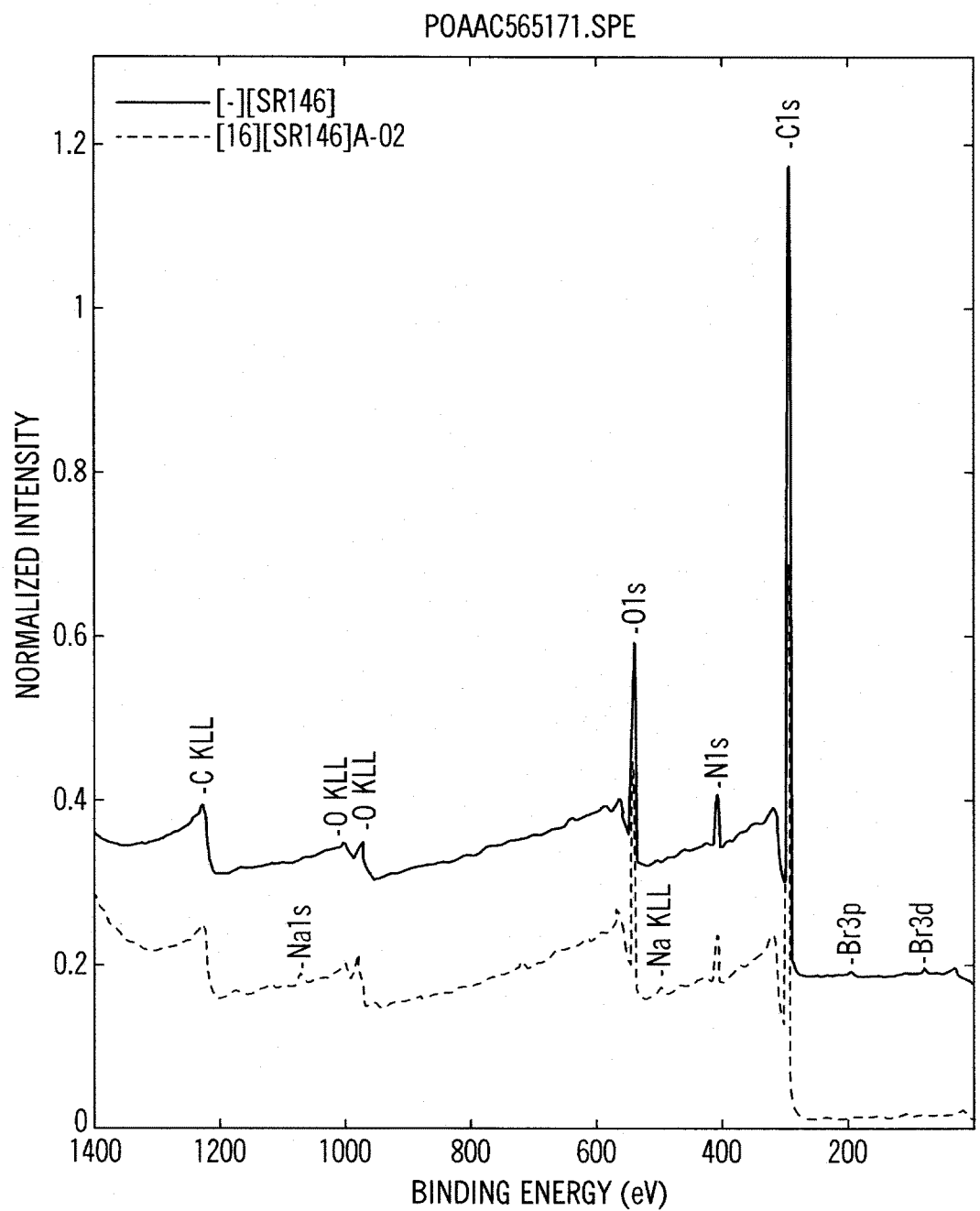
FIG. 11 shows low resolution X-Ray Photoelectron Spectroscopy (XPS) spectra of Solvent Red 146 and modified Solvent Red 146 sample from Example 16.
Figure 12:
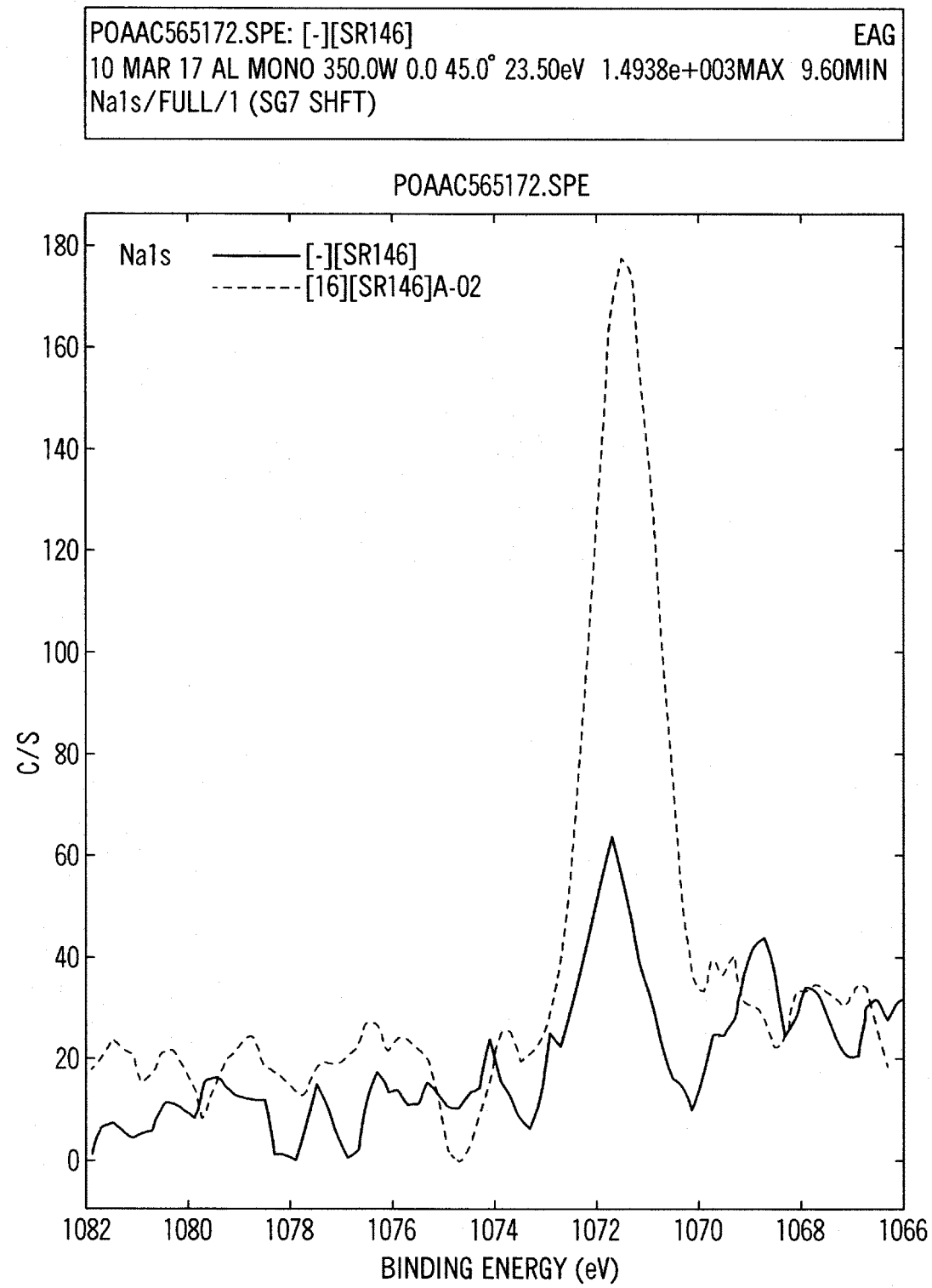
FIG. 12 shows high energy resolution Na1s spectra of Solvent Red 146 and modified Solvent Red 146 sample from Example 16.
Figure 13:
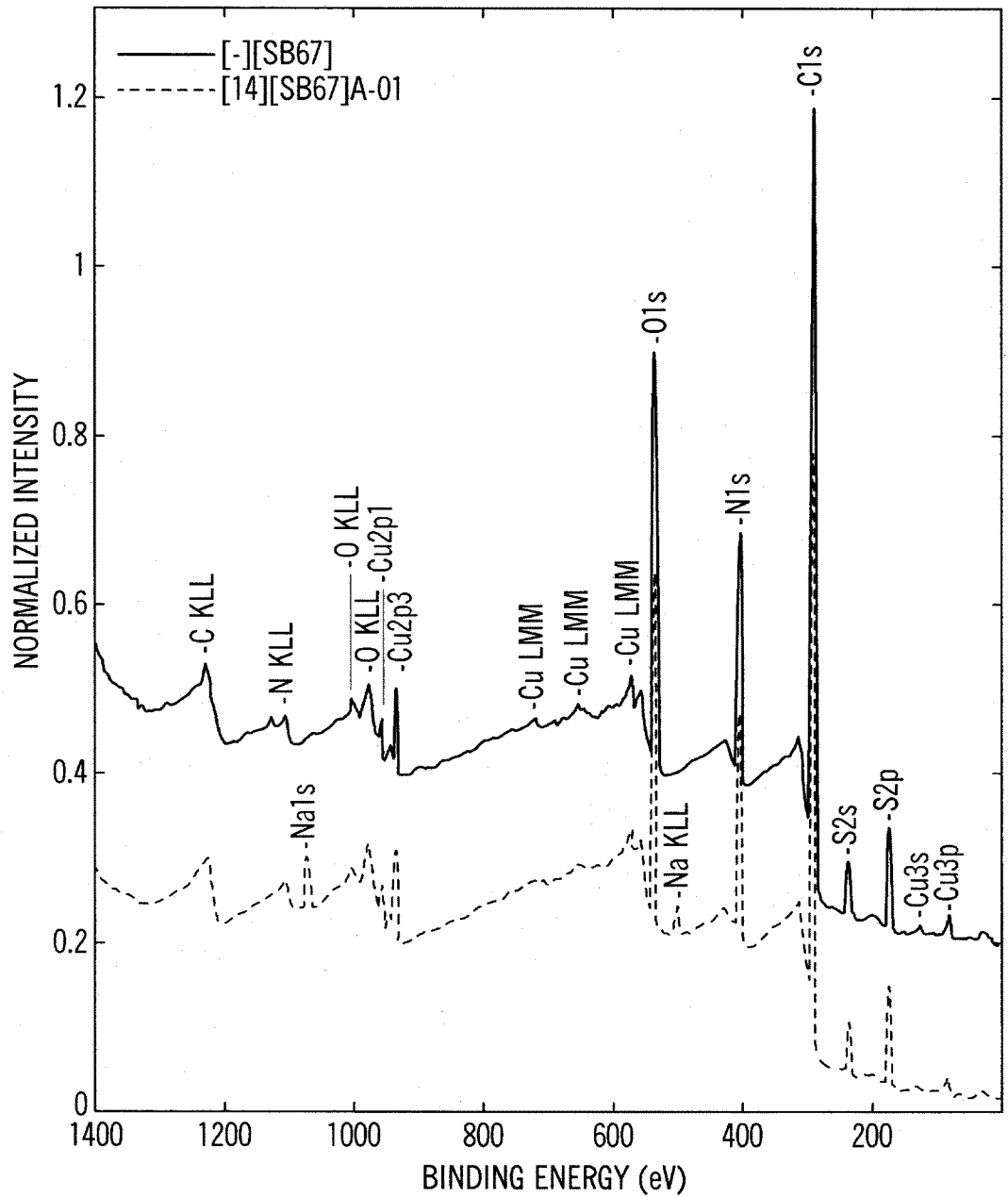
FIG. 13 shows low resolution X-Ray Photoelectron Spectroscopy (XPS) spectra of Solvent Blue 67 and modified Solvent Blue 67 sample from Example 14.
Figure 14:
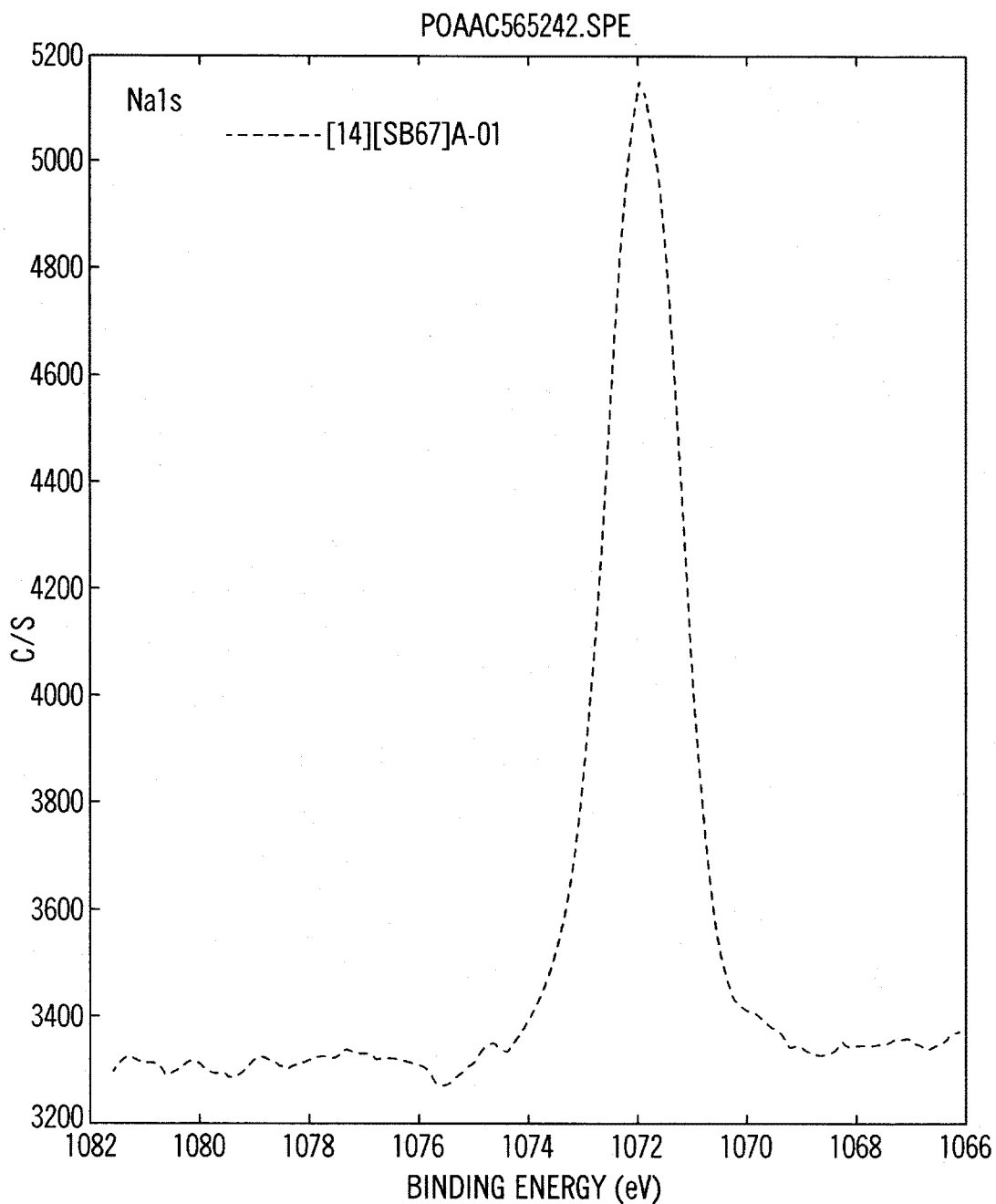
FIG. 14 shows high energy resolution Na1s spectrum of modified Solvent Blue 67 sample from Example 14.
Figure 15:
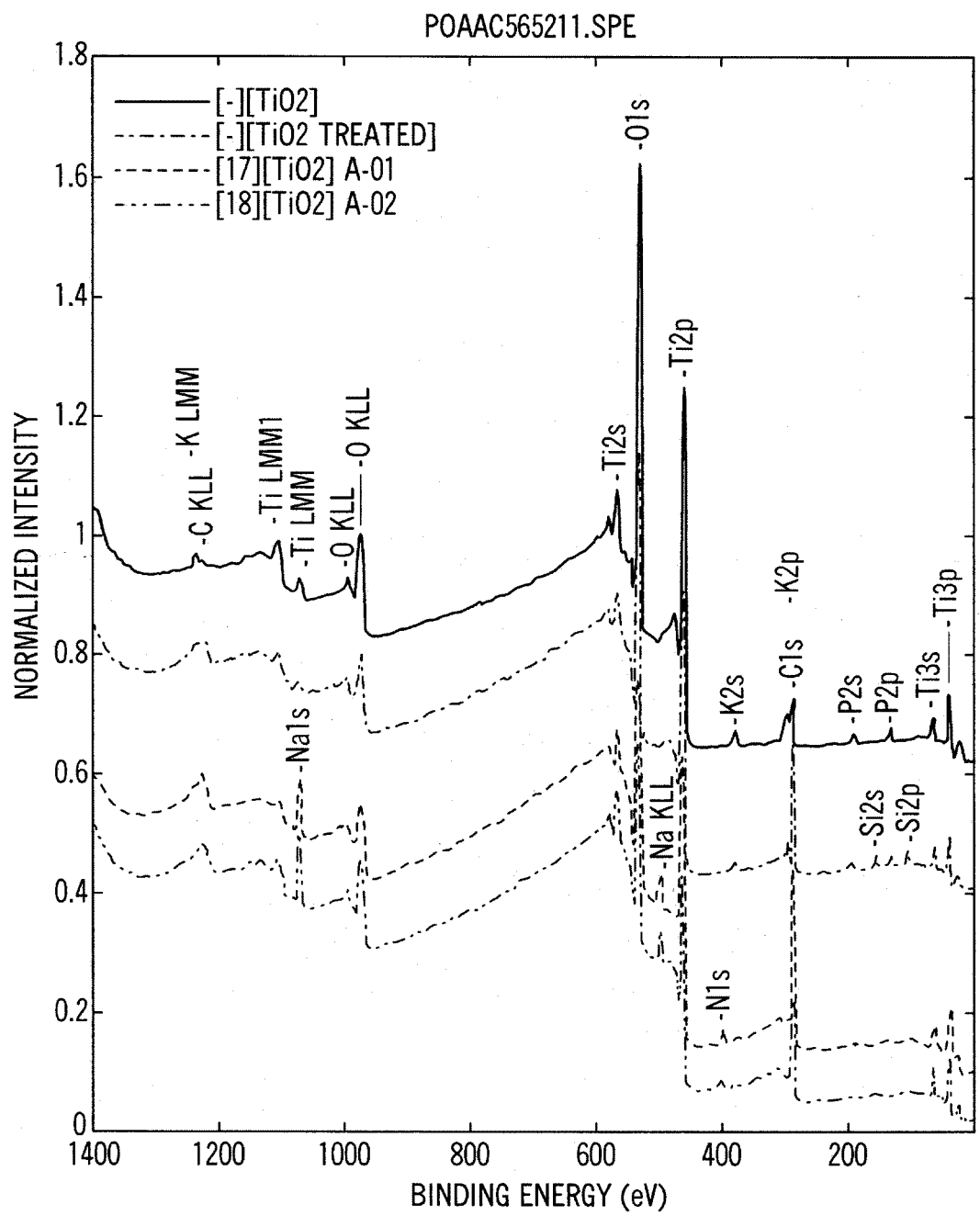
FIG. 15 shows low resolution X-Ray Photoelectron Spectroscopy (XPS) spectra of triethoxycaprylylsilane treated titanium dioxide, titanium dioxide pigments, and modified samples of each from Example 17 and 18.
Figure 16:
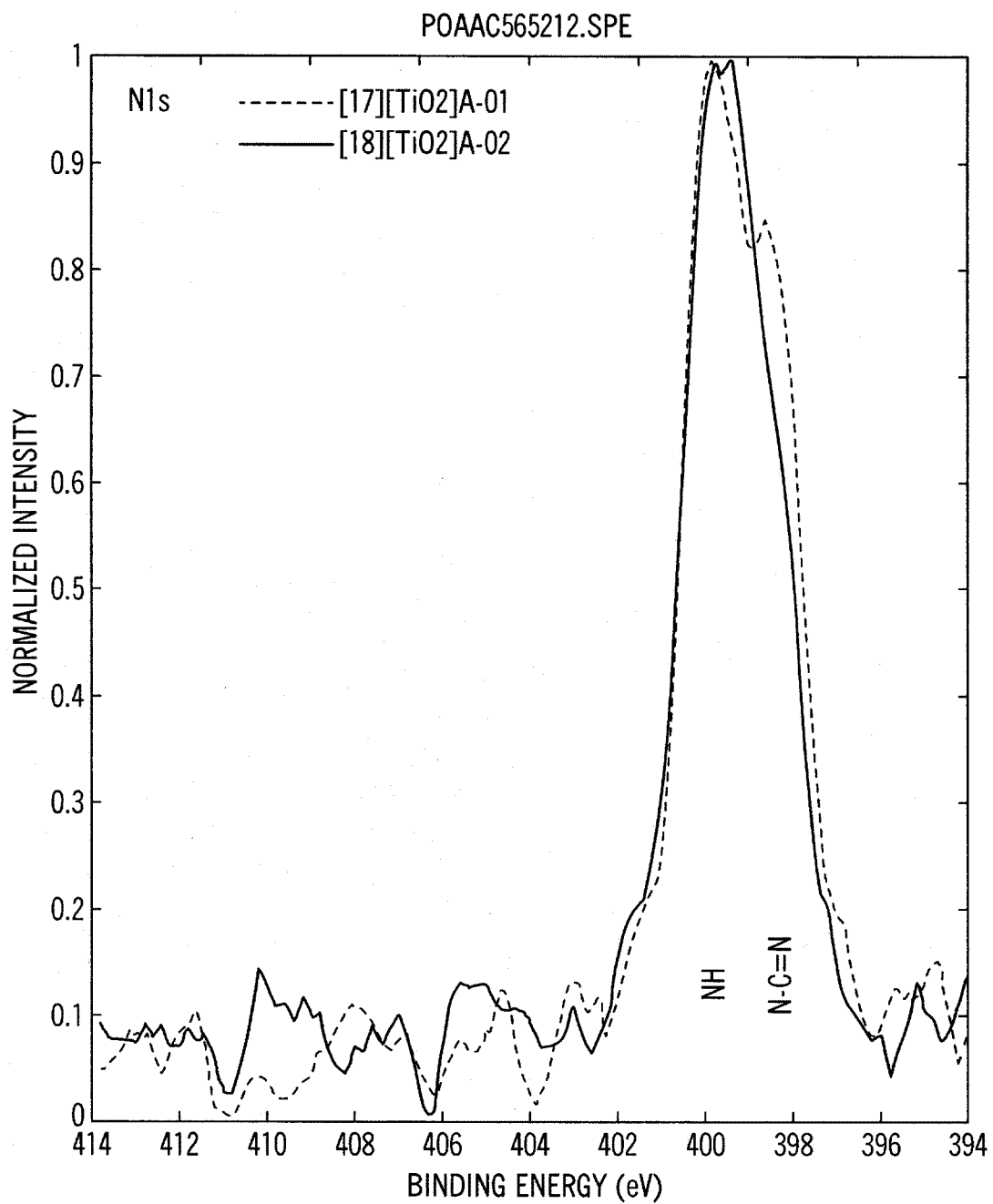
FIG. 16 shows high energy resolution N1s spectra of modified triethoxycaprylylsilane treated titanium dioxide and titanium dioxide pigments from Examples 17 and 18.
Figure 17:
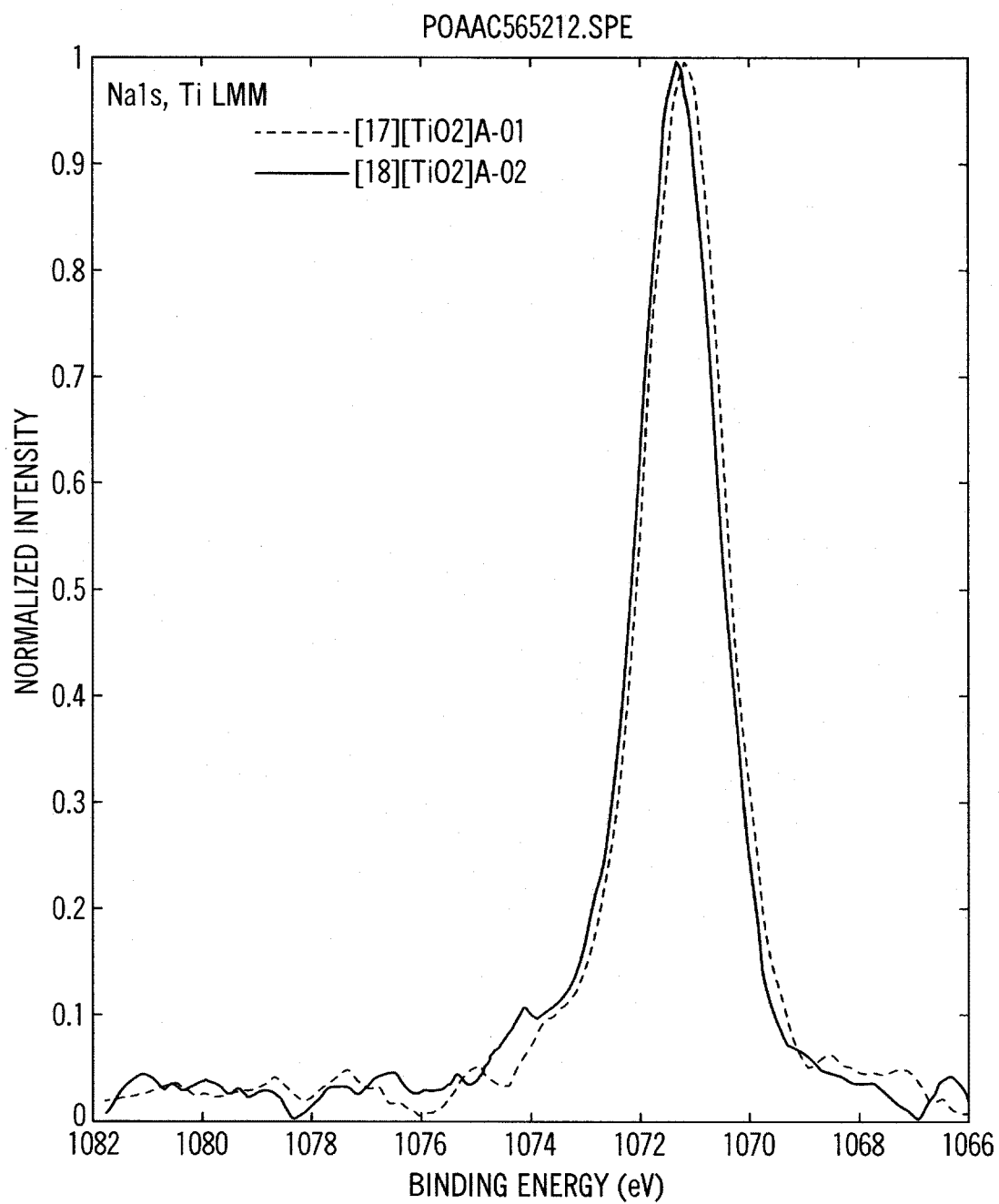
FIG. 17 shows high energy resolution Na1s spectra of modified triethoxycaprylylsilane treated titanium dioxide and titanium dioxide pigments from Examples 17 and 18.

The XPS results as shown in Table 8 and FIG. 4, indicate that the surface modification as disclosed yields a modified Disperse Blue 359 dye with an increase in surface sodium, as COONa, in about 0.3 atomic %.

The XPS results as shown in Table 8, indicate that the surface modification as disclosed yields a modified Disperse Yellow 54 dye with an increase in surface sodium, as COONa, in about 0.7 atomic %.

The XPS results, as shown in Table 8, indicate that the surface modification as disclosed yields a modified Disperse Brown 27 dye with an increase in surface sodium, as COONa, in about 0.1 atomic %

The XPS results, as shown in Table 8, indicate that the surface modification as disclosed yields a modified Disperse Blue 72 dye with an increase in surface sodium, as COONa, in about 0.4 atomic %.

The XPS results, as shown in Table 9, indicate that the surface modification as disclosed yields a modified Solvent Red 146 dye with an increase in surface sodium, as COONa, in about 0.3 atomic %.

The XPS results, as shown in Table 10, indicate that surface modification as disclosed yields a modified Triethoxycaprylylsilane treated Titanium Dioxide pigment with significantly higher surface carbon content (>16 atomic %), nitrogen content (1.2 atomic %) and sodium content (0.9 atomic %) compared to the original pigment.

The XPS results as shown in Table 10, indicate that the surface modification as disclosed yields a modified Titanium Dioxide pigment with significantly higher surface carbon content (>30.6 atomic %), nitrogen content (1.1 atomic %) and sodium content (1.1 atomic %) compared to the original pigment.

Figure 19:
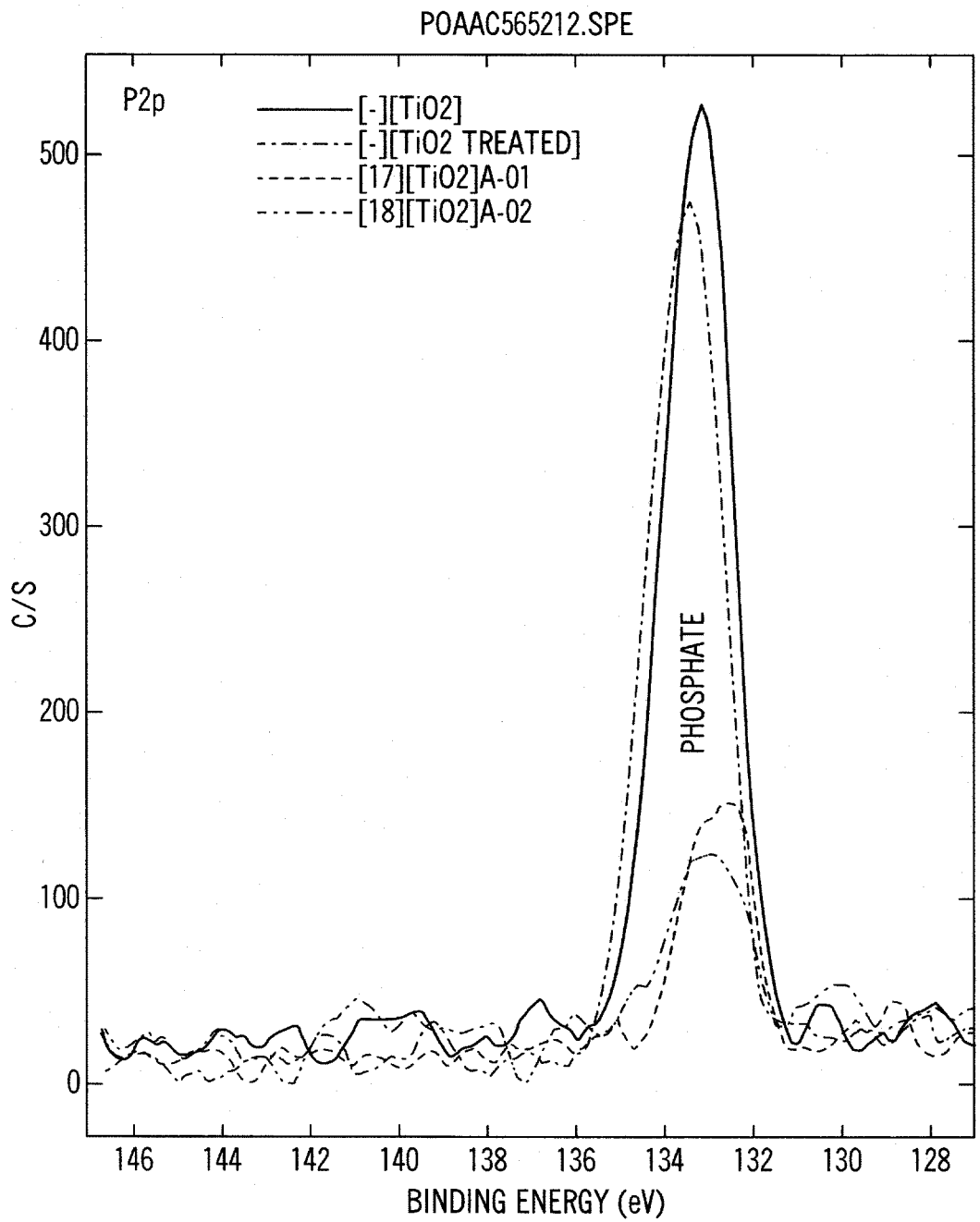
FIG. 19 shows high energy resolution P2p spectra of modified triethoxycaprylylsilane treated titanium dioxide, titanium dioxide pigments, and modified samples of each from Examples 17 and 18.
Figure 20:
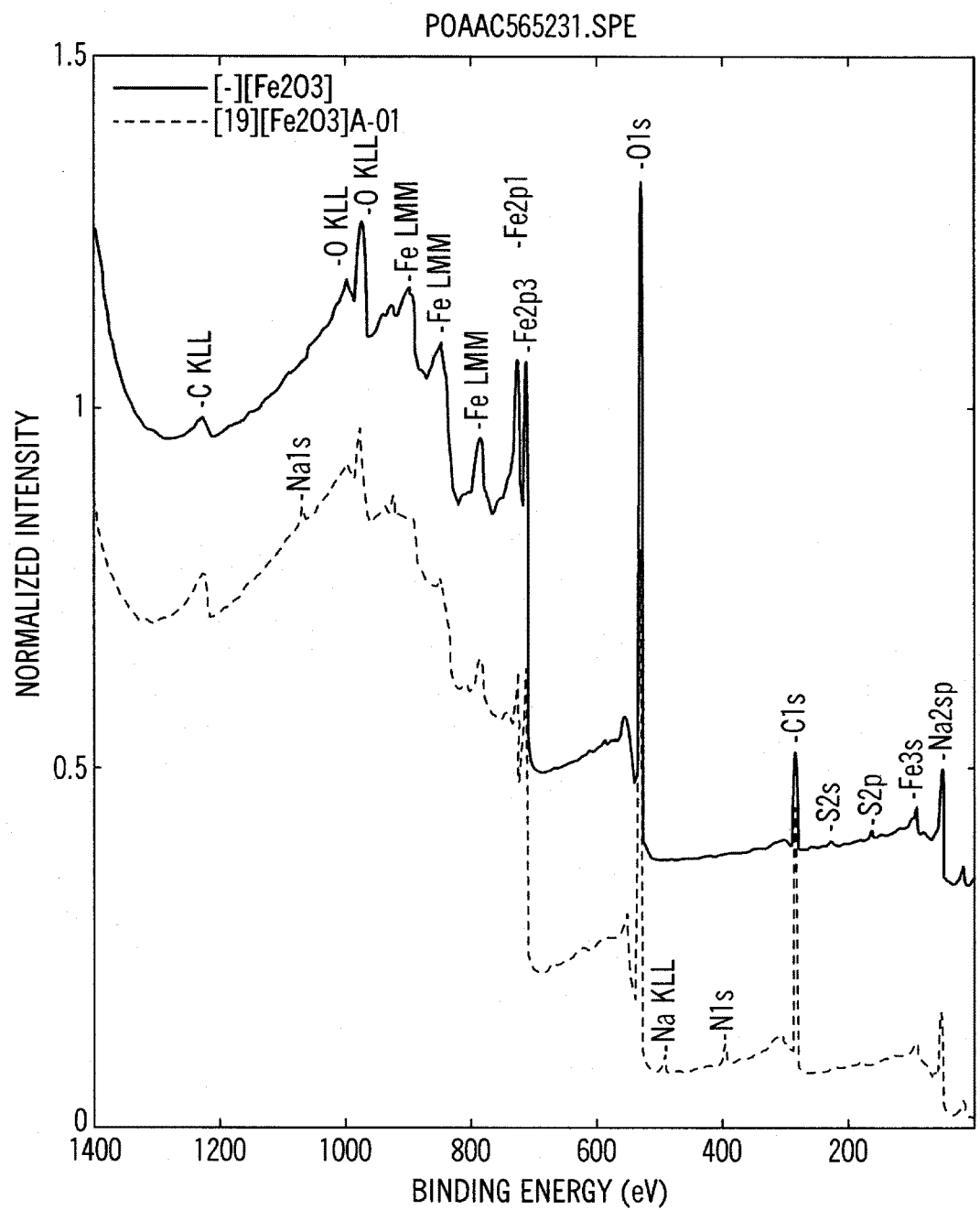
FIG. 20 shows low resolution X-Ray Photoelectron Spectroscopy (XPS) spectra of yellow iron oxide pigment, and modified yellow iron oxide pigment from Example 19.

The XPS results, as shown in Table 10 and FIG. 19, indicate that the surface modification as disclosed results in substantial removal of surface impurities present in the original titanium dioxide pigments as phosphorous compounds.

Figure 18:
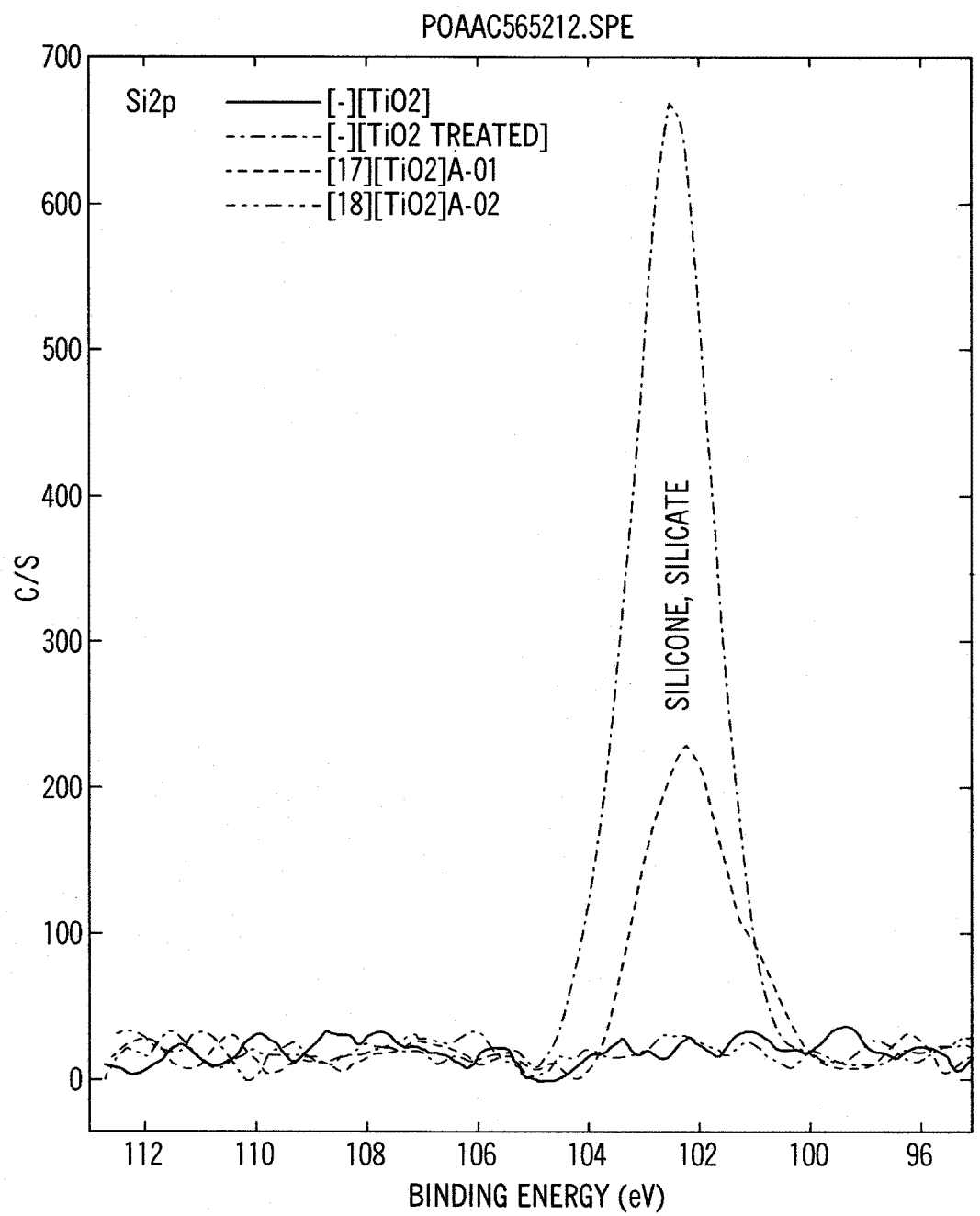
FIG. 18 shows high energy resolution Si2p spectra of modified triethoxycaprylylsilane treated titanium dioxide, titanium dioxide pigments, and modified samples of each from Examples 17 and 18.

The XPS results, as shown in Table 10 and FIG. 18, indicate that the surface modification as disclosed results in substantial removal of unattached silicon compounds present as impurities in the original triethoxycaprylylsilane treated titanium dioxide pigment.

Figure 21:
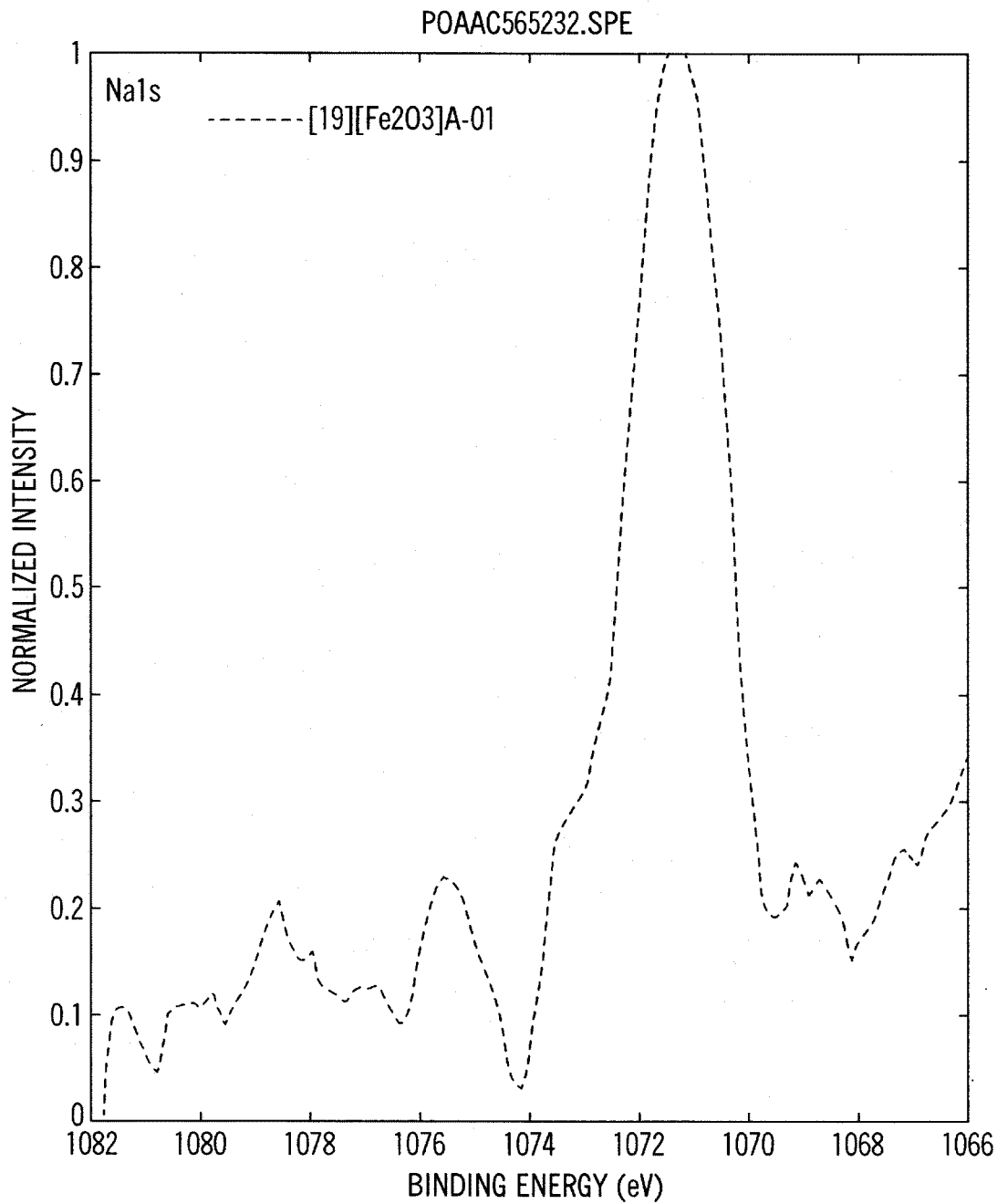
FIG. 21 shows high energy resolution Na1s spectrum of modified yellow iron oxide pigment sample from Example 19.

XPS results, as shown in Table 10 and FIG. 21, indicate that the surface modification as disclosed yields a modified Iron Oxide pigment with significantly higher surface carbon content (>25.1 atomic %), nitrogen content (1.1 atomic %) and sodium content (0.9 atomic %) compared to the original pigment.

Example 22

TABLE 11

Elemental analysis (% C, H, N, Ti, Si & Fe).

| Sample [Ex#] [Particle Type] | C | H | N | Fe | Ti | Si | Na[13] | K[13] | [H] m mol/g of pigment[14] |
|---|---|---|---|---|---|---|---|---|---|
| 1 [—] [DB359] | 69.47 | 4.44 | 14.37 | — | — | — | — | — | — |
| 2 [3] [DB 359] | 66.72 | 4.14 | 14.29 | 0.00 | 0.00 | 0.00 | 0.23 | 0.21 | 0.154 |
| 3 [10] [DB 359] | 64.16 | 5.34 | 9.93 | 0.00 | 0.00 | 0.00 | 0.43 | 0.38 | 0.284 |
| 4 [—] [DY54] | 74.36 | 3.75 | 4.68 | — | — | — | — | — | — |
| 5 [5] [DY54] | 72.34 | 4.08 | 4.73 | 0.00 | 0.00 | 0.00 | 0.46 | 0.07 | 0.218 |
| 6 [—] [DBr27] | 49.18 | 4.03 | 13.23 | — | — | — | — | — | — |
| 7 [7] [DBr27] | 50.35 | 4.39 | 12.19 | 0.00 | 0.00 | 0.00 | 0.71 | 0.09 | 0.332 |

TABLE 11-continued

Elemental analysis (% C, H, N, Ti, Si& Fe).

| Sample [Ex#] [Particle Type] | C | H | N | Fe | Ti | Si | Na[13] | K[13] | [H] m mol/g of pigment[14] |
|---|---|---|---|---|---|---|---|---|---|
| 8 [—] [SR146] | 72.30 | 3.88 | 4.14 | — | — | — | — | — | — |
| 9 [16] [SR146] | 71.49 | 4.20 | 3.98 | 0.00 | 0.00 | 0.00 | 0.51 | 0.06 | 0.237 |
| 10 [—] [DB72] | 76.47 | 4.54 | 4.11 | — | — | — | — | — | — |
| 11 [8] [DB72] | 75.70 | 4.72 | 4.02 | 0.00 | 0.00 | 0.00 | 0.31 | 0.04 | 0.145 |
| 12 [—] [TiO$_2$] | <0.5 | <0.5 | <0.04 | — | 52.90 | — | — | — | — |
| 13 [—] [TiO$_2$] - treated | <0.5 | <0.5 | <0.04 | — | 56.50 | 0.23 | — | — | — |
| 14 [17] [TiO$_2$] | 3.59 | <0.5 | 0.11 | — | 51.20 | 0.17 | 0.64 | 0.17 | 0.322 |
| 15 [18] [TiO$_2$] | 5.24 | 0.64 | 0.13 | — | 51.80 | <0.11 | 0.56 | 0.27 | 0.313 |
| 16 [—] [Fe$_2$O$_3$] | <0.5 | 1.21 | <0.07 | 59.20 | — | — | — | — | — |
| 17 [19] [Fe$_2$O$_3$] | 6.24 | 1.89 | 0.19 | 54.80 | 0.00 | 0.00 | 0.39 | 0.07 | 0.188 |
| 18 [—] [SB67] | 51.35 | 5.01 | 13.01 | — | — | — | — | — | — |
| 19 [14] [SB67] | 52.61 | 5.22 | 11.99 | 0.00 | 0.00 | 0.00 | 1.50 | 0.26 | 0.719 |

[13] The sodium and potassium were calculated at 100% solids from ICP metal analysis of the original dispersion as reported in Tables 5-1 for Solids (%) and Table 5-2 for Na and K ppm values.
[14] The concentration of mMoles of active hydrogen per gram of pigment particle was calculated using the percent sodium and potassium by using the formula: mMoles = % metal/atomic weight × 1000/100.

The results of the elemental analysis indicate that the surface modification as disclosed yields a modified Disperse Blue 359 dye with 0.154-0.284 mMoles of active hydrogen per gram of dye.

The results of the elemental analysis indicate that the surface modification as disclosed yields a modified Disperse Yellow 54 dye with approximately 0.218 mMoles of active hydrogen per gram of dye.

The results of the elemental analysis indicate that the surface modification as disclosed yields a modified Disperse Brown 27 dye with approximately 0.332 mMoles of active hydrogen per gram of dye.

The results of the elemental analysis indicate that the surface modification as disclosed yields a modified Disperse Blue 72 dye with approximately 0.145 mMoles of active hydrogen per gram of dye.

The results of the elemental analysis indicate that the surface modification as disclosed yields a modified Solvent Red 146 dye with approximately 0.237 mMoles of active hydrogen per gram of dye.

The results of the elemental analysis indicate that the surface modification as disclosed yields a modified Solvent Blue 67 dye with approximately 0.719 mMoles of active hydrogen per gram of dye.

The results of the elemental analysis indicate that the surface modification as disclosed yields a modified Titanium Dioxide pigment with approximately 5.2% carbon, 0.64% hydrogen, 013% nitrogen, and 0.313 mMoles of active hydrogen per gram of pigment.

The results of the elemental analysis indicate that the surface modification as disclosed yields a modified Triethoxycaprylylsilane treated Titanium Dioxide pigment with approximately 3.6% carbon, <0.5% hydrogen, 0.11% nitrogen, 0.17% silicon, and 0.322 mMoles of active hydrogen per gram of pigment.

The results of the elemental analysis indicate that the surface modification as disclosed yields a modified Iron Oxide pigment with approximately 6.2% carbon, 1.9% hydrogen, 019% nitrogen, and 0.188 mMoles of active hydrogen per gram of pigment.

Example 23

Particle Size Measurement and Stability Data

Samples comprising 8-15% solids were prepared by diluting one drop of sample to 15 ml deionized water and loading into a 1 cm disposable cuvette, avoiding air bubbles. Malvern Zetasizer Nano series Model ZEN3600 was then used to measure mean particle size in the sample.

TABLE 12

Particle Size Measurements and Stability data of Dispersions.

| Example | Dispersion | Viscosity | | | Particle Size | | | pH | |
|---|---|---|---|---|---|---|---|---|---|
| [#] | Id | Initial | Week 1 | Week 3 | Initial | Week 1 | Week 3 | Initial | Final |
| 5 | DY54 | 1.72 | 1.69 | 1.69 | 166 | 179 | 177 | 8.6 | 7.9 |
| 6 | DBr27[1] | 1.86 | 1.60 | 1.58 | 250 | 260 | 264 | 8.6 | 7.3 |
| 7 | DBr27[1] | 1.37 | 1.50 | 1.60 | 188 | 260 | 175 | 9.0 | 7.4 |
| 8 | DB72[2] | 1.66 | 1.74 | 1.78 | 153 | 230 | 230 | 8.4 | 7.7 |
| 15 | SR146[8] | 1.77 | 1.58 | 1.55 | 159 | 153 | 171 | 8.0 | 7.4 |
| 16 | SR146[8] | 1.28 | 1.40 | 1.39 | 159 | 167 | 168 | 8.8 | 7.5 |

The following ink jet inks were made according to the procedure described in following examples:

Example 24

A ink jet ink was prepared by mixing 19.1 g of the purified dispersion described in example 10, 23 g of glycerol, 0.05 g of Dowicil 200 (from Dow Chemical), 0.1 g of Acticid TBW (from Thor GmbH, Germany), 4.5 g of Reax 907 (from Meadwestwaco, USA) and 53.2 g. of demineralized water. The ink so obtained was filtered through a 1 micron nominal glass-filter. Static surface tension measured with a DuNoüy ring was 43.2 dynes/cm and viscosity measured at 23° C. with a cone-plate rheometer was 4.3 mPas. This ink is printed on Coldenhove HTR2000 paper (available form Coldenhove Papier B.V, Holland) using a Mimaki JV4 printer at a resolution of 720*720 dpi and a coverage of 100%. The printed paper is transferred on 100% polyester fabric at 210° C. during 30 sec. under a pressure of 2 bars with a calander (available form Storck; Holland). The Lab values of the fabric after transfer are measured using a Datacolor spectrophotometer SF450X Spectraflash (available from Datacolor AG, Switzerland). A commercial ink, namely S4 Subli Blue 770[4] containing the same amount of DB359 dye as measured by light absorption at 580 nm with a UV-Vis spectrophotometer (Shimadzu UV-2501PC, Shimadzu, Japan) was printed under the same conditions. The colorimetric Lab values of the 2 inks are given in the Table 13 and show that the ability to sublimate of the dye is not affected by the attachment reaction.

TABLE 14

Colorometric L*a*b Values

| Ink | L | a | b |
| --- | --- | --- | --- |
| Example #25 | 40 | 2.8 | −52.8 |
| S4 Subli Blue 770 | 40.5 | 2.4 | −53.5 |

Example 26

Inkjet inks have been prepared by mixing the ingredients described in the table 15. The dye contents were measured with a UV-Vis spectrophotometer.

TABLE 15

InkJet Ink Formulations

| Ink | Dye Dispersion source | Quantity [g] | Glycerol [g] | Dowicil 200 [g] | Triethanolamine [g] | Dye content [%] |
| --- | --- | --- | --- | --- | --- | --- |
| Yellow | Example 5 | 21.8 | 20 | 0.1 | 0.5 | 1.9 |
| Brown | Example 7 | 44.6 | 25 | 0.1 | — | 3 |
| Red | Example 16 | 51.2 | 25 | 0.1 | — | 4.2 |

TABLE 13

Colorometric L*a*b Values

| Ink | L | a | b |
| --- | --- | --- | --- |
| Example | 31.2 | 17.5 | −52.4 |
| S4 Subli Blue 770 | 30.3 | 18.5 | −52.3 |

Example 25

A cyan ink jet ink was prepared by mixing 37.3 g of the purified dispersion from Example 11, 46 g. of glycerol, 0.2 g of Dowicil 200, 1 g of triethanolamine, 7 g of Reax LS (from Meadwestwaco, USA) and 108.5 g of DI water. The ink so obtained was filtered through a 1 micron nominal glass-filter. Static surface tension measured with a DuNoüy ring was 43.7 dynes/cm and viscosity measured at 23° C. with a cone-plate rheometer was 4.1 mPas. This ink is printed on Coldenhove HTR2000 paper (available form Coldenhove Papier B.V, Holland) using a Mimaki JV4 printer at a resolution of 540*360 dpi and coverage of 100%. The printed paper is transferred on 100% polyester fabric at 210° C. during 30 sec. under a pressure of 2 bars. The Lab values of the fabric after transfer are measured using a Datacolor spectrophotometer SF450X Spectraflash (available from Datacolor AG, Switzerland). A commercial ink, namely S4 Subli Blue 770[4] containing the same amount of DB359 dye as measured by light absorption at 580 nm with a UV-Vis spectrophotometer (Shimadzu UV-2501PC, Shimadzu, Japan) was printed under the same conditions. The colorimetric Lab values of the 2 inks are given in the Table 14 and show that the ability to sublimate of the dye is not affected by the attachment reaction.

The ingredients were mixed and the inks obtained were filtered through a 1 micron nominal glass-filter. Static surface tensions of the inks were measured with a DuNoüy ring. Viscosities were measured at 23° C. with a cone-plate rheometer. These inks are printed on Coldenhove HTR2000 paper (available form Coldenhove Papier B.V, Holland) using a Mimaki JV4 printer at a resolution of 540*360 dpi and coverage of 100%. The printed paper is transferred on 100% polyester fabric at 210° C. during 30 sec. under a pressure of 2 bars. The Lab values of the fabric after transfer are measured using a Datacolor spectrophotometer SF450X Spectraflash (available from Datacolor AG, Switzerland). Corresponding commercial inks from the S4 Subli range (Sensient Imaging—Specialty Colors and Inks, Switzerland) containing the same amount of dye were printed under the same conditions. The colorimetric Lab values of the different inks are given in the Table 16 and show that the ability to sublimate of the dye is not affected by the attachment reaction.

TABLE 16

Colorometric L*a*b Values

| Ink | Viscosity [mPas] | Surface tension [mN/m] | L | a | b |
| --- | --- | --- | --- | --- | --- |
| Yellow | 2.2 | 37.7 | 86.4 | −4.7 | 94.7 |
| Commercial Yellow | 2.9 | 38.2 | 86.6 | −6 | 94.4 |
| Brown | 2.6 | 38.2 | 33.9 | 43.4 | 22.9 |
| Commercial Brown | 3.4 | 22 | 36.3 | 45.2 | 24.8 |
| Red | 2.7 | 39 | 41.3 | 68.1 | 21.3 |
| Commercial Red | 5 | 37.1 | 44 | 69.9 | 19.2 |

Example 27

A cyan ink jet ink was prepared by mixing 65.9 g of the purified dispersion from Example 11, 25 g of glycerol, 0.1 g of Dowicil 200 and 9 g of DI water. The ink so obtained was filtered through a 1 micron nominal glass-filter. Static surface tension measured with a DuNoüy ring was 39.1 dynes/cm and viscosity measured at 23° C. with a cone-plate rheometer was 5.8 mPas. This ink is printed on Coldenhove Screencol paper (available form Coldenhove Papier B.V, Holland) and on 100% ready to print cotton using a Mimaki JV4 printer at a resolution of 720*720 dpi and coverage of 100%. The Lab values of the prints are measured using a Datacolor spectrophotometer SF450X Spectraflash (available from Datacolor AG, Switzerland).

TABLE 17

Colorometric L*a*b Values

| Substrate | L | a | b |
|---|---|---|---|
| Screened paper | 45.7 | −16.9 | −30.8 |
| Cotton | 51.2 | −15.3 | −31.4 |

Example 28

Example of converting a water-insoluble dye particle to a self dispersed aqueous dispersion by treatment of cyanuryl tris adduct with sulfanilic acid.

Each of Examples 3-19 above is repeated using a cyanuryl tris adduct prepared with sulfanilic acid (Example 1a) in place of a cyanuryl tris adduct prepared with 4-aminobenzoic acid (Example 2).

Example 29

Example of converting a water-insoluble dye particle to a self dispersed aqueous dispersion by treatment of cyanuryl tris adduct with 4-aminophenol.

Each of Examples 3-19 above is repeated using a cyanuryl tris adduct prepared with 4-aminophenol (Example 1b) in place of a cyanuryl tris adduct prepared with 4-aminobenzoic acid (Example 2).

Example 30

Wood Stain Application Performance

Wood stains are prepared and tested at 6% of one or more modified particles from the above Examples loading with a resin solution consisting of 18% Joncryl 95 (available from BASF) and the balance de-ionized water. Waterfastness comparison of drawdowns on Leneta Form 3NT-3 using a wire wound rod #7 (available from Paul N. Gardner Company, Pompano Beach, Fla.) is done with 1"×4" strips. Half of each strip is dipped in de-ionized water for one minute. The strips are allowed to dry at ambient temperature. The color difference (DE*) is read with Datacolor SF600 PLUS-CT colorimeter. The stains are expected to show improved waterfastness as demonstrated by lower DE*.

Example 31

Coating Performance

Coating formulations (Masstone) are prepared and tested at 6% of one or more modified particles from the above Examples loading with a resin solution consisting of 25% acrylic vehicle (available from Valspar, Wheeling, Ill.) and the balance de-ionized water. Each Masstone color is mixed with a latex-based tint base (available from Sherwin Williams, Cleveland, Ohio) at 1:10 ratio for the tint preparation. The drawdown is prepared on Leneta form 2A using a 6.0 mil wire wound rod. Chemical resistance is measured separately by spotting 10 drops of 10% hydrochloric acid and 10 drops of 10% sodium hydroxide solution on a Masstone drawdown. The degree of chemical resistance is measured by taking the DE* value between the spotted area versus the control area. The coating formulations are expected to demonstrate improved chemical resistance as measured by the DE*.

Example 32

Color Filter Application Performance

Color filter formulations are prepared and tested at 6% of one or more modified particles from the above Examples loading adjusted to 75% of the total with de-ionized water and then mixed with a vehicle (25%) consisting of 30% Valspar acrylic vehicle, 30% Joncryl 1972 (available from BASF) and 40% 1-methoxy-2-propanol (Propylene Glycol Monomethyl Ether). Transmission values of the color filter coatings on a transparent olefin polymer substrate using a wire wound rod #7 (Paul N. Gardner Company, Pompano Beach, Fla.) are measured after drying at ambient temperature.

Example 33

Cosmetic Application Performance

Oil-in-water and water-in-silicone emulsions were prepared with modified titanium dioxide pigment dispersion from Example 17. Materials used in preparation of the oil-in-water and water-in-silicone emulsions are described in Table 18.

TABLE 18

Materials used in preparation of oil-in-water and water-in-silicone emulsions.

| Emulsion Ingredient | INCI | FUNCTION/BENEFIT |
|---|---|---|
| Submica N | Mica | High swelling capacity by oil absorption with good penetration and silky non greasy feeling, |
| Natpure SOL | Glycerin(and)Sucrose laurate(and)Sucrose dilaurate(and)Sucrose trilaurate(and)Sorbitol | Excellent emulsifier for O/W emulsion |
| Fructosol | *Chicory intybus* | Skin moisturizer |
| Covacryl MV60 | Sodium Polyacrylate | Thickener |
| Submica N | Mica | High swelling capacity by oil absorption with good penetration and silky non greasy feeling, |
| Covasterol | Glyceryl isostearate (and) Isostearyl alcohol (and)Beta sitostearol (and) Shea butter (and) Candelilla wax | Cell regenerating, moisturizing and nourishing |
| Silamer | Phenyl trimethicone (and) Cetyl Dimethicone copolyol(and) Polyglyceryl-2-Isostearate (and) Hexyl laurate | Non-ionic self-emulsifying base |
| Squatol S | Hydrogenated polyisobutene | Emollient; Imparts a coherent film that protects the skin |
| Covabead LH 85 | Methyl methacrylate crosspolymer | High capacity of water and oil absorption; Ultra fine powder with exceptional feel and spread ability on skin |

TABLE 18-continued

Materials used in preparation of oil-in-water and water-in-silicone emulsions.

| Emulsion Ingredient | INCI | FUNCTION/BENEFIT |
|---|---|---|
| Base O/W 097 | Ceteareth 25(and)PEG-2 stearate(and) Paraffinum liquidum(and)Hydrogenated coconut oil(and)Cetyl alcohol(and)Sodium stearate | Self emulsifying and emollient base |

Table 19 provides the formulation for the oil-in-water emulsion prepared as described below.

TABLE 19

Formulation for oil-in-water emulsion with pigment dispersion from Example 17.

| | % W/W |
|---|---|
| Phase A | |
| Jojoba Oil | 3.00 |
| Cetearyl Alcohol | 1.00 |
| Shea Butter | 1.60 |
| Phase B1 | |
| Pure Water | 44.40 |
| NATPURE SOL | 6.00 |
| FRUCTOSOL | 1.00 |
| Glycerin | 1.50 |
| Preservative | 0.50 |
| Phase B2 | |
| Example 17 dispersion | 30.00 |
| Phase C | |
| SUBMICA N | 10.00 |
| Phase D | |
| Propylene Glycol | 0.50 |
| COVACRYL MV60 | 0.50 |

Oil in Water Emulsion Manufacturing Procedure:
1. Prepare Phase A, mix and heat to 50° C. until homogenous.
2. Prepare Phase B1/B2 and then add to Phase A. Mix with a Turrax homogenizer for 1 minute.
3. Cool while mixing to 40° C. then add Phase C.
4. Add thickener (Phase D) and continue mixing until thick and creamy.
5. Put into an appropriate container. pH=7.60

Table 20 provides the formulation for the water-in-silicone emulsion prepared as described below.

TABLE 20

Formulation for water-in-silicone emulsion with pigment dispersion from Example 17

| | W/W % |
|---|---|
| Phase A | |
| SILAMER | 16.00 |
| COVASTEROL | 4.50 |
| COVABEAD LH 85 | 2.00 |
| SUBMICA N | 10.00 |
| Synthetic Beeswax | 3.00 |
| Phase B | |
| Example 17 dispersion | 30.00 |
| Glycerin | 5.00 |
| Preservative | 0.50 |
| Phase C | |
| SQUATOL S | 6.00 |
| Base O/W 097 | 5.00 |
| Pure water | 18.00 |
| | 100.00% |

Water in Silicon Emulsion Manufacturing Procedure:
1. In Phase A, mix and heat to 70° C. until homogenous.
2. Mix Phase B and C separately until homogenous without heat.
3. Add B to Bulk until emulsified. Add Bulk to C slowly and maintain temperature at 70° C.
4. Continue mixing until thickening occurs.
5. Put into an appropriate container.

Figure 22:
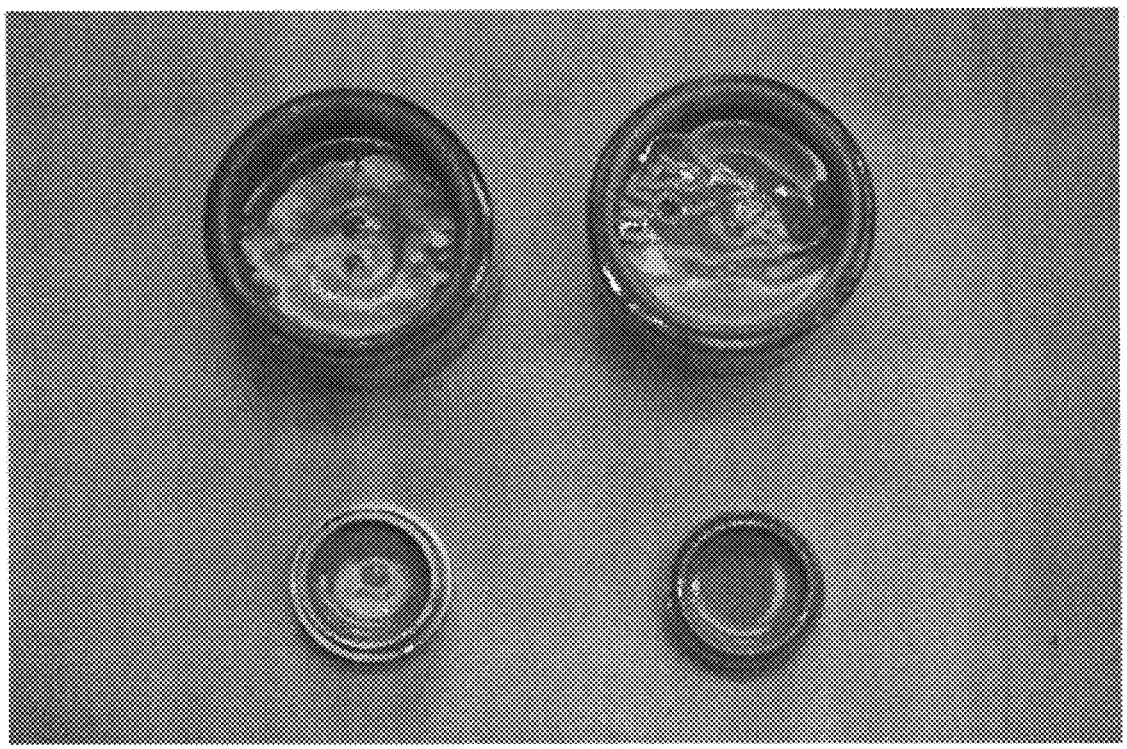
FIG. 22 shows a photograph of oil-in-water emulsions (upper left and lower left) and water-in-silicone emulsions (upper right and lower right) prepared with modified titanium dioxide pigment dispersion.

Referring to FIG. 22, the upper left sample shows an oil in water emulsion prepared as described in this Example, stored at 23° C. for 14 days, whereas the lower left sample shows the same oil in water emulsion stored at 50° C. for 7 days. The upper right sample shows a water-in-silicone emulsion prepared as described in this Example, stored at 23° C. for 14 days, whereas the lower left sample shows the same oil in water emulsion stored at 50° C. for 7 days. A comparison of the emulsions stored at 23° C. to those stored at 50° C. demonstrates the thermal stability of the two emulsions.

A benefit of the modified pigment vs. the original pigment is the dispersibility and the ease of dispersion. Both the emulsions were relatively easy to form using the Example 17 dispersion without any significant use of shear. Without being bound by a particular theory, it is believed that the temperature stability is higher in emulsions including modified pigment dispersion than in emulsions including traditional pigments due to their small particle size and wetting characteristics. This would keep the particles suspended for a long period of time. Since dispersion would be easier and better, color strengths are also expected to be better with modified pigments.

Example 34

Correction Fluid Application Performance

Water-based correction fluid compositions including a modified opacifying agent, (e.g., titanium dioxide as prepared in Example 17) are prepared according to methods well known to those skilled in the art. (See, e.g., U.S. Pat. No. 6,025,413, U.S. Pat. No. 4,654,081, U.S. Pat. No. 4,165,988, and U.S. Pat. No. 3,997,498, the disclosures of which are hereby incorporated by reference in their entirety.)

Example 35

Markers and Pens

The modified particles of the above Examples are incorporated into markers and writing pens using methods known in the art.

What is claimed is:

1. A method of modifying a particle, the method comprising:
   reacting a reactive compound having an X—[Y]$_n$ reactive group with a secondary compound N—S-ZM to form a substituted reactive intermediate [Y]$_a$—X—(N—S-ZM)$_b$; and
   reacting the particle with the substituted reactive intermediate [Y]$_a$—X—(N—S-ZM)$_b$ to attach the substituted reactive intermediate to the surface of the particle to form a surface modified particle, the particle comprising at least one of a dye particle, an inorganic pigment particle, an additive, or a combination thereof;
   wherein X is a sulfonyl, phosphoryl, or 1,3,5-triazinyl group;
   Y is a halogen leaving group;
   N is a nucleophilic group;
   S is an organic group;
   ZM is an ionizable end group;
   n is an integer between 1 and 3;
   b is an integer between 1 and 3; and
   a=n−b;
   wherein n is equal to or greater than b; and
   wherein if b is 2 or 3, each N—S-ZM can be the same or different.

2. The method of claim 1, wherein X is a 1,3,5-triazinyl group.

3. The method of claim 1, wherein b is 2 or 3, and each N—S-ZM is different.

4. The method of claim 3, wherein the X—[Y]$_n$ reactive group comprises cyanuric chloride, and the secondary compounds comprise 4-aminobenzoic acid and a polymeric amine.

5. The method of claim 1, wherein Y comprises at least one of fluorine, chlorine, bromine, or iodine.

6. The method of claim 1, wherein N comprises at least one of an amine, an imine, a pyridine, or a thiol group.

7. The method of claim 1, wherein S comprises at least one of substituted or unsubstituted alkyls, aryls and polymer chains having a molecular weight range from about 300 to about 8000.

8. The method of claim 1, wherein Z comprises at least one of a carboxyl, sulfonyl, phenolic, or phosphoryl group and M comprises at least one of a proton or cation in salt form.

9. The method of claim 1, wherein the secondary compound N—S-ZM comprises at least one of a polymer, an amine, an amino acid, an alcohol, a thiol, and a combination thereof.

10. The method of claim 9, wherein the secondary compound N—S-ZM comprises at least one of amino benzoic acids, amino benzene sulfonic acids, amino phenols, amino sulfonic acids, polyethoxylated amino acids, sodium sulfanilate, sulfanilic acid, sodium p-aminobenzoate, p-aminophenol, ethyl 4-aminobenzoate, taurine, oleic acid (amino), tetramethylammonium 4-aminobenzoate, sodium 4-aminophenolate, sodium aminooleate, organic polymeric substrates, and combinations thereof.

11. The method of claim 10, wherein the organic polymeric substrates comprises at least one of linear alkyl and branched ethoxy and propoxy chain polymers with a molecular weight of about 300 to about 3000, linear polyethoxy polymeric amines, linear propoxy polymeric amines, styrene acrylic copolymers, polyethyleneimines, and combinations thereof.

12. The method of claim 1, wherein Z comprises at least one of ammonium, trimethylammonium, or tributylammonium and M comprises at least one of a halide or a negatively charged ion.

13. The method of claim 1, wherein the secondary compound N—S-ZM comprises at least one of a diamino aromatic, a polyethyleneimine, a polyguanidine, a quaternary ammonium compound, or a combination thereof.

14. The method of claim 1, wherein the particle comprises at least one of Disperse Blue 14, Disperse Blue 19, Disperse Blue 72, Disperse Blue 334, Disperse Blue 359, Disperse Blue 360, Disperse Orange 25, Disperse Yellow 54, Disperse Yellow 64, Disperse Red 55, Disperse Red 60, Macrolex Red H, Disperse Brown 27, Solvent Blue 67, Solvent Blue 70, Solvent Red 49, Solvent Red 146, Solvent Red 160, Solvent Yellow 162, Solvent Violet 10, Solvent Black 29, Acid Yellow 204, Acid Yellow 151, Acid Orange 60, Acid Red 182, Acid Red 357, Acid Red 359, Acid Blue 193, Acid Brown 355, Acid Violet 90, Acid Black 172, Acid Black 194, Acid Black 52, Acid Black 60, titanium (IV) oxide, iron (III) oxide, zinc oxide, and combinations thereof.

15. The method of claim 1, further comprising milling the particle to less than about 200 nm before, during, or after reacting the pigment with the substituted reactive intermediate.

16. The method of claim 1, wherein the substituted reactive intermediate [Y]$_a$—X—(N—S-ZM)$_b$ is associated with charge-balancing counterions, further comprising at least partially substituting the counterions with at least one of alkali metals, alkaline earth metals, NR$_1$R$_2$R$_3$H$^+$, and combinations thereof, wherein R$_1$, R$_2$, and R$_3$ are independently H or substituted or unsubstituted C$_1$-C$_5$ alkyl groups.

17. The method of claim 16, wherein the counterions are at least partially substituted with at least one of K$^+$, Li$^+$, NH$_4^+$, monoethanolammonium, tetraethylammonium, triethanolammonium, tetramethylammonium, tetrabutylammonium, and combinations thereof.

18. The method of claim 1, further comprising incorporating the surface modified particle into an aqueous particle dispersion.

19. A wood stain, coating, inkjet ink, color filter, or textile printing ink, comprising the surface modified particle produced by the method of claim 1.

20. The method of claim 1, wherein the X—[Y]$_n$ reactive group is cyanuric chloride and the secondary compound N—S-ZM is at least one of 4-aminobenzoic acid, sulfanilic acid, 4-aminophenolate, taurine, oleic acid (amino), linear polyethoxy polymeric amines, linear propoxy polymeric amines, or combinations thereof.

21. The method of claim 1, wherein the surface modified particle is a self-dispersing particle.

22. The method of claim 1, wherein the surface modified particle comprises about 0.1 to about 0.8 mMoles of active hydrogen per gram of particle.

23. The method of claim 1, wherein the surface modified particle comprises a total amount of alkali metal equivalent to about 0.1 to about 0.8 mMoles of active hydrogen per gram of particle.

24. The method of claim 23, wherein the surface modified particle comprises the dye particle.

25. The method of claim 23, wherein the surface modified particle comprises the inorganic pigment particle, about 2 to about 7 percent of carbon, about 0.1 to about 2 percent of hydrogen, and about 0.1 to about 0.5 mMoles of active hydrogen per gram of the inorganic pigment particle.

26. The method of claim 23, wherein the particle comprises a least one of titanium oxide, iron oxide, or zinc oxide.

* * * * *